United States Patent
Davies

(10) Patent No.: US 11,452,291 B2
(45) Date of Patent: *Sep. 27, 2022

(54) INDUCTION OF A PHYSIOLOGICAL DISPERSION RESPONSE IN BACTERIAL CELLS IN A BIOFILM

(71) Applicant: The Research Foundation for The State University of New York, Binghamton, NY (US)

(72) Inventor: David G. Davies, Binghamton, NY (US)

(73) Assignee: The Research Foundation for The State University, Binghamton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,561

(22) Filed: May 13, 2020

(65) Prior Publication Data

US 2020/0275653 A1    Sep. 3, 2020

Related U.S. Application Data

(62) Division of application No. 13/945,207, filed on Jul. 18, 2013, now Pat. No. 10,653,140, which is a division of application No. 12/154,347, filed on May 22, 2008, now abandoned.

(60) Provisional application No. 61/018,639, filed on Jan. 2, 2008, provisional application No. 60/917,791, filed on May 14, 2007.

(51) Int. Cl.

| | | |
|---|---|---|
| *A01N 37/06* | (2006.01) | |
| *A61Q 11/00* | (2006.01) | |
| *A01N 37/02* | (2006.01) | |
| *A61K 8/36* | (2006.01) | |
| *A01N 37/18* | (2006.01) | |
| *A61K 8/49* | (2006.01) | |
| *G02B 1/04* | (2006.01) | |

(52) U.S. Cl.
CPC ............. *A01N 37/06* (2013.01); *A01N 37/02* (2013.01); *A01N 37/18* (2013.01); *A61K 8/361* (2013.01); *A61K 8/4973* (2013.01); *A61Q 11/00* (2013.01); *G02B 1/043* (2013.01)

(58) Field of Classification Search
None
See application file for complete search history.

(56) References Cited

U.S. PATENT DOCUMENTS

| | | |
|---|---|---|
| 4,097,604 A | 6/1978 | Thiele |
| 4,214,006 A | 7/1980 | Thiele |
| 4,215,144 A | 7/1980 | Thiele |
| 4,224,307 A | 9/1980 | Thiele et al. |
| 4,442,125 A | 4/1984 | Thiele |
| 4,976,874 A | 12/1990 | Gannon et al. |
| 4,978,685 A | 12/1990 | Gannon et al. |
| 5,428,101 A | 6/1995 | Urano et al. |
| 5,645,841 A | 7/1997 | Hill et al. |
| 5,753,180 A | 5/1998 | Burger |
| 5,798,117 A | 8/1998 | New et al. |
| 6,086,921 A | 7/2000 | Domenico |
| 6,106,854 A | 8/2000 | Belfer et al. |
| 6,207,149 B1 | 3/2001 | Fuglsang et al. |
| 6,241,994 B1 | 6/2001 | Lee et al. |
| 6,248,371 B1 | 6/2001 | Domenico |
| 6,348,187 B1 | 2/2002 | Pan et al. |
| 6,455,031 B1 | 9/2002 | Davies et al. |
| 6,641,739 B2 | 11/2003 | Dresty, Jr. et al. |
| 6,692,757 B1 | 2/2004 | Day et al. |
| 6,696,047 B2 | 2/2004 | Scott et al. |
| 6,793,900 B1 | 9/2004 | Morck et al. |
| 6,830,745 B1 | 12/2004 | Budny et al. |
| 6,887,270 B2 | 5/2005 | Miller et al. |
| 6,908,912 B2 | 6/2005 | Rioux et al. |
| 6,936,447 B1 | 8/2005 | Pearson et al. |
| 6,991,810 B1 | 1/2006 | Grundy et al. |
| 7,018,642 B2 | 3/2006 | Degenhardt et al. |
| 7,025,986 B2 | 4/2006 | Brown et al. |
| 7,052,614 B2 | 5/2006 | Barak |

(Continued)

FOREIGN PATENT DOCUMENTS

| | | |
|---|---|---|
| DE | 2310246 | 9/1974 |
| DE | 2349090 | 4/1975 |

(Continued)

OTHER PUBLICATIONS

Ballatore et al., Carboxylic Acid (Bio)Isosteres in Drug Design, ChemMedChem. Mar. 2013 ; 8(3): 385-395. doi:10.1002/cmdc. 201200585. (Year: 2013).*

(Continued)

*Primary Examiner* — Jennifer A Berrios
(74) *Attorney, Agent, or Firm* — Hoffberg & Associates; Steven M. Hoffberg

(57) ABSTRACT

One aspect of the present invention is directed to a composition. The composition includes a dispersion inducer comprising:

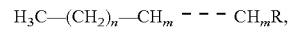

$H_3C—(CH_2)_n—CH_m \text{ --- } CH_mR$, where --- is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains an additive component selected from one or more of the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm. The present invention is also directed to methods of using this compound.

20 Claims, 18 Drawing Sheets

(56) References Cited

U.S. PATENT DOCUMENTS

| | | |
|---|---|---|
| 7,087,661 B1 | 8/2006 | Alberte et al. |
| 7,094,394 B2 | 8/2006 | Davies et al. |
| 7,144,992 B2 | 12/2006 | Madhyastha |
| 7,147,888 B2 | 12/2006 | Brown et al. |
| 7,151,139 B2 | 12/2006 | Tiller et al. |
| 7,189,329 B2 | 3/2007 | Barak |
| 7,189,351 B2 | 3/2007 | Levin et al. |
| 7,201,925 B2 | 4/2007 | Gillis |
| 7,217,425 B2 | 5/2007 | Serhan et al. |
| 7,255,881 B2 | 8/2007 | Gillis et al. |
| 7,314,857 B2 | 1/2008 | Madhyastha |
| 7,399,742 B2 | 7/2008 | DiMauro et al. |
| 7,402,722 B2 | 7/2008 | Hill et al. |
| 7,419,607 B2 | 9/2008 | Downs |
| 7,427,416 B2 | 9/2008 | Gillis et al. |
| 7,446,089 B2 | 11/2008 | Singh et al. |
| 7,450,228 B2 | 11/2008 | Maier et al. |
| 7,452,345 B2 | 11/2008 | Darouiche et al. |
| 7,498,051 B2 | 3/2009 | Man et al. |
| 7,504,123 B2 | 3/2009 | Man et al. |
| 7,534,368 B2 | 5/2009 | Martin |
| 7,556,807 B2 | 7/2009 | Cvitkovitch et al. |
| 7,592,025 B2 | 9/2009 | Dodds et al. |
| 7,601,731 B2 | 10/2009 | Raad |
| 7,612,045 B2 | 11/2009 | Eldridge |
| 7,628,929 B2 | 12/2009 | Barak |
| 7,691,418 B2 | 4/2010 | Rossel |
| 7,713,955 B2 | 5/2010 | Whiteford et al. |
| 7,744,555 B2 | 6/2010 | DiMauro et al. |
| 7,760,353 B2 | 7/2010 | Maier et al. |
| 7,781,166 B2 | 8/2010 | Yu et al. |
| 7,790,947 B2 | 9/2010 | Hill et al. |
| 7,794,698 B2 | 9/2010 | Bukshpan et al. |
| 7,795,000 B2 | 9/2010 | Podtburg et al. |
| 7,820,193 B2 | 10/2010 | Hunter et al. |
| 7,829,305 B2 | 11/2010 | Kolari et al. |
| 7,838,532 B2 | 11/2010 | Surber et al. |
| 7,863,029 B2 | 1/2011 | Jaffe |
| 7,887,641 B2 | 2/2011 | Man et al. |
| 7,897,631 B2 | 3/2011 | Melander et al. |
| 7,906,544 B2 | 3/2011 | Melander et al. |
| 7,923,425 B2 | 4/2011 | Held |
| 7,927,496 B2 | 4/2011 | Barak |
| 7,959,943 B2 | 6/2011 | Hissong et al. |
| 7,976,873 B2 | 7/2011 | Myntti et al. |
| 7,993,390 B2 | 8/2011 | Miller et al. |
| 7,993,675 B2 | 8/2011 | Oliver et al. |
| 7,998,919 B2 | 8/2011 | Rong et al. |
| 8,021,610 B2 | 9/2011 | Code |
| 8,067,402 B2 | 11/2011 | Whiteford et al. |
| 8,067,403 B2 | 11/2011 | Whiteford et al. |
| 8,071,540 B2 | 12/2011 | Montelaro et al. |
| 8,076,117 B2 | 12/2011 | Trampuz et al. |
| 8,105,520 B2 | 1/2012 | Miller et al. |
| 8,128,976 B2 | 3/2012 | Man et al. |
| 8,133,501 B2 | 3/2012 | Li et al. |
| 8,142,764 B2 | 3/2012 | Demuth et al. |
| 8,153,119 B2 | 4/2012 | Collins et al. |
| 8,153,410 B2 | 4/2012 | Jaffe |
| 8,153,412 B2 | 4/2012 | Chang et al. |
| 8,162,924 B2 | 4/2012 | Boyden et al. |
| 8,168,072 B2 | 5/2012 | Barak |
| 8,173,673 B2 | 5/2012 | Bringmann et al. |
| 8,206,740 B2 | 6/2012 | Chang et al. |
| 8,211,361 B2 | 7/2012 | Sun et al. |
| 8,216,173 B2 | 7/2012 | Dacey, Jr. et al. |
| 8,221,480 B2 | 7/2012 | Boyden et al. |
| 8,227,017 B2 | 7/2012 | Leander et al. |
| 8,231,686 B2 | 7/2012 | Mangiardi |
| 8,236,545 B2 | 8/2012 | Cascao-Pereira et al. |
| 8,246,691 B2 | 8/2012 | Mangiardi |
| 8,246,758 B2 | 8/2012 | Man et al. |
| 8,252,550 B2 | 8/2012 | Otto et al. |
| 8,256,233 B2 | 9/2012 | Boyden et al. |
| 8,257,749 B2 | 9/2012 | Code |
| 8,257,827 B1 | 9/2012 | Shi et al. |
| 8,267,883 B2 | 9/2012 | DiMauro et al. |
| 8,268,381 B2 | 9/2012 | Whiteford et al. |
| 8,273,104 B2 | 9/2012 | Cohen |
| 8,278,340 B2 | 10/2012 | Melander et al. |
| 8,282,593 B2 | 10/2012 | Dacey, Jr. et al. |
| 8,282,967 B2 | 10/2012 | Schoenfisch et al. |
| 8,283,135 B2 | 10/2012 | Doyle et al. |
| 8,298,799 B2 | 10/2012 | Bornscheuer et al. |
| 8,309,590 B2 | 11/2012 | Reid |
| 8,318,180 B2 | 11/2012 | Shirtliff et al. |
| 8,329,758 B2 | 12/2012 | Ali et al. |
| 8,343,086 B2 | 1/2013 | Dacey, Jr. et al. |
| 8,343,911 B2 | 1/2013 | Singh et al. |
| 8,349,368 B2 | 1/2013 | Gordon et al. |
| 8,357,696 B2 | 1/2013 | Surber et al. |
| 8,366,652 B2 | 2/2013 | Dacey, Jr. et al. |
| 8,367,713 B2 | 2/2013 | Melander et al. |
| 8,367,716 B2 | 2/2013 | Karaolis |
| 8,367,823 B2 | 2/2013 | Sun et al. |
| 8,377,455 B2 | 2/2013 | Ceri et al. |
| 8,383,101 B2 | 2/2013 | Olmstead |
| 8,383,582 B2 | 2/2013 | Oh et al. |
| 8,389,021 B2 | 3/2013 | Baker |
| 8,389,679 B2 | 3/2013 | Eckert et al. |
| 8,394,405 B2 | 3/2013 | Chang et al. |
| 8,394,406 B2 | 3/2013 | Chang et al. |
| 8,398,705 B2 | 3/2013 | Mangiardi |
| 8,399,235 B2 | 3/2013 | Frank et al. |
| 8,399,649 B2 | 3/2013 | Yu et al. |
| 8,409,376 B2 | 4/2013 | Boyden et al. |
| 8,414,356 B2 | 4/2013 | Boyden et al. |
| 8,414,517 B2 | 4/2013 | Dacey, Jr. et al. |
| 8,415,159 B2 | 4/2013 | Ward et al. |
| 8,420,699 B1 | 4/2013 | Dubow |
| 8,425,880 B1 | 4/2013 | Lyczak et al. |
| 8,431,151 B2 | 4/2013 | Mather et al. |
| 8,444,858 B2 | 5/2013 | Barak |
| 8,454,566 B2 | 6/2013 | Van Antwerp |
| 8,460,229 B2 | 6/2013 | Dacey, Jr. et al. |
| 8,460,916 B2 | 6/2013 | Cascao-Pereira et al. |
| 8,461,106 B2 | 6/2013 | Cohen et al. |
| 8,470,364 B2 | 6/2013 | Chang et al. |
| 8,476,319 B2 | 7/2013 | Scholz et al. |
| 8,476,425 B1 | 7/2013 | Lai et al. |
| 8,481,138 B2 | 7/2013 | Miller et al. |
| 8,485,861 B2 | 7/2013 | Boyden et al. |
| 8,486,428 B2 | 7/2013 | Sun et al. |
| 8,501,969 B2 | 8/2013 | Meijler et al. |
| 8,507,244 B2 | 8/2013 | Shaw et al. |
| 8,513,305 B2 | 8/2013 | Davies |
| 8,518,031 B2 | 8/2013 | Boyden et al. |
| 8,524,734 B2 | 9/2013 | Surber et al. |
| 8,524,735 B2 | 9/2013 | Surber et al. |
| 8,545,806 B2 | 10/2013 | Boyden et al. |
| 8,545,836 B2 | 10/2013 | Kaul et al. |
| 8,545,855 B2 | 10/2013 | Boyden et al. |
| 8,545,856 B2 | 10/2013 | Boyden et al. |
| 8,545,857 B2 | 10/2013 | Boyden et al. |
| 8,545,951 B2 | 10/2013 | Yahiaoui et al. |
| 8,546,121 B2 | 10/2013 | Aehle et al. |
| 8,546,423 B2 | 10/2013 | Surber et al. |
| 8,551,505 B2 | 10/2013 | Boyden et al. |
| 8,551,506 B2 | 10/2013 | Boyden et al. |
| 8,552,147 B2 | 10/2013 | Zlotkin |
| 8,552,208 B2 | 10/2013 | Lee et al. |
| 8,557,551 B2 | 10/2013 | Lam et al. |
| 8,563,012 B2 | 10/2013 | Boyden et al. |
| 8,565,892 B2 | 10/2013 | Nayfach-Battilana |
| 8,567,612 B2 | 10/2013 | Kurth et al. |
| 8,568,363 B2 | 10/2013 | Boyden et al. |
| 8,569,449 B2 | 10/2013 | Gorr |
| 8,574,660 B2 | 11/2013 | Weaver et al. |
| 8,585,627 B2 | 11/2013 | Dacey, Jr. et al. |
| 8,591,876 B2 | 11/2013 | Bauman et al. |
| 8,591,961 B2 | 11/2013 | Widgerow |
| 8,592,473 B2 | 11/2013 | Reid |
| 8,603,494 B2 | 12/2013 | Boyden et al. |
| 8,603,495 B2 | 12/2013 | Boyden et al. |

(56) References Cited

U.S. PATENT DOCUMENTS

| | | |
|---|---|---|
| 8,603,496 B2 | 12/2013 | Boyden et al. |
| 8,604,004 B2 | 12/2013 | Kahne et al. |
| 8,609,110 B2 | 12/2013 | Shanks et al. |
| 8,613,937 B2 | 12/2013 | Boyden et al. |
| 8,617,523 B2 | 12/2013 | Trivedi et al. |
| 8,617,542 B2 | 12/2013 | Madhyastha et al. |
| 8,618,149 B2 | 12/2013 | Melander et al. |
| 8,623,340 B2 | 1/2014 | Kuhn et al. |
| 8,623,371 B2 | 1/2014 | Otto et al. |
| 8,632,838 B2 | 1/2014 | Roth et al. |
| 8,637,090 B2 | 1/2014 | Ohtake et al. |
| 8,641,686 B2 | 2/2014 | Stephan |
| 8,647,292 B2 | 2/2014 | Dacey, Jr. et al. |
| 8,652,829 B2 | 2/2014 | Bellalou et al. |
| 8,653,124 B2 | 2/2014 | Melander et al. |
| 8,658,225 B2 | 2/2014 | Zinreich et al. |
| 8,663,616 B2 | 3/2014 | Butterick et al. |
| 8,680,072 B2 | 3/2014 | Onsoyen et al. |
| 8,680,148 B2 | 3/2014 | Greenberg et al. |
| 8,684,732 B2 | 4/2014 | Jacoby |
| 8,685,427 B2 | 4/2014 | Li et al. |
| 8,685,957 B1 | 4/2014 | Lai et al. |
| 8,691,264 B2 | 4/2014 | Li et al. |
| 8,691,288 B2 | 4/2014 | Myntti |
| 8,697,101 B2 | 4/2014 | Marquais-Bienewald et al. |
| 8,697,102 B2 | 4/2014 | Bukshpan et al. |
| 8,697,375 B2 | 4/2014 | Shirtliff et al. |
| 8,702,640 B2 | 4/2014 | Dacey, Jr. et al. |
| 8,706,211 B2 | 4/2014 | Dacey, Jr. et al. |
| 8,709,342 B2 | 4/2014 | Raad |
| 8,709,478 B2 | 4/2014 | Chang et al. |
| 8,710,082 B2 | 4/2014 | Waters et al. |
| 8,715,733 B2 | 5/2014 | Kadiyala et al. |
| 8,721,583 B2 | 5/2014 | Boyden et al. |
| 8,722,068 B2 | 5/2014 | Boyden et al. |
| 8,725,420 B2 | 5/2014 | Boyden et al. |
| 8,728,467 B2 | 5/2014 | Olmstead |
| 8,731,840 B2 | 5/2014 | Boyden et al. |
| 8,731,841 B2 | 5/2014 | Boyden et al. |
| 8,731,842 B2 | 5/2014 | Boyden et al. |
| 8,734,718 B2 | 5/2014 | Dacey, Jr. et al. |
| 8,741,855 B2 | 6/2014 | Quave et al. |
| 8,748,661 B2 | 6/2014 | Xu et al. |
| 8,753,304 B2 | 6/2014 | Dacey, Jr. et al. |
| 8,753,692 B2 | 6/2014 | Gawande et al. |
| 8,754,039 B2 | 6/2014 | Eckert et al. |
| 8,758,781 B2 | 6/2014 | Ward et al. |
| 8,758,824 B2 | 6/2014 | Lipp et al. |
| 8,762,067 B2 | 6/2014 | Boyden et al. |
| 8,778,370 B2 | 7/2014 | Kramer et al. |
| 8,778,387 B2 | 7/2014 | Tennican et al. |
| 8,778,889 B2 | 7/2014 | Leung |
| 8,779,023 B2 | 7/2014 | Whang et al. |
| 8,784,384 B2 | 7/2014 | Boyden et al. |
| 8,784,385 B2 | 7/2014 | Boyden et al. |
| 8,785,399 B2 | 7/2014 | Giuliani et al. |
| 8,785,680 B2 | 7/2014 | Zhang et al. |
| 8,788,211 B2 | 7/2014 | Boyden et al. |
| 8,788,212 B2 | 7/2014 | Boyden et al. |
| 8,790,684 B2 | 7/2014 | Dave et al. |
| 8,793,075 B2 | 7/2014 | Boyden et al. |
| 8,795,727 B2 | 8/2014 | Gong et al. |
| 8,796,252 B2 | 8/2014 | Rioux et al. |
| 8,798,932 B2 | 8/2014 | Boyden et al. |
| 8,798,933 B2 | 8/2014 | Boyden et al. |
| 8,802,059 B2 | 8/2014 | Fagon et al. |
| 8,802,414 B2 | 8/2014 | Frank et al. |
| 8,808,718 B2 | 8/2014 | Van Der Waal et al. |
| 8,809,031 B2 | 8/2014 | England et al. |
| 8,809,314 B1 | 8/2014 | He et al. |
| 8,821,862 B2 | 9/2014 | Madhyastha et al. |
| 8,821,910 B2 | 9/2014 | Song et al. |
| 8,828,910 B2 | 9/2014 | Aksela et al. |
| 8,829,053 B2 | 9/2014 | Salamone et al. |
| 8,835,644 B2 | 9/2014 | Hoffman et al. |
| 8,840,912 B2 | 9/2014 | Melander et al. |
| 8,846,008 B2 | 9/2014 | Tennican et al. |
| 8,846,009 B2 | 9/2014 | Tennican et al. |
| 8,846,605 B2 | 9/2014 | Ghatnekar |
| 8,849,441 B2 | 9/2014 | Boyden et al. |
| 8,852,912 B2 | 10/2014 | Estell et al. |
| 8,853,278 B1 | 10/2014 | Looper et al. |
| 8,858,912 B2 | 10/2014 | Boyden et al. |
| 8,865,909 B2 | 10/2014 | Srebnik et al. |
| 8,884,022 B2 | 11/2014 | Melander et al. |
| 8,888,731 B2 | 11/2014 | Dacey, Jr. et al. |
| 8,889,196 B2 | 11/2014 | Xu |
| 8,900,624 B2 | 12/2014 | Karandikar et al. |
| 8,906,349 B2 | 12/2014 | Schaeffer-Korbylo et al. |
| 8,906,364 B2 | 12/2014 | Madhyastha |
| 8,906,393 B2 | 12/2014 | Kaplan et al. |
| 8,906,898 B1 | 12/2014 | Hwang et al. |
| 8,906,915 B2 | 12/2014 | De Keersmaecker et al. |
| 8,920,826 B2 | 12/2014 | Bucay-Couto |
| 8,921,071 B2 | 12/2014 | Otto et al. |
| 8,926,951 B2 | 1/2015 | Ratcliff et al. |
| 8,927,029 B2 | 1/2015 | Melander et al. |
| 8,937,167 B2 | 1/2015 | Janetka et al. |
| 8,940,911 B2 | 1/2015 | Luk et al. |
| 8,945,142 B2 | 2/2015 | Schaeffer et al. |
| 8,952,192 B2 | 2/2015 | Sintim et al. |
| 8,956,658 B2 | 2/2015 | Schoenfisch et al. |
| 8,956,663 B2 | 2/2015 | Gordon et al. |
| 8,962,029 B2 | 2/2015 | Schoenfisch et al. |
| 8,962,283 B2 | 2/2015 | Cascao-Pereira et al. |
| 8,968,753 B2 | 3/2015 | Terracciano et al. |
| 8,968,765 B2 | 3/2015 | Chen et al. |
| 8,980,299 B2 | 3/2015 | Dave et al. |
| 8,981,139 B2 | 3/2015 | Schoenfisch et al. |
| 8,992,223 B2 | 3/2015 | Sun et al. |
| 8,992,983 B2 | 3/2015 | Lipp et al. |
| 8,999,175 B2 | 4/2015 | Man et al. |
| 8,999,265 B2 | 4/2015 | Koesdjojo et al. |
| 9,005,263 B2 | 4/2015 | Boyden et al. |
| 9,005,643 B2 | 4/2015 | Melander et al. |
| 9,005,680 B2 | 4/2015 | Fetissova et al. |
| 9,012,505 B2 | 4/2015 | Zhang et al. |
| 9,028,878 B2 | 5/2015 | Baker |
| 9,029,318 B2 | 5/2015 | Zlotkin et al. |
| 9,034,346 B2 | 5/2015 | Miller et al. |
| 9,034,612 B2 | 5/2015 | Lam et al. |
| 9,034,927 B2 | 5/2015 | Williams et al. |
| 9,040,087 B2 | 5/2015 | Boyden et al. |
| 9,044,485 B2 | 6/2015 | Terracciano et al. |
| 9,044,531 B2 | 6/2015 | Dave et al. |
| 9,045,550 B2 | 6/2015 | Zlotkin |
| 9,045,712 B2 | 6/2015 | Dayton et al. |
| 9,050,070 B2 | 6/2015 | Boyden et al. |
| 9,050,251 B2 | 6/2015 | Boyden et al. |
| 9,050,317 B2 | 6/2015 | Boyden et al. |
| 9,056,047 B2 | 6/2015 | Boyden et al. |
| 9,056,899 B2 | 6/2015 | Collins et al. |
| 9,060,926 B2 | 6/2015 | Boyden et al. |
| 9,060,931 B2 | 6/2015 | Boyden et al. |
| 9,060,934 B2 | 6/2015 | Boyden et al. |
| 9,061,352 B2 | 6/2015 | Lipp et al. |
| 9,072,688 B2 | 7/2015 | Boyden et al. |
| 9,072,799 B2 | 7/2015 | Boyden et al. |
| 9,073,884 B2 | 7/2015 | Gerwick et al. |
| 9,078,441 B2 | 7/2015 | Raad |
| 9,084,423 B2 | 7/2015 | Melander et al. |
| 9,084,902 B2 | 7/2015 | Mordas et al. |
| 9,085,608 B2 | 7/2015 | Stensen et al. |
| 9,096,703 B2 | 8/2015 | Li et al. |
| 9,125,408 B2 | 9/2015 | Melander et al. |
| 9,125,853 B2 | 9/2015 | Reynolds |
| 9,131,687 B2 | 9/2015 | Kolter et al. |
| 9,139,622 B2 | 9/2015 | Shanks et al. |
| 9,145,395 B2 | 9/2015 | Melander et al. |
| 9,149,648 B2 | 10/2015 | Dacey, Jr. et al. |
| 9,150,453 B1 | 10/2015 | Li et al. |
| 9,150,788 B2 | 10/2015 | Luk et al. |
| 9,155,310 B2 | 10/2015 | Agrawal et al. |
| 9,156,855 B2 | 10/2015 | Barraud et al. |

(56) References Cited

U.S. PATENT DOCUMENTS

| | | |
|---|---|---|
| 9,161,544 B2 | 10/2015 | Agrawal et al. |
| 9,161,923 B2 | 10/2015 | Holden |
| 9,161,984 B2 | 10/2015 | Ghatnekar |
| 9,167,820 B2 | 10/2015 | Demuth et al. |
| 9,169,319 B2 | 10/2015 | Alarcon et al. |
| 9,180,157 B2 | 11/2015 | Widgerow |
| 9,180,158 B2 | 11/2015 | Widgerow |
| 9,181,290 B2 | 11/2015 | Liu et al. |
| 9,187,501 B2 | 11/2015 | Schoenfisch et al. |
| 9,193,767 B2 | 11/2015 | Sello |
| 9,193,962 B2 | 11/2015 | Bornscheuer et al. |
| 9,198,957 B2 | 12/2015 | Ratner et al. |
| 9,212,286 B2 | 12/2015 | Whiteford et al. |
| 9,220,267 B2 | 12/2015 | Williams et al. |
| 9,221,213 B2 | 12/2015 | Dou et al. |
| 9,221,765 B2 | 12/2015 | Melander et al. |
| 9,221,875 B2 | 12/2015 | Yang et al. |
| 9,227,980 B2 | 1/2016 | Scherman et al. |
| 9,233,158 B2 | 1/2016 | Lipp et al. |
| 9,242,951 B2 | 1/2016 | Meijler et al. |
| 9,243,036 B2 | 1/2016 | Atreya et al. |
| 9,243,267 B2 | 1/2016 | Lam et al. |
| 9,247,734 B2 | 2/2016 | Sabin |
| 9,253,987 B2 | 2/2016 | Tennican et al. |
| 9,265,820 B2 | 2/2016 | Shirtliff et al. |
| 9,271,493 B2 | 3/2016 | Cegelski et al. |
| 9,271,502 B2 | 3/2016 | Sabin |
| 9,273,084 B2 | 3/2016 | Kahne et al. |
| 9,273,096 B2 | 3/2016 | Yang et al. |
| 9,283,280 B2 | 3/2016 | Maggio |
| 9,283,283 B2 | 3/2016 | Giammona et al. |
| 9,284,351 B2 | 3/2016 | Zlotkin |
| 9,289,442 B2 | 3/2016 | Doxey et al. |
| 9,289,449 B2 | 3/2016 | Sershen et al. |
| 9,295,257 B2 | 3/2016 | Melander et al. |
| 9,308,298 B2 | 4/2016 | Zhang |
| 9,320,740 B2 | 4/2016 | Terracciano et al. |
| 9,321,030 B2 | 4/2016 | Sukhishvili et al. |
| 9,326,511 B2 | 5/2016 | Love et al. |
| 9,326,924 B1 | 5/2016 | Fourre et al. |
| 9,326,925 B1 | 5/2016 | Fourre et al. |
| 9,334,466 B2 | 5/2016 | Aehle et al. |
| 9,339,525 B2 | 5/2016 | O'Neil et al. |
| 9,340,802 B2 | 5/2016 | Trevethick |
| 9,351,491 B2 | 5/2016 | Melander et al. |
| 9,351,492 B2 | 5/2016 | Quave et al. |
| 9,358,274 B2 | 6/2016 | Olmstead |
| 9,359,275 B2 | 6/2016 | Watnick et al. |
| 9,364,491 B2 | 6/2016 | O'Neil et al. |
| 9,370,187 B2 | 6/2016 | Reid et al. |
| 9,376,430 B2 | 6/2016 | Hoffman et al. |
| 9,387,189 B2 | 7/2016 | Glasnapp |
| 9,393,261 B2 | 7/2016 | Sternoff et al. |
| 9,394,529 B2 | 7/2016 | Barton et al. |
| 9,402,394 B2 | 8/2016 | Tang et al. |
| 9,403,851 B2 | 8/2016 | Schoenfisch et al. |
| 9,403,852 B2 | 8/2016 | Schoenfisch et al. |
| 9,408,393 B2 | 8/2016 | Baker |
| 9,415,144 B2 | 8/2016 | Anzai et al. |
| 9,423,532 B2 | 8/2016 | Jewhurst et al. |
| 9,427,605 B2 | 8/2016 | Peters |
| 9,433,527 B2 | 9/2016 | Varga et al. |
| 9,433,576 B2 | 9/2016 | Lipp et al. |
| 9,439,433 B2 | 9/2016 | Looper et al. |
| 9,439,436 B2 | 9/2016 | Melander et al. |
| 9,439,803 B2 | 9/2016 | Varga et al. |
| 9,446,090 B2 | 9/2016 | Bevilacqua et al. |
| 9,452,107 B2 | 9/2016 | Bilgili et al. |
| 9,469,616 B2 | 10/2016 | Li et al. |
| 9,469,861 B2 | 10/2016 | Blake et al. |
| 9,474,831 B2 | 10/2016 | Boyden et al. |
| 9,480,260 B2 | 11/2016 | Whang et al. |
| 9,480,541 B2 | 11/2016 | Falcone et al. |
| 9,487,453 B2 | 11/2016 | Sabin |
| 9,492,596 B2 | 11/2016 | Herweck et al. |
| 9,499,419 B2 | 11/2016 | de Rijk |
| 9,499,594 B2 | 11/2016 | Schuch et al. |
| 9,499,844 B2 | 11/2016 | Lam et al. |
| 9,504,688 B2 | 11/2016 | Ginsburg et al. |
| 9,504,739 B2 | 11/2016 | Berkes et al. |
| 9,512,382 B2 | 12/2016 | Dayton et al. |
| 9,518,013 B2 | 12/2016 | Li et al. |
| 9,526,738 B2 | 12/2016 | Stasko et al. |
| 9,526,766 B2 | 12/2016 | Hakansson et al. |
| 9,539,233 B2 | 1/2017 | Ohtake et al. |
| 9,539,367 B2 | 1/2017 | Britigan et al. |
| 9,539,373 B2 | 1/2017 | Jones et al. |
| 9,540,389 B2 | 1/2017 | Opperman et al. |
| 9,540,471 B2 | 1/2017 | Hrabie et al. |
| 9,550,005 B2 | 1/2017 | Lin et al. |
| 9,554,971 B2 | 1/2017 | Xu et al. |
| 9,555,116 B2 | 1/2017 | Folan |
| 9,556,109 B1 | 1/2017 | Caran et al. |
| 9,556,223 B2 | 1/2017 | Stensen et al. |
| 9,561,168 B2 | 2/2017 | Schaeffer-Korbylo et al. |
| 9,562,085 B2 | 2/2017 | Nibbering et al. |
| 9,562,254 B2 | 2/2017 | Potnis et al. |
| 9,565,857 B2 | 2/2017 | Raad et al. |
| 9,566,247 B2 | 2/2017 | Koo et al. |
| 9,566,341 B1 | 2/2017 | Stinchcomb et al. |
| 9,566,372 B2 | 2/2017 | Handa et al. |
| 9,567,362 B2 | 2/2017 | Janetka et al. |
| 9,574,185 B2 | 2/2017 | Yim et al. |
| 9,574,189 B2 | 2/2017 | Franch et al. |
| 9,585,922 B2 | 3/2017 | Lang et al. |
| 9,586,871 B2 | 3/2017 | Sabin |
| 9,591,852 B2 | 3/2017 | Mordas et al. |
| 9,592,299 B2 | 3/2017 | Sershen et al. |
| 9,592,324 B2 | 3/2017 | Herweck et al. |
| 9,597,407 B2 | 3/2017 | Eckert et al. |
| 9,603,859 B2 | 3/2017 | Genberg et al. |
| 9,603,877 B2 | 3/2017 | Chang et al. |
| 9,603,977 B2 | 3/2017 | Ghigo et al. |
| 9,603,979 B2 | 3/2017 | Ghigo et al. |
| 9,612,246 B2 | 4/2017 | Bruce et al. |
| 9,617,176 B2 | 4/2017 | Cuero Rengifo et al. |
| 9,622,481 B2 | 4/2017 | Gawande et al. |
| 9,631,100 B2 | 4/2017 | Reches |
| 9,642,798 B2 | 5/2017 | Lipp et al. |
| 9,642,829 B2 | 5/2017 | Seneviratne et al. |
| 9,644,194 B2 | 5/2017 | Yim et al. |
| 9,648,876 B2 | 5/2017 | Jackson et al. |
| 9,648,880 B2 | 5/2017 | Kaufman et al. |
| 9,657,132 B2 | 5/2017 | Hanson et al. |
| 9,669,001 B2 | 6/2017 | Bowler et al. |
| 9,669,041 B2 | 6/2017 | Stasko et al. |
| 9,675,077 B2 | 6/2017 | Parsons |
| 9,675,736 B2 | 6/2017 | Burgess et al. |
| 9,682,023 B2 | 6/2017 | Ratcliff et al. |
| 9,683,197 B2 | 6/2017 | Aizenberg et al. |
| 9,687,001 B2 | 6/2017 | Vujanovic et al. |
| 9,687,670 B2 | 6/2017 | Dacey, Jr. et al. |
| 9,694,114 B2 | 7/2017 | Lucchino et al. |
| 9,700,058 B2 | 7/2017 | Zlotkin |
| 9,700,650 B2 | 7/2017 | Gong et al. |
| 9,706,778 B2 | 7/2017 | Berkes et al. |
| 9,713,631 B2 | 7/2017 | Berkes et al. |
| 9,713,652 B2 | 7/2017 | Schoenfisch et al. |
| 9,717,251 B2 | 8/2017 | Sabin |
| 9,717,765 B2 | 8/2017 | Berkes et al. |
| 9,718,739 B2 | 8/2017 | Sabin |
| 9,723,833 B2 | 8/2017 | Kolari et al. |
| 9,723,837 B2 | 8/2017 | Melander et al. |
| 9,723,843 B2 | 8/2017 | Olson et al. |
| 9,724,353 B2 | 8/2017 | Chandorkar et al. |
| 9,732,124 B2 | 8/2017 | Zlotkin |
| 9,737,561 B2 | 8/2017 | Stasko et al. |
| 9,737,571 B2 | 8/2017 | Zlotkin et al. |
| 9,737,591 B2 | 8/2017 | Olmstead |
| 9,744,130 B2 | 8/2017 | Lipp et al. |
| 9,744,270 B2 | 8/2017 | Boluk et al. |
| 9,746,407 B2 | 8/2017 | Bernardi et al. |
| 9,757,397 B2 | 9/2017 | Kougoulos et al. |
| 9,764,069 B2 | 9/2017 | Roth et al. |

(56) References Cited

U.S. PATENT DOCUMENTS

| | | |
|---|---|---|
| 9,770,418 B2 | 9/2017 | Rahimipour et al. |
| 9,775,853 B2 | 10/2017 | Troxel et al. |
| 9,777,050 B2 | 10/2017 | Zlotkin et al. |
| 9,782,388 B2 | 10/2017 | Shaw et al. |
| 9,782,423 B2 | 10/2017 | O'Neil et al. |
| 9,789,005 B2 | 10/2017 | Tennican et al. |
| 9,789,057 B2 | 10/2017 | Riley et al. |
| 9,795,762 B2 | 10/2017 | Bouchard et al. |
| 9,801,982 B2 | 10/2017 | Herweck et al. |
| 9,808,496 B2 | 11/2017 | Luc et al. |
| 9,814,719 B2 | 11/2017 | Sun et al. |
| 9,815,794 B2 | 11/2017 | Melander et al. |
| 9,833,528 B2 | 12/2017 | Alarcon et al. |
| 9,834,744 B2 | 12/2017 | Ludwig et al. |
| 9,839,219 B2 | 12/2017 | Looper et al. |
| 9,844,679 B2 | 12/2017 | Nayfach-Battilana |
| 9,849,182 B2 | 12/2017 | McInroy et al. |
| 9,850,322 B2 | 12/2017 | Schoenfisch et al. |
| 9,854,807 B2 | 1/2018 | Sabin |
| 9,855,211 B2 | 1/2018 | Doxey et al. |
| 9,856,225 B2 | 1/2018 | Huigens, III et al. |
| 9,856,283 B2 | 1/2018 | Oscarson et al. |
| 9,861,701 B2 | 1/2018 | Sershen et al. |
| 9,861,723 B2 | 1/2018 | Hanson et al. |
| 9,862,837 B2 | 1/2018 | Reches |
| 9,867,906 B2 | 1/2018 | Matheny |
| 9,872,491 B2 | 1/2018 | Gambogi et al. |
| 9,872,893 B2 | 1/2018 | Nelson |
| 9,872,906 B2 | 1/2018 | Terracciano et al. |
| 9,872,917 B2 | 1/2018 | Tang et al. |
| 9,877,983 B2 | 1/2018 | Onsoyen et al. |
| 9,888,691 B2 | 2/2018 | Karandikar et al. |
| 9,889,077 B2 | 2/2018 | Schaeffer-Korbylo et al. |
| 9,895,469 B2 | 2/2018 | Schultz et al. |
| 9,907,584 B2 | 3/2018 | Mangiardi |
| 9,913,476 B2 | 3/2018 | Agrawal et al. |
| 9,914,750 B2 | 3/2018 | Gorr |
| 9,918,473 B2 | 3/2018 | Melander et al. |
| 9,919,012 B2 | 3/2018 | Berkes et al. |
| 9,919,072 B2 | 3/2018 | Stasko et al. |
| 9,919,079 B2 | 3/2018 | Matheny |
| 9,925,205 B2 | 3/2018 | Malinin |
| 9,926,526 B2 | 3/2018 | Newman et al. |
| 9,931,300 B2 | 4/2018 | Bilgili et al. |
| 9,931,381 B2 | 4/2018 | Olmstead |
| 9,932,484 B2 | 4/2018 | Aizenberg et al. |
| 9,937,104 B2 | 4/2018 | Xu et al. |
| 9,956,319 B2 | 5/2018 | Mansouri et al. |
| 9,956,322 B2 | 5/2018 | Pichler-Wilhelm et al. |
| 9,957,289 B2 | 5/2018 | Janetka et al. |
| 9,957,395 B2 | 5/2018 | Whiteford et al. |
| 9,975,857 B2 | 5/2018 | Melander et al. |
| 9,993,533 B2 | 6/2018 | Pellico |
| 10,004,771 B2 | 6/2018 | Berkes et al. |
| 10,016,525 B2 | 7/2018 | Adams et al. |
| 10,034,478 B2 | 7/2018 | Krasnow et al. |
| 10,071,103 B2 | 9/2018 | Sengupta et al. |
| 10,072,161 B2 | 9/2018 | Margel et al. |
| 10,086,025 B2 | 10/2018 | Berkes et al. |
| 10,104,862 B2 | 10/2018 | Vujanovic et al. |
| 10,106,580 B2 | 10/2018 | Sello |
| 10,172,362 B2 | 1/2019 | Wood et al. |
| 10,208,241 B2 | 2/2019 | Agrawal et al. |
| 10,221,398 B2 | 3/2019 | Cady et al. |
| 10,266,793 B2 | 4/2019 | Labib et al. |
| 10,273,260 B2 | 4/2019 | Janetka et al. |
| 10,287,576 B2 | 5/2019 | Franch et al. |
| 10,301,254 B2 | 5/2019 | Wuest et al. |
| 10,308,920 B2 | 6/2019 | Bornscheuer et al. |
| 10,329,549 B2 | 6/2019 | Steer et al. |
| 10,342,849 B2 | 7/2019 | Glasnapp |
| 10,350,217 B2 | 7/2019 | Kaufman et al. |
| 10,376,465 B2 | 8/2019 | Lipp et al. |
| 10,376,538 B2 | 8/2019 | Stasko et al. |
| 10,440,955 B2 | 10/2019 | Looper et al. |
| 10,487,316 B2 | 11/2019 | Barton et al. |
| 10,500,140 B2 | 12/2019 | Wellings |
| 10,508,136 B2 | 12/2019 | Zlotkin |
| 10,513,671 B2 | 12/2019 | Lant et al. |
| 10,526,359 B2 | 1/2020 | Oscarson et al. |
| 10,538,730 B2 | 1/2020 | Nguyen et al. |
| 10,570,364 B2 | 2/2020 | Nguyen et al. |
| 10,570,401 B2 | 2/2020 | Rickard et al. |
| 10,577,743 B2 | 3/2020 | van Buskirk |
| 10,589,039 B2 | 3/2020 | DeHaan et al. |
| 10,597,314 B2 | 3/2020 | Frail et al. |
| 10,611,656 B2 | 4/2020 | Buschmann |
| 10,653,140 B2 | 5/2020 | Davies |
| 10,681,914 B2 | 6/2020 | Dale et al. |
| 10,687,535 B2 | 6/2020 | Wingfield |
| 10,689,610 B2 | 6/2020 | Nguyen et al. |
| 10,711,253 B2 | 7/2020 | Cady et al. |
| 10,723,976 B2 | 7/2020 | Lant et al. |
| 10,738,200 B2 | 8/2020 | Margel et al. |
| 10,806,871 B2 | 10/2020 | DeHaan et al. |
| 10,835,510 B2 | 11/2020 | Baker et al. |
| 10,835,556 B2 | 11/2020 | Pesavento |
| 10,837,004 B2 | 11/2020 | Cady et al. |
| 10,849,324 B2 | 12/2020 | Sawyer et al. |
| 10,849,729 B2 | 12/2020 | Sagel et al. |
| 2002/0066702 A1 | 6/2002 | Liu |
| 2002/0123077 A1 | 9/2002 | O'Toole et al. |
| 2003/0035779 A1 | 2/2003 | Brown et al. |
| 2003/0065292 A1 | 4/2003 | Darouiche et al. |
| 2003/0079758 A1 | 5/2003 | Siegel et al. |
| 2003/0091641 A1 | 5/2003 | Tiller et al. |
| 2003/0099602 A1 | 5/2003 | Levin et al. |
| 2003/0103912 A1 | 6/2003 | Levin et al. |
| 2003/0111420 A1 | 6/2003 | Dresty, Jr. et al. |
| 2003/0121868 A1 | 7/2003 | Barak |
| 2003/0129144 A1 | 7/2003 | Scott et al. |
| 2003/0134783 A1 | 7/2003 | Harshey et al. |
| 2003/0153059 A1 | 8/2003 | Pilkington et al. |
| 2003/0178044 A1 | 9/2003 | Brown et al. |
| 2004/0083556 A1* | 5/2004 | Kurauchi ............ D06M 13/342 8/196 |
| 2004/0097402 A1 | 5/2004 | Bassler et al. |
| 2004/0110738 A1 | 6/2004 | Gillis et al. |
| 2004/0116371 A1 | 6/2004 | Romeo et al. |
| 2004/0116845 A1 | 6/2004 | Darouiche et al. |
| 2004/0129112 A1 | 7/2004 | Gillis et al. |
| 2004/0131698 A1 | 7/2004 | Gillis et al. |
| 2004/0156883 A1 | 8/2004 | Brown et al. |
| 2004/0156884 A1 | 8/2004 | Brown et al. |
| 2004/0176312 A1 | 9/2004 | Gillis |
| 2004/0191329 A1 | 9/2004 | Burrell et al. |
| 2004/0235914 A1 | 11/2004 | Ammendola et al. |
| 2004/0241107 A1 | 12/2004 | Burzynski et al. |
| 2004/0254545 A1 | 12/2004 | Rider et al. |
| 2005/0003725 A1 | 1/2005 | Hill et al. |
| 2005/0008671 A1 | 1/2005 | Van Antwerp |
| 2005/0013836 A1 | 1/2005 | Raad |
| 2005/0032093 A1 | 2/2005 | Romeo et al. |
| 2005/0049181 A1 | 3/2005 | Madhyastha |
| 2005/0064019 A1 | 3/2005 | Hill et al. |
| 2005/0084545 A1 | 4/2005 | Pipko et al. |
| 2005/0095245 A1 | 5/2005 | Riley et al. |
| 2005/0143286 A1 | 6/2005 | Singh et al. |
| 2005/0147719 A1 | 7/2005 | Hill et al. |
| 2005/0151117 A1 | 7/2005 | Man et al. |
| 2005/0158263 A1 | 7/2005 | Rioux et al. |
| 2005/0159324 A1 | 7/2005 | Man et al. |
| 2005/0161636 A1 | 7/2005 | Man et al. |
| 2005/0163896 A1 | 7/2005 | Man et al. |
| 2005/0202424 A1 | 9/2005 | Ausubel et al. |
| 2005/0233950 A1 | 10/2005 | Madhyastha |
| 2005/0249695 A1 | 11/2005 | Tiller et al. |
| 2005/0260181 A1 | 11/2005 | Girsh |
| 2006/0001865 A1 | 1/2006 | Bellalou et al. |
| 2006/0018945 A1 | 1/2006 | Britigan et al. |
| 2006/0034782 A1 | 2/2006 | Brown et al. |
| 2006/0067951 A1 | 3/2006 | Cvitkovitch et al. |
| 2006/0099579 A1 | 5/2006 | Hillman |
| 2006/0110456 A1 | 5/2006 | Teo et al. |

(56) References Cited

U.S. PATENT DOCUMENTS

| | | |
|---|---|---|
| 2006/0113506 A1 | 6/2006 | Man et al. |
| 2006/0120916 A1 | 6/2006 | Kolari et al. |
| 2006/0138058 A1 | 6/2006 | Barak |
| 2006/0162014 A1 | 7/2006 | Jaffe |
| 2006/0165648 A1 | 7/2006 | Degenhardt et al. |
| 2006/0177384 A1 | 8/2006 | Brown |
| 2006/0177490 A1 | 8/2006 | Massouda |
| 2006/0180552 A1 | 8/2006 | Downs |
| 2006/0197058 A1 | 9/2006 | Martin |
| 2006/0224103 A1 | 10/2006 | Rontal |
| 2006/0243297 A1 | 11/2006 | Brown |
| 2006/0264497 A1 | 11/2006 | Zeligs |
| 2006/0276483 A1 | 12/2006 | Surber et al. |
| 2007/0003603 A1 | 1/2007 | Karandikar et al. |
| 2007/0009566 A1 | 1/2007 | Balaban |
| 2007/0010856 A1 | 1/2007 | Cohen |
| 2007/0014739 A1 | 1/2007 | Eldridge et al. |
| 2007/0020309 A1 | 1/2007 | Alberte et al. |
| 2007/0049641 A1 | 3/2007 | Tirouvanziam et al. |
| 2007/0053849 A1 | 3/2007 | Doyle et al. |
| 2007/0062884 A1 | 3/2007 | Sun et al. |
| 2007/0083156 A1 | 4/2007 | Muto et al. |
| 2007/0083677 A1 | 4/2007 | Cecka et al. |
| 2007/0098651 A1 | 5/2007 | Leung |
| 2007/0098674 A1 | 5/2007 | Bukshpan et al. |
| 2007/0098745 A1 | 5/2007 | Bruno |
| 2007/0106232 A1 | 5/2007 | Rider II et al. |
| 2007/0109535 A1 | 5/2007 | Maier et al. |
| 2007/0116750 A1 | 5/2007 | Wolcott |
| 2007/0116798 A1 | 5/2007 | Brown et al. |
| 2007/0134171 A1 | 6/2007 | Dodds et al. |
| 2007/0134649 A1 | 6/2007 | Kolari et al. |
| 2007/0140990 A1 | 6/2007 | Fetissova et al. |
| 2007/0190090 A1 | 8/2007 | Brown |
| 2007/0202342 A1 | 8/2007 | Whiteford et al. |
| 2007/0202566 A1 | 8/2007 | Bornscheuer et al. |
| 2007/0202770 A1 | 8/2007 | Penalva |
| 2007/0207095 A1 | 9/2007 | Davies |
| 2007/0224161 A1 | 9/2007 | Sun et al. |
| 2007/0231406 A1 | 10/2007 | Bucalo et al. |
| 2007/0232167 A1 | 10/2007 | Hill et al. |
| 2007/0244059 A1 | 10/2007 | Karaolis |
| 2007/0253919 A1 | 11/2007 | Boyd |
| 2007/0258913 A1 | 11/2007 | Rossel |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2008/0014247 A1 | 1/2008 | Lu et al. |
| 2008/0014278 A1 | 1/2008 | Lu et al. |
| 2008/0014286 A1 | 1/2008 | Gillis et al. |
| 2008/0020127 A1 | 1/2008 | Whiteford et al. |
| 2008/0021212 A1 | 1/2008 | Whiteford et al. |
| 2008/0044491 A1 | 2/2008 | Lyczak et al. |
| 2008/0045439 A1 | 2/2008 | Held |
| 2008/0050452 A1 | 2/2008 | Chen et al. |
| 2008/0075730 A1 | 3/2008 | Storey et al. |
| 2008/0085282 A1 | 4/2008 | Yu et al. |
| 2008/0085866 A1 | 4/2008 | Greenberg et al. |
| 2008/0095812 A1 | 4/2008 | Code |
| 2008/0107707 A1 | 5/2008 | Lawson et al. |
| 2008/0109017 A1 | 5/2008 | Herweck et al. |
| 2008/0113001 A1 | 5/2008 | Herweck et al. |
| 2008/0138634 A1 | 6/2008 | Morris et al. |
| 2008/0181923 A1 | 7/2008 | Melander et al. |
| 2008/0193562 A1 | 8/2008 | Code |
| 2008/0206183 A1 | 8/2008 | Commeyras et al. |
| 2008/0206276 A1 | 8/2008 | Otto et al. |
| 2008/0206305 A1 | 8/2008 | Herweck et al. |
| 2008/0207581 A1 | 8/2008 | Whiteford et al. |
| 2008/0237028 A1 | 10/2008 | Kislev |
| 2008/0248087 A1 | 10/2008 | Hill et al. |
| 2008/0253976 A1 | 10/2008 | Scott et al. |
| 2008/0268189 A1 | 10/2008 | Sun et al. |
| 2008/0286847 A1 | 11/2008 | Jaffe |
| 2008/0293607 A1 | 11/2008 | Jones et al. |
| 2008/0305531 A1 | 12/2008 | Lam et al. |
| 2008/0317815 A1 | 12/2008 | Davies |
| 2008/0318268 A1 | 12/2008 | Olson et al. |
| 2008/0318269 A1 | 12/2008 | Olson et al. |
| 2009/0005339 A1 | 1/2009 | Scholz et al. |
| 2009/0033930 A1 | 2/2009 | Maier et al. |
| 2009/0048324 A1 | 2/2009 | Jaffe |
| 2009/0050575 A1 | 2/2009 | Barak |
| 2009/0069406 A1 | 3/2009 | Lee et al. |
| 2009/0074825 A1 | 3/2009 | Sun et al. |
| 2009/0099533 A1 | 4/2009 | Montelaro et al. |
| 2009/0112186 A1 | 4/2009 | Adams |
| 2009/0133810 A1 | 5/2009 | Penalva |
| 2009/0143230 A1 | 6/2009 | Melander et al. |
| 2009/0145859 A1 | 6/2009 | Man et al. |
| 2009/0148342 A1 | 6/2009 | Bromberg et al. |
| 2009/0148492 A1 | 6/2009 | Dave et al. |
| 2009/0155215 A1 | 6/2009 | Collins et al. |
| 2009/0163964 A1 | 6/2009 | Boyden et al. |
| 2009/0163965 A1 | 6/2009 | Boyden et al. |
| 2009/0163977 A1 | 6/2009 | Boyden et al. |
| 2009/0171263 A1 | 7/2009 | Boyden et al. |
| 2009/0171388 A1 | 7/2009 | Dave et al. |
| 2009/0177139 A1 | 7/2009 | Boyden et al. |
| 2009/0177254 A1 | 7/2009 | Boyden et al. |
| 2009/0181106 A1 | 7/2009 | Gordon et al. |
| 2009/0192227 A1 | 7/2009 | Tirouvanziam et al. |
| 2009/0202454 A1 | 8/2009 | Prencipe et al. |
| 2009/0202516 A1 | 8/2009 | Olmstead |
| 2009/0214603 A1 | 8/2009 | Demuth et al. |
| 2009/0214628 A1 | 8/2009 | de Rijk |
| 2009/0221704 A1 | 9/2009 | Aksela et al. |
| 2009/0226541 A1 | 9/2009 | Scholz et al. |
| 2009/0238811 A1 | 9/2009 | McDaniel et al. |
| 2009/0238923 A1 | 9/2009 | Shaw et al. |
| 2009/0247422 A1 | 10/2009 | Hillman |
| 2009/0253613 A1 | 10/2009 | Gabbai |
| 2009/0260632 A1 | 10/2009 | Abnousi et al. |
| 2009/0263438 A1 | 10/2009 | Melander et al. |
| 2009/0264300 A1 | 10/2009 | Franch et al. |
| 2009/0269323 A1 | 10/2009 | Luk et al. |
| 2009/0270475 A1 | 10/2009 | Melander et al. |
| 2009/0297495 A1 | 12/2009 | Kerovuo et al. |
| 2009/0318382 A1 | 12/2009 | Ghigo et al. |
| 2009/0324574 A1 | 12/2009 | Mathur et al. |
| 2009/0324820 A1 | 12/2009 | Chartier |
| 2010/0015245 A1 | 1/2010 | Harrison et al. |
| 2010/0016767 A1 | 1/2010 | Jones et al. |
| 2010/0021587 A1 | 1/2010 | Chang et al. |
| 2010/0028396 A1 | 2/2010 | Ward et al. |
| 2010/0037890 A1 | 2/2010 | Surber et al. |
| 2010/0040560 A1 | 2/2010 | Surber et al. |
| 2010/0048446 A1 | 2/2010 | Cascao-Pereira et al. |
| 2010/0055086 A1 | 3/2010 | Raad |
| 2010/0056415 A1 | 3/2010 | Rong et al. |
| 2010/0059433 A1 | 3/2010 | Freeman et al. |
| 2010/0087530 A1 | 4/2010 | Man et al. |
| 2010/0096340 A1 | 4/2010 | Barak |
| 2010/0099599 A1 | 4/2010 | Michalow et al. |
| 2010/0111830 A1 | 5/2010 | Boyden et al. |
| 2010/0111831 A1 | 5/2010 | Boyden et al. |
| 2010/0111832 A1 | 5/2010 | Boyden et al. |
| 2010/0111833 A1 | 5/2010 | Boyden et al. |
| 2010/0111834 A1 | 5/2010 | Boyden et al. |
| 2010/0111835 A1 | 5/2010 | Boyden et al. |
| 2010/0111836 A1 | 5/2010 | Boyden et al. |
| 2010/0111837 A1 | 5/2010 | Boyden et al. |
| 2010/0111841 A1 | 5/2010 | Boyden et al. |
| 2010/0111842 A1 | 5/2010 | Boyden et al. |
| 2010/0111843 A1 | 5/2010 | Boyden et al. |
| 2010/0111844 A1 | 5/2010 | Boyden et al. |
| 2010/0111845 A1 | 5/2010 | Boyden et al. |
| 2010/0111846 A1 | 5/2010 | Boyden et al. |
| 2010/0111847 A1 | 5/2010 | Boyden et al. |
| 2010/0111848 A1 | 5/2010 | Boyden et al. |
| 2010/0111849 A1 | 5/2010 | Boyden et al. |
| 2010/0111850 A1 | 5/2010 | Boyden et al. |
| 2010/0111854 A1 | 5/2010 | Boyden et al. |
| 2010/0111855 A1 | 5/2010 | Boyden et al. |

(56) References Cited

U.S. PATENT DOCUMENTS

| | | |
|---|---|---|
| 2010/0111857 A1 | 5/2010 | Boyden et al. |
| 2010/0111938 A1 | 5/2010 | Boyden et al. |
| 2010/0112067 A1 | 5/2010 | Boyden et al. |
| 2010/0112068 A1 | 5/2010 | Boyden et al. |
| 2010/0112093 A1 | 5/2010 | Boyden et al. |
| 2010/0113614 A1 | 5/2010 | Boyden et al. |
| 2010/0113615 A1 | 5/2010 | Boyden et al. |
| 2010/0114013 A1 | 5/2010 | Boyden et al. |
| 2010/0114267 A1 | 5/2010 | Boyden et al. |
| 2010/0114268 A1 | 5/2010 | Boyden et al. |
| 2010/0114348 A1 | 5/2010 | Boyden et al. |
| 2010/0114496 A1 | 5/2010 | Boyden et al. |
| 2010/0114497 A1 | 5/2010 | Boyden et al. |
| 2010/0114545 A1 | 5/2010 | Boyden et al. |
| 2010/0114546 A1 | 5/2010 | Boyden et al. |
| 2010/0114547 A1 | 5/2010 | Boyden et al. |
| 2010/0114592 A1 | 5/2010 | Boyden et al. |
| 2010/0119557 A1 | 5/2010 | Boyden et al. |
| 2010/0121466 A1 | 5/2010 | Boyden et al. |
| 2010/0129297 A1 | 5/2010 | Vezin |
| 2010/0129466 A1 | 5/2010 | Marques et al. |
| 2010/0130450 A1 | 5/2010 | Lewis et al. |
| 2010/0133114 A1 | 6/2010 | Bukshpan et al. |
| 2010/0136072 A1 | 6/2010 | Haidar et al. |
| 2010/0136112 A1 | 6/2010 | Martin |
| 2010/0136143 A1 | 6/2010 | Bukshpan |
| 2010/0143243 A1 | 6/2010 | Boyden et al. |
| 2010/0145412 A1 | 6/2010 | Boyden et al. |
| 2010/0152101 A1 | 6/2010 | Reid |
| 2010/0152651 A1 | 6/2010 | Boyden et al. |
| 2010/0152880 A1 | 6/2010 | Boyden et al. |
| 2010/0158957 A1 | 6/2010 | Surber et al. |
| 2010/0158966 A1 | 6/2010 | Reid et al. |
| 2010/0158967 A1 | 6/2010 | Reid et al. |
| 2010/0163576 A1 | 7/2010 | Boyden et al. |
| 2010/0166673 A1 | 7/2010 | Surber et al. |
| 2010/0168900 A1 | 7/2010 | Boyden et al. |
| 2010/0173366 A1 | 7/2010 | Rhimi et al. |
| 2010/0174346 A1 | 7/2010 | Boyden et al. |
| 2010/0178268 A1 | 7/2010 | Bukshpan et al. |
| 2010/0183693 A1 | 7/2010 | Martin |
| 2010/0183738 A1 | 7/2010 | Kramer et al. |
| 2010/0185174 A1 | 7/2010 | Boyden et al. |
| 2010/0187728 A1 | 7/2010 | Boyden et al. |
| 2010/0189706 A1 | 7/2010 | Chang et al. |
| 2010/0210745 A1 | 8/2010 | McDaniel et al. |
| 2010/0221198 A1 | 9/2010 | Ratcliff et al. |
| 2010/0233146 A1 | 9/2010 | McDaniel |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241049 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0241054 A1 | 9/2010 | Dacey, Jr. et al. |
| 2010/0241055 A1 | 9/2010 | Dacey, Jr. et al. |
| 2010/0247374 A1 | 9/2010 | Pellet |
| 2010/0249692 A1 | 9/2010 | Dacey, Jr. et al. |
| 2010/0254967 A1 | 10/2010 | Frank et al. |
| 2010/0255178 A1 | 10/2010 | Leander et al. |
| 2010/0266716 A1 | 10/2010 | Olson et al. |
| 2010/0269731 A1 | 10/2010 | Tofte Jespersen et al. |
| 2010/0272768 A1 | 10/2010 | Bukshpan et al. |
| 2010/0286198 A1 | 11/2010 | Bringmann et al. |
| 2010/0292629 A1 | 11/2010 | Dacey, Jr. et al. |
| 2010/0298208 A1 | 11/2010 | Cohen et al. |
| 2010/0305062 A1 | 12/2010 | Onsoyen et al. |
| 2010/0316643 A1 | 12/2010 | Eckert et al. |
| 2010/0322903 A1 | 12/2010 | Collins et al. |
| 2011/0003001 A1 | 1/2011 | Baker |
| 2011/0005997 A1 | 1/2011 | Kurth et al. |
| 2011/0008402 A1 | 1/2011 | Madhyastha et al. |
| 2011/0008786 A1 | 1/2011 | Yu et al. |
| 2011/0015300 A1 | 1/2011 | Whiteford et al. |
| 2011/0027252 A1 | 2/2011 | Aehle et al. |
| 2011/0027384 A1 | 2/2011 | Kishen et al. |
| 2011/0029076 A1 | 2/2011 | Paletta et al. |
| 2011/0033520 A1 | 2/2011 | Mather et al. |
| 2011/0033882 A1 | 2/2011 | Aehle et al. |
| 2011/0039761 A1 | 2/2011 | Eckert et al. |
| 2011/0039762 A1 | 2/2011 | Eckert et al. |
| 2011/0039763 A1 | 2/2011 | Eckert et al. |
| 2011/0046041 A1 | 2/2011 | Neesham-Grenon et al. |
| 2011/0052664 A1 | 3/2011 | Tennican et al. |
| 2011/0059062 A1 | 3/2011 | Pellico |
| 2011/0070376 A1 | 3/2011 | Wales et al. |
| 2011/0077192 A1 | 3/2011 | Giuliani et al. |
| 2011/0086101 A1 | 4/2011 | Madhyastha et al. |
| 2011/0098323 A1 | 4/2011 | Opperman et al. |
| 2011/0104179 A1 | 5/2011 | Reynolds et al. |
| 2011/0105376 A1 | 5/2011 | England et al. |
| 2011/0105825 A1 | 5/2011 | Nayfach-Battilana |
| 2011/0110998 A1 | 5/2011 | Marquais-Bienewald et al. |
| 2011/0117067 A1 | 5/2011 | Esteghlalian et al. |
| 2011/0117158 A1 | 5/2011 | Melander et al. |
| 2011/0117160 A1 | 5/2011 | Bruno |
| 2011/0119774 A1 | 5/2011 | Zlotkin et al. |
| 2011/0124716 A1 | 5/2011 | Passineau |
| 2011/0129454 A1 | 6/2011 | Olmstead |
| 2011/0135621 A1 | 6/2011 | Miller et al. |
| 2011/0144566 A1 | 6/2011 | Dacey, Jr. et al. |
| 2011/0150765 A1 | 6/2011 | Boyden et al. |
| 2011/0150819 A1 | 6/2011 | Melander et al. |
| 2011/0152176 A1 | 6/2011 | Horswill |
| 2011/0152750 A1 | 6/2011 | Dacey, Jr. et al. |
| 2011/0152751 A1 | 6/2011 | Dacey, Jr. et al. |
| 2011/0152752 A1 | 6/2011 | Dacey, Jr. et al. |
| 2011/0152789 A1 | 6/2011 | Dacey, Jr. et al. |
| 2011/0152790 A1 | 6/2011 | Dacey, Jr. et al. |
| 2011/0152978 A1 | 6/2011 | Dacey, Jr. et al. |
| 2011/0160643 A1 | 6/2011 | Dacey, Jr. et al. |
| 2011/0160644 A1 | 6/2011 | Dacey, Jr. et al. |
| 2011/0160681 A1 | 6/2011 | Dacey, Jr. et al. |
| 2011/0171123 A1 | 7/2011 | Shirtliff et al. |
| 2011/0171189 A1 | 7/2011 | Olmstead |
| 2011/0171489 A1 | 7/2011 | Dou et al. |
| 2011/0172704 A1 | 7/2011 | Bleier et al. |
| 2011/0177048 A1 | 7/2011 | Olmstead |
| 2011/0177049 A1 | 7/2011 | Olmstead |
| 2011/0177050 A1 | 7/2011 | Olmstead |
| 2011/0177111 A1 | 7/2011 | Shirtliff et al. |
| 2011/0177148 A1 | 7/2011 | Dicosimo et al. |
| 2011/0178182 A1 | 7/2011 | Gabbai |
| 2011/0182873 A1 | 7/2011 | Olmstead |
| 2011/0182874 A1 | 7/2011 | Olmstead |
| 2011/0182959 A1 | 7/2011 | Cahill et al. |
| 2011/0201692 A1 | 8/2011 | Raad |
| 2011/0207816 A1 | 8/2011 | Jaffe |
| 2011/0208021 A1 | 8/2011 | Goodall et al. |
| 2011/0208023 A1 | 8/2011 | Goodall et al. |
| 2011/0208026 A1 | 8/2011 | Goodall et al. |
| 2011/0217312 A1 | 9/2011 | Otto et al. |
| 2011/0217544 A1 | 9/2011 | Young et al. |
| 2011/0220155 A1 | 9/2011 | Man et al. |
| 2011/0229586 A1 | 9/2011 | Barak |
| 2011/0236453 A1 | 9/2011 | Stensen et al. |
| 2011/0236769 A1 | 9/2011 | Xie et al. |
| 2011/0250290 A1 | 10/2011 | Marques et al. |
| 2011/0256187 A1 | 10/2011 | Hortelano et al. |
| 2011/0262511 A1 | 10/2011 | Love et al. |
| 2011/0266724 A1 | 11/2011 | Hulseman et al. |
| 2011/0274730 A1 | 11/2011 | Ceri et al. |
| 2011/0275518 A1 | 11/2011 | Marques et al. |
| 2011/0275912 A1 | 11/2011 | Boyden et al. |
| 2011/0280920 A1 | 11/2011 | Zlotkin et al. |
| 2011/0281921 A1 | 11/2011 | Srebnik et al. |
| 2011/0294668 A1 | 12/2011 | Melander et al. |
| 2011/0295088 A1 | 12/2011 | Boyden et al. |
| 2011/0295089 A1 | 12/2011 | Boyden et al. |
| 2011/0295090 A1 | 12/2011 | Boyden et al. |
| 2011/0300235 A1 | 12/2011 | Myntti |

(56) References Cited

U.S. PATENT DOCUMENTS

| | | |
|---|---|---|
| 2011/0301076 A1 | 12/2011 | Stensen et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 | 12/2011 | Zhang et al. |
| 2011/0305909 A1 | 12/2011 | Weaver et al. |
| 2011/0306699 A1 | 12/2011 | Whang et al. |
| 2011/0311647 A1 | 12/2011 | Gawande et al. |
| 2011/0319808 A1 | 12/2011 | Bowler et al. |
| 2012/0003163 A1 | 1/2012 | Mordas et al. |
| 2012/0010187 A1 | 1/2012 | Hoffman et al. |
| 2012/0010481 A1 | 1/2012 | Goodall et al. |
| 2012/0015870 A1 | 1/2012 | Zlotkin |
| 2012/0020896 A1 | 1/2012 | Trivedi et al. |
| 2012/0036767 A1 | 2/2012 | Larach |
| 2012/0039945 A1 | 2/2012 | Scott et al. |
| 2012/0040030 A1 | 2/2012 | Zinreich et al. |
| 2012/0041285 A1 | 2/2012 | Goodall et al. |
| 2012/0041286 A1 | 2/2012 | Goodall et al. |
| 2012/0041287 A1 | 2/2012 | Goodall et al. |
| 2012/0045817 A1 | 2/2012 | Estell et al. |
| 2012/0052052 A1 | 3/2012 | Xi et al. |
| 2012/0058076 A1 | 3/2012 | Widgerow |
| 2012/0058167 A1 | 3/2012 | Widgerow |
| 2012/0058169 A1 | 3/2012 | Olson et al. |
| 2012/0058933 A1 | 3/2012 | Gorr |
| 2012/0077736 A1 | 3/2012 | Oh et al. |
| 2012/0087887 A1 | 4/2012 | Hen et al. |
| 2012/0088671 A1 | 4/2012 | Quave et al. |
| 2012/0094007 A1 | 4/2012 | Fehr et al. |
| 2012/0101738 A1 | 4/2012 | Boyden et al. |
| 2012/0107258 A1 | 5/2012 | Kuhn et al. |
| 2012/0109613 A1 | 5/2012 | Boyden et al. |
| 2012/0122729 A1 | 5/2012 | Musken et al. |
| 2012/0128599 A1 | 5/2012 | Schaeffer-Korbylo et al. |
| 2012/0128783 A1 | 5/2012 | Boyden et al. |
| 2012/0129794 A1 | 5/2012 | Dowd et al. |
| 2012/0134951 A1 | 5/2012 | Stasko et al. |
| 2012/0135925 A1 | 5/2012 | Meijler et al. |
| 2012/0136323 A1 | 5/2012 | Stasko et al. |
| 2012/0142583 A1 | 6/2012 | Singh et al. |
| 2012/0149631 A1 | 6/2012 | Delatour et al. |
| 2012/0150119 A1 | 6/2012 | Schaeffer et al. |
| 2012/0152149 A1 | 6/2012 | Mijolovic et al. |
| 2012/0156645 A1 | 6/2012 | Jacoby |
| 2012/0157548 A1 | 6/2012 | Mijolovic et al. |
| 2012/0160779 A1 | 6/2012 | Barak |
| 2012/0164069 A1 | 6/2012 | Boyden et al. |
| 2012/0171129 A1 | 7/2012 | Melander et al. |
| 2012/0178971 A1 | 7/2012 | Khan et al. |
| 2012/0189682 A1 | 7/2012 | O'Neil et al. |
| 2012/0201869 A1 | 8/2012 | Burzell |
| 2012/0209090 A1 | 8/2012 | Goodall et al. |
| 2012/0210467 A1 | 8/2012 | Barton et al. |
| 2012/0213697 A1 | 8/2012 | Friedman et al. |
| 2012/0219638 A1 | 8/2012 | Olson et al. |
| 2012/0225098 A1 | 9/2012 | Kaplan et al. |
| 2012/0238644 A1 | 9/2012 | Gong et al. |
| 2012/0244126 A1 | 9/2012 | Collins et al. |
| 2012/0252101 A1 | 10/2012 | Chang et al. |
| 2012/0258089 A1 | 10/2012 | Madhyastha et al. |
| 2012/0258141 A9 | 10/2012 | Scott et al. |
| 2012/0263793 A1 | 10/2012 | Vitaliano |
| 2012/0283165 A1 | 11/2012 | Man et al. |
| 2012/0283174 A1 | 11/2012 | Reynolds et al. |
| 2012/0288566 A1 | 11/2012 | Friedman et al. |
| 2012/0288571 A1 | 11/2012 | Tennican et al. |
| 2012/0289591 A1 | 11/2012 | Folan |
| 2012/0294900 A1 | 11/2012 | Sintim et al. |
| 2012/0301433 A1 | 11/2012 | Lu et al. |
| 2012/0301481 A1 | 11/2012 | Otto et al. |
| 2012/0308632 A1 | 12/2012 | Ghigo et al. |
| 2012/0309701 A1 | 12/2012 | Janetka et al. |
| 2012/0315260 A1 | 12/2012 | Ivanova et al. |
| 2012/0321566 A1 | 12/2012 | Liu et al. |
| 2012/0328534 A1 | 12/2012 | Butterick et al. |
| 2012/0328577 A1 | 12/2012 | Melander et al. |
| 2012/0328671 A1 | 12/2012 | O'Neil et al. |
| 2012/0328683 A1 | 12/2012 | Song et al. |
| 2012/0328684 A1 | 12/2012 | Shanks et al. |
| 2012/0328708 A1 | 12/2012 | Van Der Waal et al. |
| 2012/0328713 A1 | 12/2012 | Olson et al. |
| 2012/0329675 A1 | 12/2012 | Olson et al. |
| 2012/0329746 A1 | 12/2012 | Reid |
| 2013/0005029 A1 | 1/2013 | Cascao-Pereira et al. |
| 2013/0011332 A1 | 1/2013 | Boyden et al. |
| 2013/0011887 A1 | 1/2013 | Dayton et al. |
| 2013/0022553 A1 | 1/2013 | Xu et al. |
| 2013/0022578 A1 | 1/2013 | Newman et al. |
| 2013/0022643 A1 | 1/2013 | Sternoff et al. |
| 2013/0029981 A1 | 1/2013 | De Keersmaecker et al. |
| 2013/0039978 A1 | 2/2013 | Schwarz et al. |
| 2013/0045182 A1 | 2/2013 | Gong et al. |
| 2013/0052250 A1 | 2/2013 | Burgess et al. |
| 2013/0058983 A1 | 3/2013 | Baker |
| 2013/0059096 A1 | 3/2013 | Losick et al. |
| 2013/0059113 A1 | 3/2013 | Hatton et al. |
| 2013/0059929 A1 | 3/2013 | Koehler et al. |
| 2013/0071319 A1 | 3/2013 | Boyden et al. |
| 2013/0071439 A1 | 3/2013 | Losick et al. |
| 2013/0095184 A1 | 4/2013 | Lyczak et al. |
| 2013/0101678 A1 | 4/2013 | Gordon et al. |
| 2013/0101963 A1 | 4/2013 | Sun |
| 2013/0102548 A1 | 4/2013 | Riley et al. |
| 2013/0102679 A1 | 4/2013 | Holden |
| 2013/0108708 A1 | 5/2013 | Xu |
| 2013/0110162 A1 | 5/2013 | Cohen |
| 2013/0116323 A1 | 5/2013 | Tirouvanziam et al. |
| 2013/0123225 A1 | 5/2013 | Melander et al. |
| 2013/0123319 A1 | 5/2013 | Bryan |
| 2013/0129768 A1 | 5/2013 | Reynolds |
| 2013/0129795 A1 | 5/2013 | Melander et al. |
| 2013/0129800 A1 | 5/2013 | Giammona et al. |
| 2013/0131172 A1 | 5/2013 | Zhang et al. |
| 2013/0131575 A1 | 5/2013 | Dacey, Jr. et al. |
| 2013/0136730 A1 | 5/2013 | Frank et al. |
| 2013/0136782 A1 | 5/2013 | Blackwell et al. |
| 2013/0149345 A1 | 6/2013 | Lipp et al. |
| 2013/0149542 A1 | 6/2013 | Chen et al. |
| 2013/0150451 A1 | 6/2013 | Salamone et al. |
| 2013/0150809 A1 | 6/2013 | Whiteford et al. |
| 2013/0158127 A1 | 6/2013 | Sergere |
| 2013/0158488 A1 | 6/2013 | Weaver et al. |
| 2013/0158517 A1 | 6/2013 | Bouchard et al. |
| 2013/0158518 A1 | 6/2013 | Li et al. |
| 2013/0164228 A1 | 6/2013 | Jaracz et al. |
| 2013/0164338 A1 | 6/2013 | Lipp et al. |
| 2013/0164363 A1 | 6/2013 | Raad |
| 2013/0164736 A1 | 6/2013 | Bernardi et al. |
| 2013/0165595 A1 | 6/2013 | Reid et al. |
| 2013/0171210 A1 | 7/2013 | Baker |
| 2013/0171224 A1 | 7/2013 | Percival et al. |
| 2013/0171228 A1 | 7/2013 | Morris |
| 2013/0172187 A1 | 7/2013 | Melander et al. |
| 2013/0183435 A1 | 7/2013 | Sun et al. |
| 2013/0190699 A1 | 7/2013 | Stephan |
| 2013/0196365 A1 | 8/2013 | Reddy et al. |
| 2013/0197455 A1 | 8/2013 | Zhang |
| 2013/0210708 A1 | 8/2013 | Singh et al. |
| 2013/0213398 A1 | 8/2013 | Lipp et al. |
| 2013/0220331 A1 | 8/2013 | Yahiaoui et al. |
| 2013/0224112 A1 | 8/2013 | Boyden et al. |
| 2013/0224258 A1 | 8/2013 | Baker |
| 2013/0224260 A1 | 8/2013 | Ward et al. |
| 2013/0225675 A1 | 8/2013 | Kubala et al. |
| 2013/0231302 A1 | 9/2013 | Raad et al. |
| 2013/0243828 A1 | 9/2013 | Lipp et al. |
| 2013/0245116 A1 | 9/2013 | Takayama et al. |
| 2013/0245130 A1 | 9/2013 | Watnick et al. |
| 2013/0252815 A1 | 9/2013 | Kolter et al. |
| 2013/0252818 A1 | 9/2013 | Lovejoy et al. |
| 2013/0252945 A1 | 9/2013 | Lovejoy et al. |
| 2013/0266521 A1 | 10/2013 | Fetissova et al. |
| 2013/0266522 A1 | 10/2013 | Fagon et al. |

(56) References Cited

U.S. PATENT DOCUMENTS

| | | |
|---|---|---|
| 2013/0266629 A1 | 10/2013 | Son |
| 2013/0266653 A1 | 10/2013 | Lipp et al. |
| 2013/0267471 A1 | 10/2013 | Ghatnekar et al. |
| 2013/0273116 A1 | 10/2013 | Jespersen et al. |
| 2013/0281324 A1 | 10/2013 | Gouliaev et al. |
| 2013/0281503 A1 | 10/2013 | Melander et al. |
| 2013/0287860 A1 | 10/2013 | Tennican et al. |
| 2013/0287861 A1 | 10/2013 | Tennican et al. |
| 2013/0288951 A1 | 10/2013 | Troxel et al. |
| 2013/0302390 A1 | 11/2013 | Davies |
| 2013/0309219 A1 | 11/2013 | Ratner et al. |
| 2013/0310346 A1 | 11/2013 | Zurawski |
| 2013/0315874 A1 | 11/2013 | Melander et al. |
| 2013/0315967 A1 | 11/2013 | Bruno |
| 2013/0315972 A1 | 11/2013 | Krasnow et al. |
| 2013/0330386 A1 | 12/2013 | Whitten et al. |
| 2013/0330388 A1 | 12/2013 | Sekhar |
| 2013/0337088 A1 | 12/2013 | Widgerow |
| 2013/0344542 A1 | 12/2013 | Cascao-Pereira et al. |
| 2013/0345261 A1 | 12/2013 | Waters et al. |
| 2014/0005605 A1 | 1/2014 | Samade et al. |
| 2014/0020138 A1 | 1/2014 | Ragunath et al. |
| 2014/0023691 A1 | 1/2014 | Melander et al. |
| 2014/0030306 A1 | 1/2014 | Polizzotti et al. |
| 2014/0037688 A1 | 2/2014 | Berkes et al. |
| 2014/0037967 A1 | 2/2014 | Roth et al. |
| 2014/0039195 A1 | 2/2014 | Luk et al. |
| 2014/0039357 A1 | 2/2014 | Boyden et al. |
| 2014/0045213 A1 | 2/2014 | Otto et al. |
| 2014/0056951 A1 | 2/2014 | Losick et al. |
| 2014/0056952 A1 | 2/2014 | Losick et al. |
| 2014/0056993 A1 | 2/2014 | Parsons |
| 2014/0057324 A1 | 2/2014 | Aehle et al. |
| 2014/0065200 A1 | 3/2014 | Schoenfisch et al. |
| 2014/0066441 A1 | 3/2014 | Surber et al. |
| 2014/0072525 A1 | 3/2014 | Adams, Jr. et al. |
| 2014/0073560 A1 | 3/2014 | Shanks et al. |
| 2014/0073690 A1 | 3/2014 | Meijler et al. |
| 2014/0079741 A1 | 3/2014 | Bink et al. |
| 2014/0079808 A1 | 3/2014 | Melander et al. |
| 2014/0083324 A1 | 3/2014 | Wales et al. |
| 2014/0105986 A1 | 4/2014 | Doxey et al. |
| 2014/0107071 A1 | 4/2014 | Kougoulos et al. |
| 2014/0120052 A1 | 5/2014 | Hen et al. |
| 2014/0127273 A1 | 5/2014 | Melander et al. |
| 2014/0128313 A1 | 5/2014 | Bishop et al. |
| 2014/0128590 A1 | 5/2014 | Bornscheuer et al. |
| 2014/0142028 A1 | 5/2014 | Eckert et al. |
| 2014/0142107 A1 | 5/2014 | Kaufman et al. |
| 2014/0147481 A1 | 5/2014 | Gerwick et al. |
| 2014/0155318 A1 | 6/2014 | Zlotkin |
| 2014/0155478 A1 | 6/2014 | Seneviratne et al. |
| 2014/0161728 A1 | 6/2014 | Bowler et al. |
| 2014/0161772 A1 | 6/2014 | Collins et al. |
| 2014/0161845 A1 | 6/2014 | Demuth et al. |
| 2014/0170195 A1 | 6/2014 | Fassih et al. |
| 2014/0170238 A1 | 6/2014 | Cliff et al. |
| 2014/0171438 A1 | 6/2014 | Pan et al. |
| 2014/0172049 A1 | 6/2014 | Nayfach-Battilana |
| 2014/0172117 A1 | 6/2014 | Anzai et al. |
| 2014/0178444 A1 | 6/2014 | Stadler et al. |
| 2014/0186318 A1 | 7/2014 | Ghannoum et al. |
| 2014/0186409 A1 | 7/2014 | Lang et al. |
| 2014/0187666 A1 | 7/2014 | Aizenberg et al. |
| 2014/0193489 A1 | 7/2014 | Rahimipour et al. |
| 2014/0193866 A1 | 7/2014 | Lam et al. |
| 2014/0193889 A1 | 7/2014 | McDaniel |
| 2014/0194594 A1 | 7/2014 | Gorr |
| 2014/0200511 A1 | 7/2014 | Boyden et al. |
| 2014/0205586 A1 | 7/2014 | Xi et al. |
| 2014/0205643 A1 | 7/2014 | Onsoyen et al. |
| 2014/0212828 A1 | 7/2014 | Falcone et al. |
| 2014/0221331 A1 | 8/2014 | Barraud et al. |
| 2014/0221610 A1 | 8/2014 | Zlotkin |
| 2014/0223602 A1 | 8/2014 | Chang et al. |
| 2014/0228327 A1 | 8/2014 | Raad |
| 2014/0234380 A1 | 8/2014 | Rayad et al. |
| 2014/0241997 A1 | 8/2014 | McInroy et al. |
| 2014/0242023 A1 | 8/2014 | Doxey et al. |
| 2014/0243725 A1 | 8/2014 | Tennican et al. |
| 2014/0248373 A1 | 9/2014 | Michalow et al. |
| 2014/0255318 A1 | 9/2014 | Stasko et al. |
| 2014/0256812 A1 | 9/2014 | Zhang et al. |
| 2014/0257482 A1 | 9/2014 | Ward et al. |
| 2014/0271757 A1 | 9/2014 | Agrawal et al. |
| 2014/0271763 A1 | 9/2014 | Burzell |
| 2014/0271777 A1 | 9/2014 | Quave et al. |
| 2014/0274875 A1 | 9/2014 | Troxel et al. |
| 2014/0276253 A1 | 9/2014 | Varga et al. |
| 2014/0276254 A1 | 9/2014 | Varga et al. |
| 2014/0277301 A1 | 9/2014 | Varga et al. |
| 2014/0288007 A1 | 9/2014 | Dashper et al. |
| 2014/0288171 A1 | 9/2014 | Whang et al. |
| 2014/0294907 A1 | 10/2014 | Bruno |
| 2014/0295523 A1 | 10/2014 | Steer et al. |
| 2014/0302113 A1 | 10/2014 | Zhang |
| 2014/0308217 A1 | 10/2014 | Schaeffer-Korbylo et al. |
| 2014/0308317 A1 | 10/2014 | Fan et al. |
| 2014/0308361 A1 | 10/2014 | Rayad et al. |
| 2014/0322351 A1 | 10/2014 | Gawande et al. |
| 2014/0322362 A1 | 10/2014 | Frim et al. |
| 2014/0328887 A1 | 11/2014 | Olson et al. |
| 2014/0328890 A1 | 11/2014 | Olson et al. |
| 2014/0328895 A1 | 11/2014 | Friedman et al. |
| 2014/0328999 A1 | 11/2014 | Aizenberg et al. |
| 2014/0335144 A1 | 11/2014 | Ward et al. |
| 2014/0336159 A1 | 11/2014 | Clarke et al. |
| 2014/0336700 A1 | 11/2014 | Dave et al. |
| 2014/0342954 A1 | 11/2014 | Ingber et al. |
| 2014/0348780 A1 | 11/2014 | Glasnapp |
| 2014/0349917 A1 | 11/2014 | Eckert et al. |
| 2014/0350017 A1 | 11/2014 | Williams et al. |
| 2014/0357592 A1 | 12/2014 | O'Neil et al. |
| 2014/0370078 A1 | 12/2014 | Gurtner et al. |
| 2014/0371171 A1 | 12/2014 | Souweine |
| 2014/0371476 A1 | 12/2014 | Dayton et al. |
| 2014/0377826 A1 | 12/2014 | Trevethick |
| 2015/0004233 A1 | 1/2015 | Lipp et al. |
| 2015/0005228 A1 | 1/2015 | Yang et al. |
| 2015/0011504 A1 | 1/2015 | Gong et al. |
| 2015/0018284 A1 | 1/2015 | Ghatnekar |
| 2015/0018330 A1 | 1/2015 | Hoffman et al. |
| 2015/0024000 A1 | 1/2015 | Shirtliff et al. |
| 2015/0024017 A1 | 1/2015 | Bukshpan et al. |
| 2015/0024052 A1 | 1/2015 | Doxey |
| 2015/0031738 A1 | 1/2015 | Li et al. |
| 2015/0038512 A1 | 2/2015 | Looper et al. |
| 2015/0038705 A1 | 2/2015 | Williams et al. |
| 2015/0044147 A1 | 2/2015 | Rayad et al. |
| 2015/0044260 A1 | 2/2015 | Birkedal et al. |
| 2015/0044266 A1 | 2/2015 | Fetissova et al. |
| 2015/0045515 A1 | 2/2015 | Li et al. |
| 2015/0050717 A1 | 2/2015 | Collins et al. |
| 2015/0056411 A1 | 2/2015 | Zhang et al. |
| 2015/0072066 A1 | 3/2015 | Karandikar et al. |
| 2015/0079141 A1 | 3/2015 | Wingfield |
| 2015/0080289 A1 | 3/2015 | Yang et al. |
| 2015/0080290 A1 | 3/2015 | Bevilacqua et al. |
| 2015/0086561 A1 | 3/2015 | Kauvar et al. |
| 2015/0086631 A1 | 3/2015 | Kishen et al. |
| 2015/0087573 A1 | 3/2015 | Estell et al. |
| 2015/0087582 A1 | 3/2015 | LoVetri et al. |
| 2015/0094368 A1 | 4/2015 | Scholz et al. |
| 2015/0099020 A1 | 4/2015 | Genin |
| 2015/0110898 A1 | 4/2015 | Gordon et al. |
| 2015/0111813 A1 | 4/2015 | Schuch et al. |
| 2015/0114504 A1 | 4/2015 | Cecka et al. |
| 2015/0118219 A1 | 4/2015 | Shi et al. |
| 2015/0132352 A1 | 5/2015 | Sun et al. |
| 2015/0136130 A1 | 5/2015 | DeHaan et al. |
| 2015/0147372 A1 | 5/2015 | Agrawal et al. |
| 2015/0147775 A1 | 5/2015 | Fiacco et al. |
| 2015/0148286 A1 | 5/2015 | Hakansson et al. |
| 2015/0148612 A1 | 5/2015 | Schaeffer et al. |

(56) References Cited

U.S. PATENT DOCUMENTS

| | | |
|---|---|---|
| 2015/0157542 A1 | 6/2015 | Schaeffer-Korbylo et al. |
| 2015/0157720 A1 | 6/2015 | Folan |
| 2015/0159180 A1 | 6/2015 | Prabhune et al. |
| 2015/0164769 A1 | 6/2015 | Mello et al. |
| 2015/0165095 A1 | 6/2015 | Mansouri et al. |
| 2015/0166706 A1 | 6/2015 | Hrabie et al. |
| 2015/0166796 A1 | 6/2015 | Sun et al. |
| 2015/0167046 A1 | 6/2015 | Ramasubramanian et al. |
| 2015/0173883 A1 | 6/2015 | Ingber et al. |
| 2015/0174302 A1 | 6/2015 | Troxel et al. |
| 2015/0182667 A1 | 7/2015 | Guelcher et al. |
| 2015/0183746 A1 | 7/2015 | Melander et al. |
| 2015/0190447 A1 | 7/2015 | Luc et al. |
| 2015/0191607 A1 | 7/2015 | McDaniel |
| 2015/0197538 A1 | 7/2015 | Janetka et al. |
| 2015/0197558 A1 | 7/2015 | Kauvar et al. |
| 2015/0202227 A1 | 7/2015 | Lipp et al. |
| 2015/0209393 A1 | 7/2015 | Chang et al. |
| 2015/0224220 A1 | 8/2015 | Olson et al. |
| 2015/0225458 A1 | 8/2015 | Rapsch et al. |
| 2015/0225488 A1 | 8/2015 | Schoenfisch et al. |
| 2015/0231045 A1 | 8/2015 | Krohn et al. |
| 2015/0231066 A1 | 8/2015 | Lipp et al. |
| 2015/0231287 A1 | 8/2015 | Lin et al. |
| 2015/0237870 A1 | 8/2015 | Pei |
| 2015/0238543 A1 | 8/2015 | Rickard et al. |
| 2015/0245618 A9 | 9/2015 | Agrawal et al. |
| 2015/0246995 A1 | 9/2015 | Hanson et al. |
| 2015/0250875 A1 | 9/2015 | Lipp et al. |
| 2015/0259390 A1 | 9/2015 | Zlotkin |
| 2015/0267162 A1 | 9/2015 | Kanehara et al. |
| 2015/0274639 A1 | 10/2015 | Williams et al. |
| 2015/0283208 A1 | 10/2015 | Ribbeck et al. |
| 2015/0283287 A1 | 10/2015 | Agarwal et al. |
| 2015/0297478 A1 | 10/2015 | Ratcliff et al. |
| 2015/0297642 A1 | 10/2015 | Borody |
| 2015/0299298 A1 | 10/2015 | Kauvar et al. |
| 2015/0299345 A1 | 10/2015 | Xu et al. |
| 2015/0315253 A1 | 11/2015 | Zlotkin et al. |
| 2015/0322113 A1 | 11/2015 | Atreya et al. |
| 2015/0322272 A1 | 11/2015 | Pokroy et al. |
| 2015/0327552 A1 | 11/2015 | Melander et al. |
| 2015/0330020 A1 | 11/2015 | van Buskirk et al. |
| 2015/0332151 A1 | 11/2015 | Marculescu et al. |
| 2015/0335013 A1 | 11/2015 | Sabin |
| 2015/0335027 A1 | 11/2015 | Sabin |
| 2015/0336855 A1 | 11/2015 | Sabin |
| 2015/0344918 A1 | 12/2015 | Lam et al. |
| 2015/0351383 A1 | 12/2015 | Kolari et al. |
| 2015/0351392 A1 | 12/2015 | Graber et al. |
| 2015/0351406 A1 | 12/2015 | Wingfield et al. |
| 2015/0368480 A1 | 12/2015 | Reches |
| 2015/0373989 A1 | 12/2015 | Krasnow et al. |
| 2015/0374634 A1 | 12/2015 | Koo et al. |
| 2015/0374658 A1 | 12/2015 | Krohn et al. |
| 2015/0374720 A1 | 12/2015 | Genberg et al. |
| 2016/0008275 A1 | 1/2016 | Doxey et al. |
| 2016/0009733 A1 | 1/2016 | Barraud et al. |
| 2016/0010137 A1 | 1/2016 | Potnis et al. |
| 2016/0015047 A1 | 1/2016 | Gawande et al. |
| 2016/0021882 A1 | 1/2016 | Wang et al. |
| 2016/0022564 A1 | 1/2016 | Townsend et al. |
| 2016/0022595 A1 | 1/2016 | Shikani et al. |
| 2016/0022707 A1 | 1/2016 | Zhong et al. |
| 2016/0024551 A1 | 1/2016 | Hassett et al. |
| 2016/0030327 A1 | 2/2016 | Stein |
| 2016/0031941 A1 | 2/2016 | Eckert et al. |
| 2016/0032180 A1 | 2/2016 | Agrawal et al. |
| 2016/0038572 A1 | 2/2016 | Nelson |
| 2016/0038650 A1 | 2/2016 | Griffith |
| 2016/0045841 A1 | 2/2016 | Kaplan et al. |
| 2016/0051569 A1 | 2/2016 | Banov |
| 2016/0058675 A1 | 3/2016 | Xu et al. |
| 2016/0058693 A1 | 3/2016 | Widgerow |
| 2016/0058772 A1 | 3/2016 | Baker |
| 2016/0058816 A1 | 3/2016 | Widgerow |
| 2016/0058834 A1 | 3/2016 | Ghatnekar |
| 2016/0058998 A1 | 3/2016 | Skiba et al. |
| 2016/0060284 A1 | 3/2016 | Oscarson et al. |
| 2016/0060609 A1 | 3/2016 | Bornscheuer et al. |
| 2016/0067149 A1 | 3/2016 | Kishen |
| 2016/0073638 A1 | 3/2016 | Li et al. |
| 2016/0074345 A1 | 3/2016 | Holden |
| 2016/0075714 A1 | 3/2016 | Opperman et al. |
| 2016/0075749 A1 | 3/2016 | Nibbering et al. |
| 2016/0089481 A1 | 3/2016 | Arvidsson et al. |
| 2016/0096865 A1 | 4/2016 | Martinez et al. |
| 2016/0106107 A1 | 4/2016 | Marques et al. |
| 2016/0106689 A1 | 4/2016 | O'Neil |
| 2016/0107126 A1 | 4/2016 | Cates |
| 2016/0109401 A1 | 4/2016 | Wardell et al. |
| 2016/0113940 A1 | 4/2016 | Crapo et al. |
| 2016/0115145 A1 | 4/2016 | Kolter et al. |
| 2016/0120184 A1 | 5/2016 | Gedanken et al. |
| 2016/0120793 A1 | 5/2016 | Abdalla et al. |
| 2016/0122697 A1 | 5/2016 | Skiba et al. |
| 2016/0128335 A1 | 5/2016 | Sabin |
| 2016/0129078 A1 | 5/2016 | Ko et al. |
| 2016/0135463 A9 | 5/2016 | Reid et al. |
| 2016/0135469 A1 | 5/2016 | Olson et al. |
| 2016/0135470 A1 | 5/2016 | Agrawal et al. |
| 2016/0137563 A1 | 5/2016 | Sabin |
| 2016/0137564 A1 | 5/2016 | Sabin |
| 2016/0137565 A1 | 5/2016 | Sabin |
| 2016/0144004 A1 | 5/2016 | Pellico |
| 2016/0145289 A1 | 5/2016 | Janetka et al. |
| 2016/0157497 A1 | 6/2016 | Zlotkin |
| 2016/0158169 A1 | 6/2016 | O'Neil et al. |
| 2016/0158353 A1 | 6/2016 | Kielian |
| 2016/0158421 A1 | 6/2016 | Troxel et al. |
| 2016/0166712 A1 | 6/2016 | Pavlicek et al. |
| 2016/0168604 A1 | 6/2016 | Lam et al. |
| 2016/0176815 A1 | 6/2016 | Li et al. |
| 2016/0184485 A1 | 6/2016 | Zhang |
| 2016/0185630 A1 | 6/2016 | Gupta et al. |
| 2016/0186147 A1 | 6/2016 | Cady et al. |
| 2016/0193344 A1 | 7/2016 | Sershen et al. |
| 2016/0194288 A1 | 7/2016 | Melander et al. |
| 2016/0198994 A1 | 7/2016 | Murphy et al. |
| 2016/0199295 A1 | 7/2016 | Doxey et al. |
| 2016/0205946 A1 | 7/2016 | Staueeer et al. |
| 2016/0206575 A1 | 7/2016 | O'Neil et al. |
| 2016/0212996 A1 | 7/2016 | Ghigo et al. |
| 2016/0213001 A1 | 7/2016 | Parthasarathy et al. |
| 2016/0220722 A1 | 8/2016 | Wardell et al. |
| 2016/0220728 A1 | 8/2016 | Adams et al. |
| 2016/0223553 A1 | 8/2016 | Sears et al. |
| 2016/0235698 A1 | 8/2016 | Rickard et al. |
| 2016/0235893 A1 | 8/2016 | Lucchino et al. |
| 2016/0235894 A1 | 8/2016 | Ghigo et al. |
| 2016/0237145 A1 | 8/2016 | Kauvar et al. |
| 2016/0242413 A1 | 8/2016 | Wuest et al. |
| 2016/0249612 A1 | 9/2016 | Gambogi et al. |
| 2016/0251571 A1 | 9/2016 | Agrawal et al. |
| 2016/0256484 A1 | 9/2016 | Doxey et al. |
| 2016/0262384 A1 | 9/2016 | Wuest et al. |
| 2016/0263225 A1 | 9/2016 | Zakrewsky et al. |
| 2016/0270411 A1 | 9/2016 | Mart Nore et al. |
| 2016/0278375 A1 | 9/2016 | Wuest et al. |
| 2016/0279138 A1 | 9/2016 | Surber et al. |
| 2016/0279191 A1 | 9/2016 | Glasnapp |
| 2016/0279314 A1 | 9/2016 | Eliaz |
| 2016/0280570 A1 | 9/2016 | Fratt et al. |
| 2016/0280772 A1 | 9/2016 | Salomon et al. |
| 2016/0289272 A1 | 10/2016 | Otterlei et al. |
| 2016/0289287 A1 | 10/2016 | Hancock et al. |
| 2016/0296434 A1 | 10/2016 | Fei et al. |
| 2016/0304886 A1 | 10/2016 | Rickard et al. |
| 2016/0309711 A1 | 10/2016 | Jackson et al. |
| 2016/0317611 A1 | 11/2016 | Nibbering et al. |
| 2016/0317618 A1 | 11/2016 | Fikrig et al. |
| 2016/0319224 A1 | 11/2016 | Lant et al. |
| 2016/0319225 A1 | 11/2016 | Lant et al. |
| 2016/0319226 A1 | 11/2016 | Lant et al. |

(56) References Cited

U.S. PATENT DOCUMENTS

| | | |
|---|---|---|
| 2016/0319227 A1 | 11/2016 | Lant et al. |
| 2016/0319228 A1 | 11/2016 | Lant et al. |
| 2016/0324531 A1 | 11/2016 | Gross et al. |
| 2016/0326503 A1 | 11/2016 | Barton et al. |
| 2016/0330962 A1 | 11/2016 | Looper et al. |
| 2016/0331719 A1 | 11/2016 | Watnick et al. |
| 2016/0338993 A1 | 11/2016 | Martins-Green et al. |
| 2016/0339071 A1 | 11/2016 | Tufenkji et al. |
| 2016/0346115 A1 | 12/2016 | Varga et al. |
| 2016/0346161 A1 | 12/2016 | Varga et al. |
| 2016/0346294 A1 | 12/2016 | Sengupta et al. |
| 2016/0346436 A1 | 12/2016 | Boluk et al. |
| 2016/0353739 A1 | 12/2016 | Melander et al. |
| 2016/0353746 A1 | 12/2016 | Dale et al. |
| 2016/0354289 A1 | 12/2016 | Sternoff et al. |
| 2016/0355487 A1 | 12/2016 | Huigens et al. |
| 2016/0375034 A1 | 12/2016 | Baker et al. |
| 2016/0375074 A1 | 12/2016 | Quave et al. |
| 2016/0376449 A1 | 12/2016 | Reches |
| 2017/0007733 A1 | 1/2017 | Boyden et al. |
| 2017/0009084 A1 | 1/2017 | Margel et al. |
| 2017/0014208 A1 | 1/2017 | Falcone et al. |
| 2017/0014437 A1 | 1/2017 | Luk et al. |
| 2017/0014511 A1 | 1/2017 | Vitaliano et al. |
| 2017/0020139 A1 | 1/2017 | Berkes et al. |
| 2017/0020813 A1 | 1/2017 | Lipp et al. |
| 2017/0021040 A1 | 1/2017 | Vitaliano et al. |
| 2017/0022165 A1 | 1/2017 | Lu et al. |
| 2017/0022371 A1 | 1/2017 | Lynn et al. |
| 2017/0028106 A1 | 2/2017 | Brisbois et al. |
| 2017/0029363 A1 | 2/2017 | Caran et al. |
| 2017/0035786 A1 | 2/2017 | Banov |
| 2017/0035955 A1 | 2/2017 | Eliaz |
| 2017/0042965 A1 | 2/2017 | Bevilacqua et al. |
| 2017/0043111 A1 | 2/2017 | Hoftman et al. |
| 2017/0044222 A1 | 2/2017 | Alexander et al. |
| 2017/0049113 A1 | 2/2017 | Duncan et al. |
| 2017/0050893 A1 | 2/2017 | Sabin |
| 2017/0050927 A1 | 2/2017 | Li et al. |
| 2017/0056297 A1 | 3/2017 | Kishen et al. |
| 2017/0056405 A1 | 3/2017 | Sun et al. |
| 2017/0056437 A1 | 3/2017 | Stasko et al. |
| 2017/0056454 A1 | 3/2017 | Berkes et al. |
| 2017/0056455 A1 | 3/2017 | Berkes et al. |
| 2017/0056565 A1 | 3/2017 | Kepler et al. |
| 2017/0064966 A1 | 3/2017 | Opatowsky et al. |
| 2017/0065564 A1 | 3/2017 | Shaw et al. |
| 2017/0065673 A1 | 3/2017 | Birkedal et al. |
| 2017/0071212 A1 | 3/2017 | Sabin |
| 2017/0071986 A1 | 3/2017 | Kovarik et al. |
| 2017/0072024 A1 | 3/2017 | Malepeyre et al. |
| 2017/0072098 A1 | 3/2017 | Drago et al. |
| 2017/0073706 A1 | 3/2017 | Ghigo et al. |
| 2017/0080130 A1 | 3/2017 | Pichler-Wilhelm et al. |
| 2017/0095502 A1 | 4/2017 | Sarangapani |
| 2017/0100328 A1 | 4/2017 | Kovarik et al. |
| 2017/0100348 A1 | 4/2017 | Wright |
| 2017/0100357 A1 | 4/2017 | Folan |
| 2017/0100512 A1 | 4/2017 | Matheny |
| 2017/0100513 A1 | 4/2017 | Matheny |
| 2017/0100514 A1 | 4/2017 | Matheny |
| 2017/0100515 A1 | 4/2017 | Matheny |
| 2017/0100516 A1 | 4/2017 | Matheny |
| 2017/0100517 A1 | 4/2017 | Matheny |
| 2017/0100518 A1 | 4/2017 | Matheny |
| 2017/0100522 A1 | 4/2017 | Matheny |
| 2017/0100523 A1 | 4/2017 | Matheny |
| 2017/0106188 A1 | 4/2017 | King et al. |
| 2017/0107250 A1 | 4/2017 | Stensen et al. |
| 2017/0112136 A1 | 4/2017 | Wood et al. |
| 2017/0112723 A1 | 4/2017 | Xu et al. |
| 2017/0113038 A1 | 4/2017 | Nagel et al. |
| 2017/0119915 A1 | 5/2017 | Lin et al. |
| 2017/0127683 A1 | 5/2017 | Schuch et al. |
| 2017/0128338 A1 | 5/2017 | Gawande et al. |
| 2017/0128502 A1 | 5/2017 | Berkes et al. |
| 2017/0128720 A1 | 5/2017 | Skiba |
| 2017/0135342 A1 | 5/2017 | Caran et al. |
| 2017/0137380 A1 | 5/2017 | Rodrigues et al. |
| 2017/0142978 A1 | 5/2017 | Falken |
| 2017/0143624 A1 | 5/2017 | Lipp et al. |
| 2017/0143842 A1 | 5/2017 | Smyth et al. |
| 2017/0150724 A1 | 6/2017 | Baker |
| 2017/0156321 A1 | 6/2017 | Li et al. |
| 2017/0158537 A1 | 6/2017 | Buschmann |
| 2017/0158727 A1 | 6/2017 | Coenye et al. |
| 2017/0159237 A1 | 6/2017 | Buschmann et al. |
| 2017/0173186 A9 | 6/2017 | Pavlicek et al. |
| 2017/0173225 A1 | 6/2017 | Troxel |
| 2017/0182205 A1 | 6/2017 | Zupancic et al. |
| 2017/0183469 A1 | 6/2017 | Falken et al. |
| 2017/0189556 A1 | 7/2017 | Seleem |
| 2017/0197028 A1 | 7/2017 | Goldsmith |
| 2017/0202752 A1 | 7/2017 | Xu et al. |
| 2017/0204123 A1 | 7/2017 | Holmes et al. |
| 2017/0216094 A1 | 8/2017 | Reo et al. |
| 2017/0216197 A1 | 8/2017 | McHale et al. |
| 2017/0216369 A1 | 8/2017 | Sabacinski et al. |
| 2017/0216377 A1 | 8/2017 | Berkes et al. |
| 2017/0216410 A1 | 8/2017 | Howell et al. |
| 2017/0224703 A1 | 8/2017 | Kaufman et al. |
| 2017/0224748 A1 | 8/2017 | Berkes et al. |
| 2017/0226133 A1 | 8/2017 | Holmes et al. |
| 2017/0232038 A1 | 8/2017 | O'Flaherty et al. |
| 2017/0232048 A1 | 8/2017 | Edwards |
| 2017/0232153 A1 | 8/2017 | Babu et al. |
| 2017/0240618 A1 | 8/2017 | Zurawski |
| 2017/0246205 A1 | 8/2017 | Stasko et al. |
| 2017/0246341 A1 | 8/2017 | Hanson et al. |
| 2017/0247401 A1 | 8/2017 | Janetka et al. |
| 2017/0247409 A1 | 8/2017 | Moreira et al. |
| 2017/0247414 A1 | 8/2017 | Gruber |
| 2017/0247688 A1 | 8/2017 | Franch et al. |
| 2017/0252320 A1 | 9/2017 | Martins-Green et al. |
| 2017/0258963 A1 | 9/2017 | Savage et al. |
| 2017/0266239 A1 | 9/2017 | Borody |
| 2017/0266306 A1 | 9/2017 | Eckert et al. |
| 2017/0273301 A1 | 9/2017 | Benson |
| 2017/0274082 A1 | 9/2017 | Sershen et al. |
| 2017/0280725 A1 | 10/2017 | Jin et al. |
| 2017/0281570 A1 | 10/2017 | Gurtner et al. |
| 2017/0281667 A1 | 10/2017 | Acharya et al. |
| 2017/0281699 A1 | 10/2017 | Berkes et al. |
| 2017/0283763 A1 | 10/2017 | Newman et al. |
| 2017/0290789 A1 | 10/2017 | DiCosmo |
| 2017/0290854 A1 | 10/2017 | Matlick |
| 2017/0295784 A1 | 10/2017 | Bolduc et al. |
| 2017/0296599 A1 | 10/2017 | Berkes et al. |
| 2017/0297055 A1 | 10/2017 | Detrembleur et al. |
| 2017/0304564 A1 | 10/2017 | DeHaan et al. |
| 2017/0312307 A1 | 11/2017 | Stasko et al. |
| 2017/0312345 A1 | 11/2017 | Ivanova et al. |
| 2017/0326054 A1 | 11/2017 | Spears et al. |
| 2017/0333455 A1 | 11/2017 | Manley et al. |
| 2017/0333601 A1 | 11/2017 | Burgess et al. |
| 2017/0339962 A1 | 11/2017 | Sabin |
| 2017/0340779 A1 | 11/2017 | Burgess et al. |
| 2017/0347661 A1 | 12/2017 | Parsons |
| 2017/0347664 A1 | 12/2017 | Thompson et al. |
| 2017/0360534 A1 | 12/2017 | Sun et al. |
| 2017/0360982 A1 | 12/2017 | Wardell et al. |
| 2017/0362562 A1 | 12/2017 | Nguyen et al. |
| 2017/0367933 A1 | 12/2017 | Aparicio et al. |
| 2018/0000993 A1 | 1/2018 | Zhang |
| 2018/0008533 A1 | 1/2018 | McHale et al. |
| 2018/0008742 A1 | 1/2018 | Hoggarth et al. |
| 2018/0014974 A1 | 1/2018 | Hoggarth et al. |
| 2018/0014975 A1 | 1/2018 | Hoggarth et al. |
| 2018/0015061 A1 | 1/2018 | Gawande et al. |
| 2018/0016311 A1 | 1/2018 | Zlotkin et al. |
| 2018/0021463 A1 | 1/2018 | Osinski et al. |
| 2018/0028417 A1 | 2/2018 | Koo et al. |
| 2018/0028701 A1 | 2/2018 | Fu et al. |
| 2018/0028713 A1 | 2/2018 | Agarwal et al. |

(56) References Cited

U.S. PATENT DOCUMENTS

| | | |
|---|---|---|
| 2018/0030403 A1 | 2/2018 | Subhadra |
| 2018/0030404 A1 | 2/2018 | Subhadra |
| 2018/0030405 A1 | 2/2018 | Subhadra |
| 2018/0030406 A1 | 2/2018 | Subhadra |
| 2018/0036286 A1 | 2/2018 | Shaw et al. |
| 2018/0036702 A1 | 2/2018 | Wellings |
| 2018/0037545 A1 | 2/2018 | Silver |
| 2018/0037613 A1 | 2/2018 | Paetzold et al. |
| 2018/0042789 A1 | 2/2018 | Bradford et al. |
| 2018/0042928 A1 | 2/2018 | Sun et al. |
| 2018/0043190 A1 | 2/2018 | Myers et al. |
| 2018/0049856 A1 | 2/2018 | Ionescu et al. |
| 2018/0051061 A1 | 2/2018 | Wang |
| 2018/0079757 A1 | 3/2018 | Tse-Dinh et al. |
| 2018/0079912 A1 | 3/2018 | Reches |
| 2018/0085335 A1 | 3/2018 | Sun et al. |
| 2018/0085392 A1 | 3/2018 | Gaspar et al. |
| 2018/0085489 A1 | 3/2018 | Hanson et al. |
| 2018/0085717 A1 | 3/2018 | Ermatov et al. |
| 2018/0092939 A1 | 4/2018 | Onsoyen et al. |
| 2018/0093011 A1 | 4/2018 | Kellar et al. |
| 2018/0094214 A1 | 4/2018 | Labib et al. |
| 2018/0105792 A1 | 4/2018 | Subhadra |
| 2018/0110228 A1 | 4/2018 | Myers et al. |
| 2018/0111893 A1 | 4/2018 | Wuest et al. |
| 2018/0111955 A1 | 4/2018 | Oscarson et al. |
| 2018/0112068 A1 | 4/2018 | Segal et al. |
| 2018/0119235 A1 | 5/2018 | Talianski et al. |
| 2018/0125066 A1 | 5/2018 | Bassler et al. |
| 2018/0125070 A1 | 5/2018 | Looper et al. |
| 2018/0133326 A1 | 5/2018 | McInroy et al. |
| 2018/0153172 A1 | 6/2018 | Zlotkin |
| 2018/0153996 A1 | 6/2018 | Lipp et al. |
| 2018/0184656 A1 | 7/2018 | DiLuccio |
| 2018/0185518 A1 | 7/2018 | Vitaliano et al. |
| 2018/0194792 A1 | 7/2018 | Janetka et al. |
| 2018/0200185 A1 | 7/2018 | Labib et al. |
| 2018/0207122 A1 | 7/2018 | Scholz et al. |
| 2018/0244901 A1 | 8/2018 | Kenny et al. |
| 2018/0265475 A1 | 9/2018 | Huigens et al. |
| 2018/0298307 A1 | 10/2018 | Lant et al. |
| 2018/0298552 A9 | 10/2018 | van Buskirk et al. |
| 2018/0303846 A1 | 10/2018 | Domenico |
| 2018/0310566 A1 | 11/2018 | Sawyer et al. |
| 2018/0312473 A1 | 11/2018 | Huigens |
| 2018/0318313 A1 | 11/2018 | Sengupta et al. |
| 2018/0325740 A1 | 11/2018 | Kenny et al. |
| 2018/0338945 A1 | 11/2018 | Sambasivam |
| 2018/0353556 A1 | 12/2018 | Berkes et al. |
| 2018/0360856 A1 | 12/2018 | Holmes et al. |
| 2018/0369258 A1 | 12/2018 | Holmes et al. |
| 2019/0000090 A1 | 1/2019 | Wood et al. |
| 2019/0002706 A1 | 1/2019 | Margel et al. |
| 2019/0003113 A1 | 1/2019 | Altman et al. |
| 2019/0008784 A1 | 1/2019 | Jacks et al. |
| 2019/0017050 A1 | 1/2019 | Thanos et al. |
| 2019/0031545 A1 | 1/2019 | Buschmann et al. |
| 2019/0048308 A1 | 2/2019 | Nguyen et al. |
| 2019/0099459 A1 | 4/2019 | Camilli et al. |
| 2019/0125825 A1 | 5/2019 | Blackledge et al. |
| 2019/0134151 A1 | 5/2019 | Bond et al. |
| 2019/0144738 A1 | 5/2019 | Agrawal et al. |
| 2019/0192691 A1 | 6/2019 | Barrett et al. |
| 2019/0201371 A1 | 7/2019 | Baker |
| 2019/0209646 A1 | 7/2019 | Xie |
| 2019/0211045 A1 | 7/2019 | Janetka et al. |
| 2019/0211312 A1 | 7/2019 | Cady et al. |
| 2019/0216691 A1 | 7/2019 | Wellings |
| 2019/0249115 A1 | 8/2019 | Labib et al. |
| 2019/0262393 A1 | 8/2019 | Pesavento |
| 2019/0264164 A1 | 8/2019 | Nguyen et al. |
| 2019/0282754 A1 | 9/2019 | Koulakis et al. |
| 2019/0307726 A1 | 10/2019 | Holmgren et al. |
| 2019/0322988 A1 | 10/2019 | Cady et al. |
| 2019/0330618 A1 | 10/2019 | Franch et al. |
| 2019/0352592 A1 | 11/2019 | Nguyen et al. |
| 2019/0365868 A1 | 12/2019 | Sauer et al. |
| 2019/0373890 A1 | 12/2019 | Huigens et al. |
| 2019/0374213 A1 | 12/2019 | Goldsmith |
| 2019/0376052 A1 | 12/2019 | Steer et al. |
| 2019/0381038 A1 | 12/2019 | Altschul et al. |
| 2019/0381057 A1 | 12/2019 | Surber et al. |
| 2019/0387745 A1 | 12/2019 | Schuch et al. |
| 2019/0388342 A1 | 12/2019 | Sung et al. |
| 2020/0002377 A1 | 1/2020 | Van Den Nest et al. |
| 2020/0010432 A1 | 1/2020 | Huigens et al. |
| 2020/0022989 A1 | 1/2020 | Baker |
| 2020/0031757 A1 | 1/2020 | Looper et al. |
| 2020/0069777 A1 | 3/2020 | Staples et al. |
| 2020/0071702 A1 | 3/2020 | Thanos et al. |
| 2020/0102340 A1 | 4/2020 | Oscarson et al. |
| 2020/0107551 A1 | 4/2020 | Sawyer et al. |
| 2020/0108107 A1 | 4/2020 | Berkes et al. |
| 2020/0109297 A1 | 4/2020 | McDaniel |
| 2020/0121715 A1 | 4/2020 | Bishop et al. |
| 2020/0138033 A1 | 5/2020 | Baker |
| 2020/0138037 A1 | 5/2020 | Dale et al. |
| 2020/0138708 A1 | 5/2020 | Labib et al. |
| 2020/0138753 A1 | 5/2020 | Jennings et al. |
| 2020/0154708 A1 | 5/2020 | Stadler et al. |
| 2020/0155640 A1 | 5/2020 | Heckler et al. |
| 2020/0163333 A1 | 5/2020 | Gandhi et al. |
| 2020/0164080 A1 | 5/2020 | Hedrick et al. |
| 2020/0172853 A1 | 6/2020 | Nguyen et al. |
| 2020/0179458 A1 | 6/2020 | Ambrogio et al. |
| 2020/0197483 A1 | 6/2020 | Bond et al. |
| 2020/0199000 A1 | 6/2020 | Buschmann |
| 2020/0206277 A1 | 7/2020 | Whitlock et al. |
| 2020/0215123 A1 | 7/2020 | Thanos et al. |
| 2020/0216836 A1 | 7/2020 | Franch et al. |
| 2020/0256009 A1 | 8/2020 | Altman et al. |
| 2020/0261667 A1 | 8/2020 | DeHaan et al. |
| 2020/0263123 A1 | 8/2020 | Nguyen et al. |
| 2020/0264050 A1 | 8/2020 | Auner et al. |
| 2020/0268031 A1 | 8/2020 | Macur et al. |
| 2020/0270559 A1 | 8/2020 | Macur et al. |
| 2020/0270613 A1 | 8/2020 | Thanos et al. |
| 2020/0275653 A1 | 9/2020 | Davies |
| 2020/0276214 A1 | 9/2020 | Waters et al. |
| 2020/0277263 A1 | 9/2020 | Wuest et al. |
| 2020/0296971 A1 | 9/2020 | McLean et al. |
| 2020/0299521 A1 | 9/2020 | McDaniel |
| 2020/0306163 A1 | 10/2020 | Altman |
| 2020/0318284 A1 | 10/2020 | van Buskirk et al. |
| 2020/0330206 A1 | 10/2020 | Sagel et al. |
| 2020/0330340 A1 | 10/2020 | Sagel et al. |
| 2020/0330341 A1 | 10/2020 | Sagel et al. |
| 2020/0330510 A1 | 10/2020 | Chatzistavrou et al. |
| 2020/0330784 A1 | 10/2020 | Sagel et al. |
| 2020/0345585 A1 | 11/2020 | Dresdner, Jr. et al. |
| 2020/0353085 A1 | 11/2020 | Farmer et al. |
| 2020/0354588 A1 | 11/2020 | McDaniel |
| 2020/0368312 A1 | 11/2020 | Heckler et al. |
| 2020/0397547 A1 | 12/2020 | Sagel et al. |
| 2020/0397548 A1 | 12/2020 | Sagel et al. |
| 2020/0397549 A1 | 12/2020 | Sagel et al. |
| 2020/0397550 A1 | 12/2020 | Sagel et al. |
| 2020/0399562 A1 | 12/2020 | Lant et al. |

FOREIGN PATENT DOCUMENTS

| | | |
|---|---|---|
| EP | 06849263 | 4/1975 |
| EP | 06849263 | 12/2020 |
| JP | 02241546 | 4/1975 |
| JP | 07173166 | 4/1975 |
| JP | 10182450 | 4/1975 |
| JP | 2002241546 | 8/2002 |
| JP | 2003137758 | 5/2003 |
| JP | 2004018431 | 1/2004 |
| JP | 2006062966 | 3/2006 |
| JP | 2007239280 | 9/2007 |
| JP | 5495535 | 10/2007 |
| JP | 58213716 | 10/2007 |
| JP | 59193809 | 10/2007 |

(56) References Cited

FOREIGN PATENT DOCUMENTS

| JP | 59199606 | 10/2007 |
|---|---|---|
| JP | 60009728 | 10/2007 |
| JP | 61106501 | 10/2007 |
| JP | 2007262050 | 10/2007 |
| WO | WO2002027018 | 4/2002 |
| WO | WO2005034933 | 4/2005 |
| WO | WO2007081455 | 7/2007 |
| WO | WO2007092633 | 8/2007 |

OTHER PUBLICATIONS

Boon et al., "A Novel DSF-like Signal from Burkholderia cenocepacia Interferes with Candida albicans Morphological Transition," The ISME Journal 2:27-36 (2008).
Borchardt et al., "Reaction of Acylated Homoserine Lactone Bacterial Signaling Molecules with Oxidized Halogen Antimicrobials," Appl. Environ. Microbiol. 67(7):3174-3179 (2001).
Davies & Geesey, "Regulation of the Alginate Biosynthesis Gene algC in Pseudomonas aeruginosa During Biofilm Development in Continuous Culture," Appl. Environ. Microbiol. 61(3):860-7 (1995).
Davies & Marques, "A Fatty Acid Messenger is Responsible for Inducing Dispersion in Microbial Biofilms," Department of Biological Sciences, State University of New York at Binghamtom.
Davies et al., "Exopolysaccharide Production in Biofilms: Substratum Activation of Alginate Gene Expression by Pseudomonas aeruginosa," Appl. Environ. Microbiol. 59(4):1181-6 (1993).
Davies et al., "The Involvement of Cell-to-Cell Signals in the Development of a Bacterial Biofilm," Science 280(5361):295-8 (1998).
Davies et al., Abstract Q-100, "Autoinduction of Pseudomonas Aeruginosa Biofilm Dispersion," ASM 105th General Meeting, Atlanta, GA (Jun. 6, 2005), Biosciences Information Service, XP009133221, Database Accession No. PREV200800237844 (Abstract).
Davies et al., Abstract Q-161, "Autodispersion in Pseudomonas Aeruginosa Biofilms," ASM 103rd General Meeting, Washington, D.C. (May 20, 2003), Biosciences Information Service, XP009133214, Database Accession No. PREV200300546547 (Abstract).
Dow et al., "Biofilm Dispersal in Xanthomonas campestris is Controlled by Cell-Cell Signaling and is Required for Full Virulence to Plants," PNAS 100(19):10995-11000 (2003).
Erickson et al., "Pseudomonas aeruginoas Quorum-sensing Systems May Control Virulence Factor Expression in the Lungs of Patients with Cystic Fibrosis," Infection and Immunity 70(4):1783-1790 (2002).
Extended European Search Report for European Patent Application No. EP06849263 (dated Jun. 10, 2010).
International Search Report dated Nov. 20, 2007.
International Search Report for International Patent Application No. PCT/US08/06171 (dated Aug. 22, 2008).
Irie et al., "Pseudomonas aeruginosa Rhamnolipids Disperse Bordetella bronchiseptica Biofilms," FEMS Microbiol. Ltrs. 250:237-243 (2005).
Jin et al., "Biofilm-Forming Ability of Candida albicans is Unlikely to Contribute to High Levels of Oral Yeast Carriage in Cases of Human Immunodeficiency Virus Infection," J. Clin. Microbiol. 41(7):2961-2967 (2003).
Marques et al., "A Fatty Acid Messenger is Responsible for Inducing Dispersion in Microbial Biofilms," J. Bacteriol. 191(5):1393-1403 (2009).
Marques et al., "Induction of Biofilm Dispersion in Multiple Bacterial Species in Response to a Common Inducer," American Society for Microbiology (abstract).
Material Safety Data Sheet: Asiatic Acid, Sigma-Aldrich, pp. 1-5 (2010).
McDonnell et al, "Antiseptics and Disinfectants: Activity, Action, and Resistance," Clinical Microbiology Reviews, vol. 12, No. 1, pp. 147-179 (1999).
McLean et al., "Evidence of Autoinducer Activity in Naturally Occurring Biofilms," FEMS Microbiol. Ltrs. 154:259-263 (1997).
McLean et al., "Quorum Sensing and Chromobacterium violaceum: Exploitation of Violacein Production and Inhibition for the Detection of N-acylhomoserine Lactones," Microbiology 143:3703-3711 (1997).
Miller et al., "Quorum Sensing in Bacteria," Annu. Rev. Microbiol. 55:165-199 (2001).
Mireles et al., "*Salmonella enterica* Serovar Typhimurium Swarming Mutants with Altered Biofilm-Forming Abilities: Surfactin Inhibits Biofilm Formation," J. Bacteriol. 183(20):5848-5854 (2001).
Monteiro et al., "Molecular and Structural Characterization of the Biosurfactant Produced by Pseudomonas aeruginosa DAUPE 614," Chemistry and Physics of Lipids 147:1-13 (2007).
Ramage et al., "Inhibition of Candida Albicans Biofilm Formation by Farnesol, a Quorum-Sensing Molecule," Applied and Environmental Microbiology 68(11):5459-63 (2002).
Rashid et al., "Polyphosphate Kinase is Essential for Biofilm Development, Quorum Sensing, and Virulence of Pseudomonas aeruginosa," Proc Nat'l Acad Sci 97(17):9636-41 (2000).
Rice et al., "Biofilm Formation and Sloughing in Serratia marcescens are Controlled by Quorum Sensing and Nutrient Cues," J. Bacteriol. 187(10):3477-3485 (2005).
Ryan et al., "Diffusible Signals and Interspecies Communication in Bacteria," Microbiology 154:1845-1858 (2008).
Sauer et al., "Pseudomonas aeruginosa Displays Multiple Phenotypes During Development as a Biofilm," Journal of Bacteriology 184(4):1140-54 (2002).
Smith et al., "Induction and Inhibition of Pseudomonas aeruginosa Quorum Sensing by Synthetic Autoinducer Analogs," Chemistry & Biology 10:81-89 (2003).
Stoodley et al., "Biofilms as Complex Differentiated Communities," Annual Review of Microbiology 56:187-209 (2002).
Tagliente et al., Abstract Q-20, "Development and Dispersion of Pseudomonas Aeruginosa Biofilms," ASM 101st General Meeting, Orlando, Florida (May 21, 2001), Biosciences Information Service, XP009133213, Database Accession No. PREV200200233614 (Abstract).
Thompson et al., "Chemical Reactions Involved in the Deep-fat Frying of Foods. VII. Identification of Volatile Decomposition Products of Trilinolein," Journal of the American Oil Chemists' Society 55:897-901 (1978).
Wang et al., "A Bacterial Cell-Cell Communication Signal with Cross-Kingdom Structural Analogues," Molecular Microbiology, vol. 51, No. 3, pp. 903-912 (2004).
Zhang et al., "Blocking of Candida Albicans Biofilm Formation by Cis-2-Dodecenoic Acid and Trans-2-Dodecenoic Acid," Journal of Medical Microbiology 60:1643-50 (2011).
Zhang et al., Effect of a Pseudomonas Rhamnolipid Biosurfactant on Cell Hydrophobicity and Biodegradation of Octadecane, Appl. Environ. Microbiol. 60(6):2101-2106 (1994).

\* cited by examiner

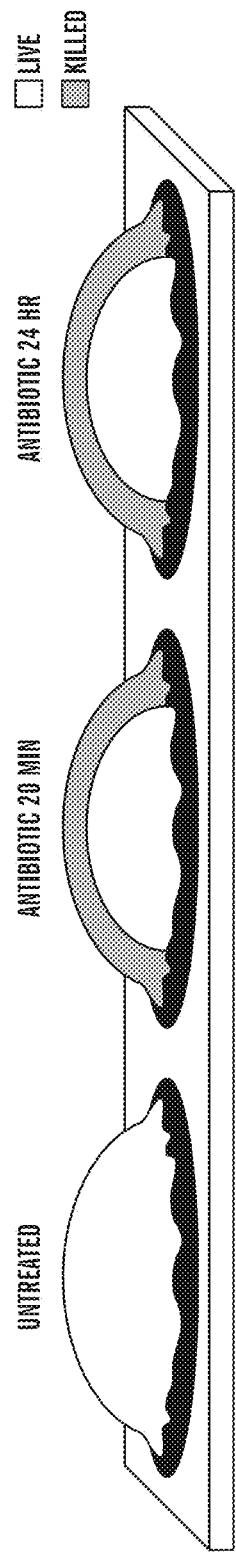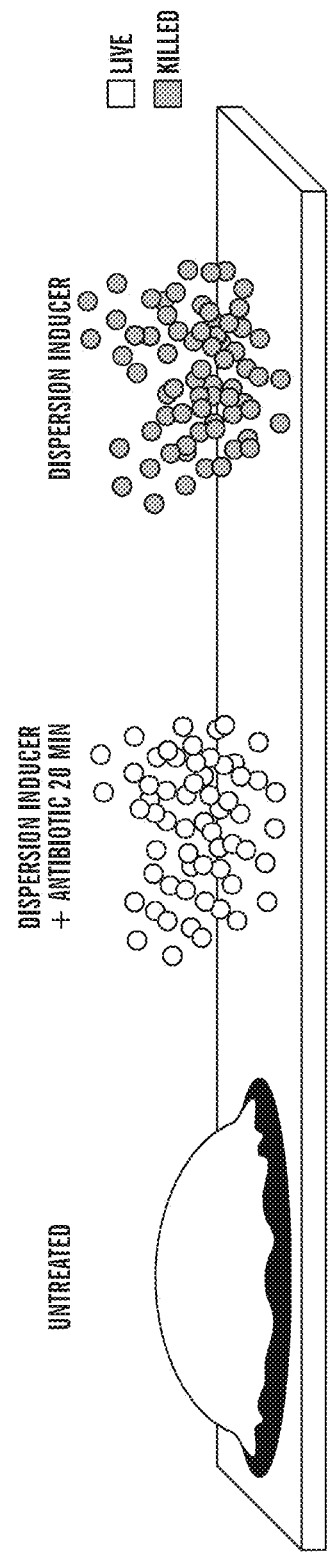
FIG. 1A
FIG. 1B

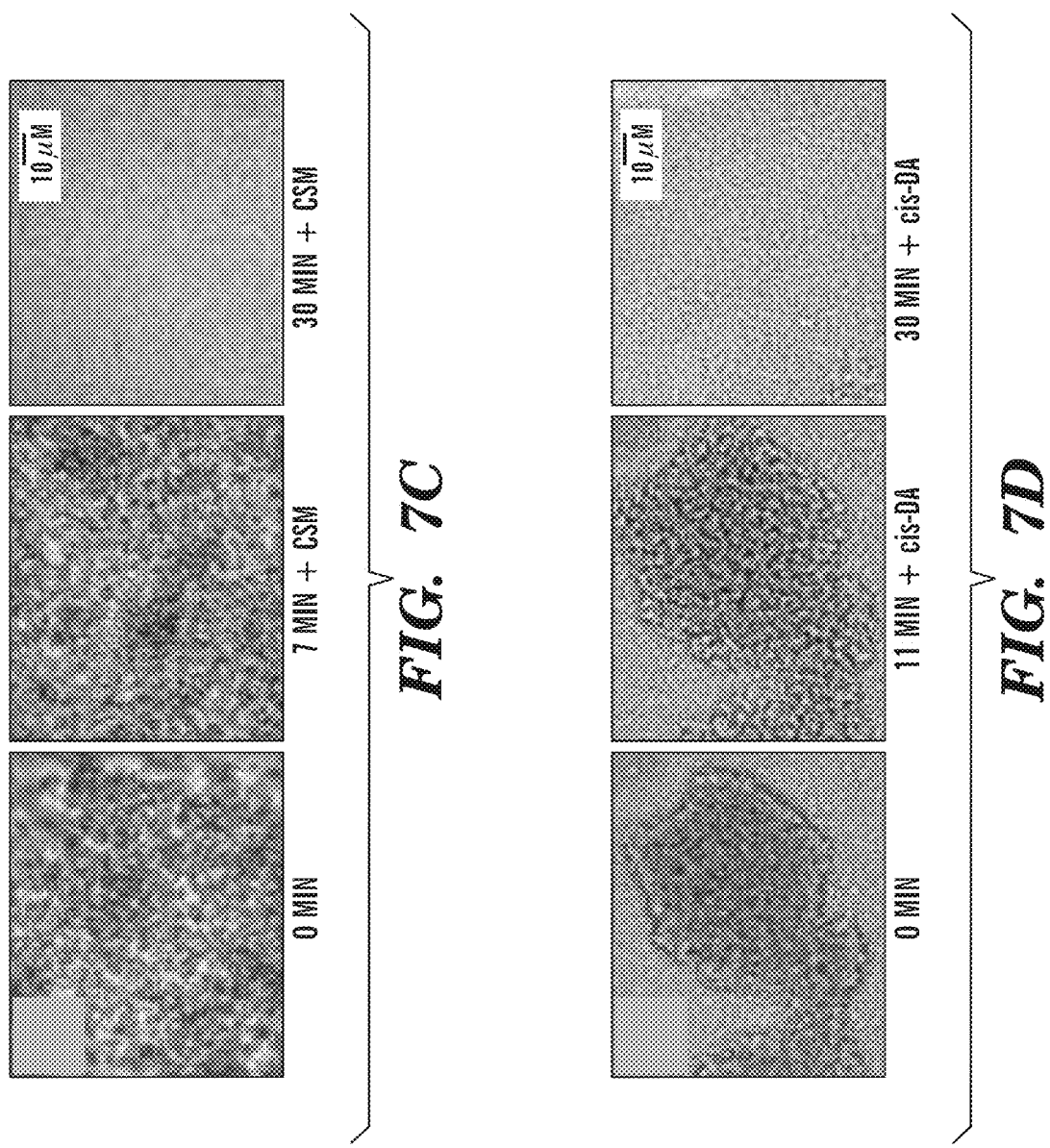

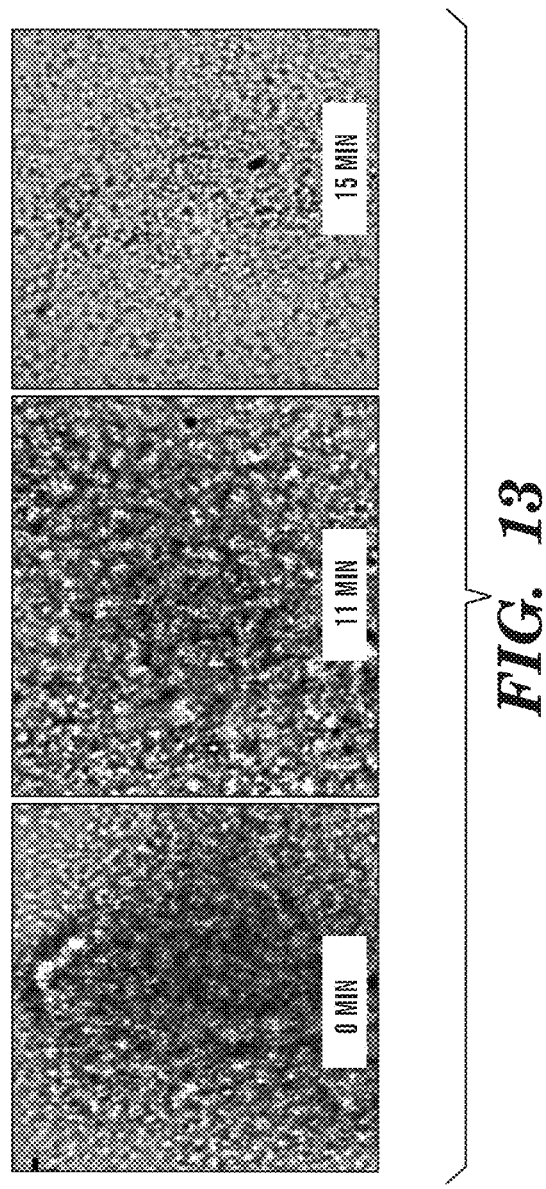

INDUCTION OF A PHYSIOLOGICAL DISPERSION RESPONSE IN BACTERIAL CELLS IN A BIOFILM

CROSS REFERENCE TO RELATED APPLICATIONS

This application is a divisional of U.S. patent application Ser. No. 13/945,207, filed Jul. 18, 2013, now U.S. Pat. No. 10,654,140, issued May 19, 2020, which is a divisional of U.S. patent application Ser. No. 12/152,347, filed May 14, 2008, now U.S. Pat. No. 8,513,305, issued Aug. 20, 2013, which claims the benefit of U.S. Provisional Patent Application Ser. Nos. 60/917,791, filed May 14, 2007, and 61/018,639, filed Jan. 2, 2008, which are hereby incorporated by reference in their entirety.

STATEMENT OF GOVERNMENT SUPPORT

This invention was made with government support under grant numbers NSF MCB-0321672 and NIH R15AI055521-01 awarded by NIH and NSF. The government has certain rights in this invention.

FIELD OF THE INVENTION

The present invention is directed to a method of inducing a physiological dispersion response in bacterial cells in a biofilm.

BACKGROUND OF THE INVENTION

Due to the compact nature of biofilm structures, the presumed reduced physiological state of biofilm bacteria and the protection conferred by biofilm matrix polymers, natural and artificial chemical agents are unable to adequately attack and destroy infectious biofilm populations (Costerton et al., "Bacterial Biofilms in Nature and Disease," Annu. Rev. Microbiol. 41:435-464 (1987); Hoiby et al., "The Immune Response to Bacterial Biofilms," In Microbial Biofilms, Lappin-Scott et al., eds., Cambridge: Cambridge University Press (1995)). Increased antibiotic resistance is a general trait associated with biofilm bacteria. When attached, bacteria exhibit a profound resistance, rendering biofilm cells 10-1000 fold less susceptible to various antimicrobial agents than the same bacterium grown in planktonic (free floating) culture. For instance, chlorine (as sodium hypochlorite) an oxidizing biocide considered to be one of the most effective antibacterial agents, has been shown to require a 600 fold increase in concentration to kill biofilm cells of *Staphylococcus aureus* when compared to planktonic cells of the same species (Luppens et al., "Development of a Standard Test to Assess the Resistance of *Staphylococcus aureus* Biofilm Cells to Disinfectants," Appl Environ Microbiol. 68:4194-200 (2002)). Several hypotheses have been advanced to account for the extraordinary resistance of biofilm bacteria to antibiotics including: (i) reduced metabolic and divisional rates exhibited by biofilm bacteria (particularly those deep within the biofilm); (ii) the biofilm EPS matrix may act as an adsorbent or reactant, reducing the amount of agent available to interact with biofilm cells. Additionally, the biofilm structure may physically reduce the penetration of antimicrobial agents by walling off access to regions of the biofilm; (iii) biofilm cells are physiologically distinct from planktonic bacteria, expressing specific protective factors such as multidrug efflux pumps and stress response regulons (Brown et al., "Resistance of Bacterial Biofilms to Antibiotics: A Growth-Rate Related Effect?" J. Antimicrob. Chemotherapy 22:777-783 (1988); Anwar et al., "Establishment of Aging Biofilms: Possible Mechanism of Bacterial Resistance to Antimicrobial Therapy," Antimicrob. Agents Chemother. 36:1347-1351 (1992); Mah et al., "Mechanisms of Biofilm Resistance to Antimicrobial Agents," Trends Microbiol. 9:34-39 (2001); Sauer et al., "*Pseudomonas aeruginosa* Displays Multiple Phenotypes During Development as a Biofilm," J. Bacteriol. 184:1140-1154 (2002); Stewart, P. S., "Mechanisms of Antibiotic Resistance in Bacterial Biofilms," Int. J. Med. Microbiol. 292:107-113 (2002); Donlan et al., "Biofilms: Survival Mechanisms of Clinically Relevant Microorganisms," Clinical Microbiol. Reviews 15:167-193 (2002); Gilbert et al., "The Physiology and Collective Recalcitrance of Microbial Biofilm Communities," Adv. Microb. Physiol. 46:202-256 (2002); Gilbert et al., "Biofilms In vitro and In vivo: Do Singular Mechanisms Imply Cross-Resistance?" J. Appl. Microbiol. Suppl. 98S-110S (2002)). As detailed molecular studies emerge, it is becoming apparent that each of these factors plays a role in the unusual resistance of biofilms to antimicrobials. Initial treatment is usually effective in killing bacteria only at the margins of biofilm microcolonies. Bacteria deep within these microcolonies are unaffected by the antibiotic and form a nidus for continued dissemination of the infection.

Microbial biofilms in infections and in industrial systems present significant problems due to their recalcitrance to effective treatment.

Detachment is a generalized term used to describe the removal of cells (either individually or in groups) from a biofilm or substratum. Bryers, J. D., "Modeling Biofilm Accumulation," In: Physiology Models in Microbiology. Bazin et al., eds., Boca Raton, Fla., Vol. 2, pp. 109-144 (1988) categorized four distinct detachment mechanisms by which bacteria detach from a biofilm. These are: abrasion, grazing, erosion, and sloughing. These mechanisms have been described principally from the point of view of the chemical and physical environment acting upon biofilm bacteria. Active detachment as a physiologically regulated event has been hinted at by many authors, but few studies have been performed to demonstrate a biological basis for detachment of bacteria from a biofilm.

One study on the physiological regulation of detachment was carried out by Peyton et al., "Microbial Biofilms and Biofilm Reactors," Bioprocess Technol. 20:187-231 (1995) on *P. aeruginosa*. In their work, it was observed that substrate limitation resulted in a decrease in the detachment rate, presumably a result of reducing the growth rate. Allison et al., "Extracellular Products as Mediators of the Formation and Detachment of *Pseudomonas fluorescens* Biofilms," FEMS Microbiol. Lett. 167:179-184 (1998) showed that following extended incubation, *P. fluorescens* biofilms experienced detachment, coincident with a reduction in EPS. In *Clostridium thermocellum*, the onset of stationary phase has been correlated with increased detachment from the substratum (Lamed et al., "Contact and Cellulolysis in *Clostridium thermocellum* via Extensive Surface Organelles," Experientia 42:72-73 (1986)). It has been postulated that starvation may lead to detachment by an unknown mechanism which allows bacteria to search for habitats richer in nutrients (O'Toole et al., "Biofilm Formation as Microbial Development," Ann. Rev. Microbiol. 54:49-79 (2000)).

The transition from a flowing system to a batch culture system has been observed by many labs to result in biofilm detachment. One lab has observed reproducible detachment of biofilm cells of *P. aeruginosa* when flow is arrested in a continuous culture system (Davies, D. G., "Regulation of Matrix Polymer in Biofilm Formation and Dispersion," In Microbial Extracellular Polymeric Substances, pp. 93-112, Wingender et al., eds., Berlin: Springer (1999)).

The release of degradative enzymes has been proposed by others. One such example is found with the gram-positive organism *Streptococcus mutans* which produces a surface protein releasing enzyme (SPRE), shown to mediate the release of proteins from the cell envelope (Lee et al., "Detachment of *Streptococcus mutans* Biofilm Cells by an Endogenous Enzymatic Activity," Infect. Immun. 64:1035-1038 (1996)). Boyd et al., "Role of Alginate Lyase in Cell Detachment of *Pseudomonas aeruginosa*," Appl. Environ. Microbiol. 60:2355-2359 (1995) showed that over-expression of alginate lyase causes the degradation of alginate. When a mucoid strain of *P. aeruginosa* was induced to over-express alginate lyase, cells were more easily removed by gentle rinsing from solid medium.

Cell density dependent regulation may also be responsible for the release of enzymes which can degrade biofilm matrix polymers allowing bacteria to disperse from a biofilm. It has been observed at the Center for Biofilm Engineering at Montana State University, USA (Davies, D. G. and Costerton, J. W.) and in the laboratories of Dr. Lapin-Scott at the University of Exeter, UK, that when certain bacteria (including *P. aeruginosa*) reach high cell densities in biofilm cell clusters, the bacteria often undergo a detachment event. Mutants of *P. aeruginosa* which lacked the ability to synthesize the quorum sensing autoinducer $3OC_{12}$-HSL, were susceptible to detachment following treatment with mild detergent (Davies et al., "The Involvement of Cell-to-Cell Signals in the Development of a Bacterial Biofilm," Science 280:295-298 (1998)). Other investigators have demonstrated that homoserine lactones may play a role in detachment. Lynch et al., "Investigation of Quorum Sensing in *Aeromonas hydrophila* Biofilms Formed on Stainless Steel", In: Biofilms—The Good, the Bad and the Ugly, Wimpenny et al., eds. Bioline, Cardiff. pp. 209-223 (1999) reported an increase in detachment of *Aeromonas hydrophila* from biofilms and Puckas et al., "A Quorum Sensing system in the Free-Living Photosynthetic Bacterium *Rhodobacter sphaeroides*," J. Bacteria 179:7530-7537 (1997) reported that homoserine lactone production was negatively correlated with cell cluster formation in *Rhodobacter sphaeroides*.

It has been recognized that *P. aeruginosa* biofilms do not develop into macroscopic biofilm structures in batch culture flasks (at the glass liquid interface). Yet, when medium is pumped continuously through such a flask, (as in a chemostat) a luxurious biofilm develops completely coating the glass surface. When flow is halted in such a system, the biofilm sloughs after a number of days, generally around 72 hrs (Davies et al., "The Involvement of Cell-to-Cell Signals in the Development of a Bacterial Biofilm," Science 280: 295-298 (1998)). The inability of biofilms to develop in batch culture has been observed for a number of gram negative and gram-positive bacteria as well as mixed cultures of bacteria. This phenomenon demonstrates that there is some aspect of batch growth that is inhibitory to biofilm development.

During the last stage of biofilm development, the protein profile of bacteria matches more closely the protein profile of planktonic cells than it does biofilm bacteria from the previous stage, denoted maturation II (see FIG. 3 of the current application, and Sauer et al., "*Pseudomonas aeruginosa* Displays Multiple Phenotypes During Development as a Biofilm," J. Bacteriol. 184:1140-1154 (2002)).

Due to the compact nature of biofilm structures, the presumed reduced physiological state of biofilm bacteria and the protection conferred by biofilm matrix polymers, current natural and artificial chemical agents are unable to adequately attack and destroy infectious biofilm populations (Costerton et al., "Bacterial Biofilms in Nature and Disease," Annu. Rev. Microbiol. 41:435-464 (1987); Hoiby et al., "The Immune Response to Bacterial Biofilms," In Microbial Biofilms, Lappin-Scott et al., eds., Cambridge: Cambridge University Press (1995)).

The present invention is directed to overcoming these and other deficiencies in the art.

SUMMARY OF THE INVENTION

One aspect of the present invention is directed to a composition. The composition comprises one or more dispersion inducers having the following formula:

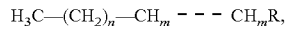

where --- is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains one or more additive components selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm.

Another aspect of the present invention relates to a method of treating or preventing a condition mediated by a biofilm in a subject. The method comprises providing a subject having, or susceptible to, a condition mediated by a biofilm produced by a microorganism, whereby the biofilm comprises a matrix and the micro-organism on a surface. Administered to the subject is a dispersion inducer comprising:

where --- is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, the condition mediated by a biofilm in the subject is treated or prevented.

An additional aspect of the present invention relates to a method of treating or inhibiting formation of a biofilm on a surface. This method involves providing a surface having or being susceptible to formation of a biofilm produced by a microorganism, where the biofilm comprises a matrix and the micro-organism on the surface. Administered to the surface is a dispersion inducer comprising:

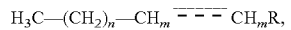

where --- is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, formation of the biofilm on the surface is treated or inhibited.

Another aspect of the present application relates to a solution comprising:

a dispersion inducer having the following formula:

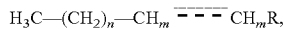

where --- is a single or double carbon-carbon bond, m is 1 or 2, n is 4 to 7, and R is a carboxylic acid, where said inducer is present at a concentration less than 0.5 percent by weight, and where said solution has a pH greater than 5.

A further aspect of the present invention is directed to a composition comprising: a component selected from one or more of the group consisting of biocides, surfactants, antibiotics, antiseptics, detergents, chelating agents, virulence factor inhibitors, gels, polymers, pastes, edible products, and chewable products. In addition, the composition includes a dispersion inducer comprising:

where --- is a single or double carbon-carbon bond, m is 1 or 2, n is 4 to 7, and R is a carboxylic acid. The inducer is formulated in a non-salt form.

The present invention is also directed to a solution which includes a cis isomer of 2-decenoic acid, where the solution is selected from the group consisting of a skin cream, a toothpaste, and a mouthwash and where the solution is substantially free of the trans isomer of 2-decenoic acid.

Another form of the present application is directed to a solution comprising: a cis isomer of 2-decenoic acid, where the solution is selected from the group consisting of a skin cream, a toothpaste, and a mouthwash and where said solution is trans isomer-free.

Another form of the present application is for a method which comprises providing contact lenses and a solution comprising a dispersion inducer at a concentration less than 0.5% by weight, said inducer comprising:

where --- is a single or double carbon-carbon bond, m is 1 or 2, n is 4 to 7, and R is a carboxylic acid, a salt, an ester, or an amide, where the ester or amide is an isostere or biostere of the carboxylic acid. The contact lenses are then treated with said solution.

A further form of the present invention is for a method which involves providing a subject with a skin condition and a solution having a pH greater than 5, where the solution comprising a dispersion inducer at a concentration less than 0.5% by weight said inducer comprising:

where --- is a single or double carbon-carbon bond, m is 1 or 2, n is 4 to 7, and R is a carboxylic acid, a salt, an ester, or an amide, where the ester or amide is an isostere or biostere of the carboxylic acid. The skin condition is then treated with the solution.

Further aspects of the present invention relate to methods of: treating subjects with burns; treating and/or preventing dental plaque, dental caries, gingival disease, and oral infection; cleaning and/or disinfecting contact lenses; treating and/or preventing acne or other biofilm-associated skin infections on the skin of a subject, and treating and/or preventing a chronic biofilm-associated disease in a subject. The methods involve administering the dispersion inducer according to the present invention, under conditions effective to accomplish each respective task. Advantageously, the biofilm dispersion inducer is highly bioactive on the microorganisms within the biofilm, and, therefore, the pharmaceutically acceptable formulation need not be chemically or mechanically active to disrupt the matrix directly. Thus, the composition may have a mild pH and be non-irritating.

The present invention also relates to a composition comprising one or more dispersion inducers and one or more additive components. These additive components are selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect to disrupt the matrix.

Another aspect of the present invention relates to a method of treating or preventing a condition mediated by a biofilm in a subject. This method involves providing a subject having, or susceptible to, a condition mediated by a biofilm produced by a microorganism, whereby the biofilm comprises a matrix and the micro-organism on a surface. A dispersion inducer is administered to the subject under conditions effective for the dispersion inducer to selectively act on the microorganism and have a suitable biological response without a required direct effect on the matrix, whereby the condition mediated by a biofilm in the subject is treated or prevented.

A further embodiment of the present application is directed to a method of treating or inhibiting formation of a biofilm on a surface. This involves providing a surface having or being susceptible to formation of a biofilm produced by a microorganism, whereby the biofilm comprises a matrix and the micro-organism on the surface. A dispersion inducer is administered to the surface under conditions effective for the dispersion inducer to selectively act on the microorganism and have a suitable biological response without a required direct effect on the matrix, whereby formation of the biofilm on the surface is treated or inhibited.

The present invention addresses the "biofilm problem" by artificially inducing bacteria to undergo physiological process of biofilm dispersion. The ability to induce dispersion will allow the control of biofilms directly and will improve existing treatments with biocides, topical antibiotics, detergents, etc. The examples of situations in which artificial dispersion would be of benefit include improved cleaning of contact lenses and teeth, improved antiseptic activity in the home, in industry, and in the medical community and enhanced cidal activity for existing antibiotic treatments such as with burn patients infected with *Pseudomonas aeruginosa*.

BRIEF DESCRIPTION OF THE DRAWINGS

FIGS. 1A-B are schematic representations of biofilm treated with an antibiotic and/or a dispersion inducer. As shown in FIG. 1A, following treatment, only the cells on the surface of the biofilm are killed by the antibiotic. FIG. 1B is a schematic representation of a biofilm induced to disperse along with treatment with antibiotic. Dispersed cells are completely killed during the treatment.

FIG. 2A shows biofilm growing in continuous culture on a glass slide in a flow cell. FIG. 2B shows the same area of biofilm 5 minutes after the addition of the dispersion inducer. FIG. 2C shows complete disaggregation of biofilm following 30 minutes initial treatment with dispersion inducer.

FIG. 4A shows early biofilm development under flowing conditions, while FIG. 4B is the same location after flow is stopped for 72 hrs.

FIGS. 7A-D show treatment of $P.$ $aeruginosa$ mature biofilms with spent medium, CSM and cis-2-decenoic acid. As shown in FIG. 7A, at 30 min, biofilms grown in silicone tubing were exposed to spent medium or fresh medium. Bacteria in effluent were collected continuously for 100 min and cell density determined by $OD_{600}$. As shown in FIG. 7B, biofilm grown in continuous culture in silicone tubing for 4 days and switched either to fresh medium for 1 hr, or CSM for 1 hr. Extruded contents of control tube shows intact biofilm. Extruded contents of CSM-treated biofilm shows dispersion. Photomicrographs show addition of CSM to mature biofilm grown in continuous culture in a microscope-mounted flow cell, as shown in FIG. 7C. Microcolony disaggregation is shown to begin at 7 min. After 30 min exposure, the microcolony had completely disaggregated. Dispersed cells were actively motile (not visible in static image), indicating a change in phenotype compared to cells in intact microcolony (prior to CSM addition). As shown in FIG. 7D, addition of 10 µM cis-2-decenoic acid (cis-DA) to mature biofilm grown in continuous culture in a microscope-mounted flow cell. Microcolony disaggregation is shown to begin at 11 min. Complete microcolony disaggregation is shown within 30 min exposure. Control biofilms treated with carrier fluid were not affected by treatment up to 1 hr.

FIG. 10A shows optical densities of cells released from biofilm-containing microtiter plate wells. White bar, control sample treated with EPRI alone. Grey bar, sample treated with CSM. Black bars represent biofilms treated with C-18 reverse phase HPLC fractions of CSM eluted in an acetonitrile gradient from 2% to 75%. Results are the average of 16 replicate wells, error bars represent one standard deviation. Results from Student's T-test show P<0.001 for CSM and 22-minute HPLC samples. FIG. 10B shows microtiter plate biofilm dispersion bioassay comparing various concentrations of cis-2-decenoic acid to spent medium. Optical densities of cells released from biofilm-containing microtiter plate wells. Negative control wells contained $P.$ $aeruginosa$ treated with 10% ethanol in EPRI. Grey bar represents biofilms treated with spent medium. Black bars represent biofilms treated with increasing concentrations of cis-2-decenoic acid in 10% ethanol. Results are the average of 16 replicate wells, error bars represent one standard deviation. Student's T-test indicated P<0.001 for all cis-2-decenoic acid samples compared to control. FIG. 10C shows the structure of cis-2-decenoic acid.

FIG. 12A shows product ion mass peaks for the 171 M/Z molecule detected in active HPLC CSM fraction and for synthetic cis-2-decenoic acid. Y-axis indicates intensity; X-axis indicates M/Z in positive ion mode. CSM sample matches peaks from synthetic cis-2-decenoic acid. Note that in mass spectrometry, peak intensity is not a direct indication of concentration. FIG. 12B shows GC-MS spectrum of *P. aeruginosa* CSM and cis-2-decenoic acid. CSM sample Peak at 15.9 min, indicates solvent carrier. Y-axis indicates intensity; X-axis indicates time in minutes. FIG. 12C shows FT-IR spectrum of *P. aeruginosa* CSM and cis-2-decenoic acid. Y-axis indicates absorbance; X-axis indicates reciprocal centimeters.

FIG. 13 shows the addition of 10 µM cis-2-decenoic acid (cis-DA) to mature biofilm grown in continuous culture in a microscope-mounted flow cell. Microcolony disaggregation is shown to begin at 11 min. Complete microcolony disaggregation is shown within 15 min exposure. Control biofilms treated with carrier fluid were not affected by treatment up to 1 hr.

DETAILED DESCRIPTION OF THE INVENTION

Figure 2C:
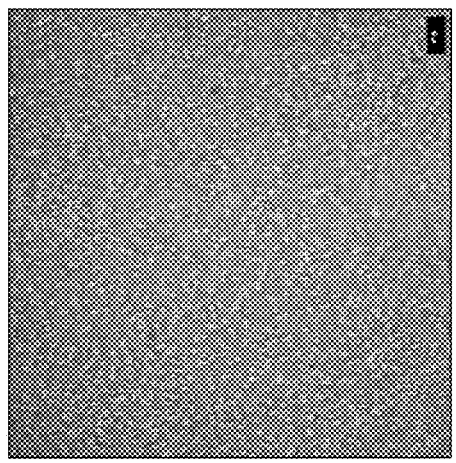
FIGS. 2A-C depict the effect of addition of chloroform extracted spent culture medium (CSM) which contains a dispersion inducing compound, to mature biofilms of *Pseudomonas aeruginosa*.

One aspect of the present invention is directed to a composition. The composition includes one or more dispersion inducers comprising:

where $\overline{---}$ is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains one or more additive components selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm. In achieving this result, the dispersion inducer of the present invention can act in preference directly on the matrix. Alternatively, the dispersion inducer can act on the microorganism which, in turn, acts to disrupt the matrix. This effect may also involve not relying on a direct effect on the matrix. Typically, the biofilm inducer will have no effect on the matrix directly or be present at a concentration where no direct effect on the matrix is evident. On the other hand, the range of effective concentrations suggest a biochemical response mechanism in the microorganisms, wherein the dispersion inducer mimics an intercellular communication composition. The composition acts to induce a dispersion response by the bacteria, which in turn is responsible for release of the bacteria from the biofilm. Additionally, the composition is able to act on bacteria not in a biofilm (planktonic bacteria), inducing these bacteria to mount a physiological response which prevents the formation of a biofilm. Additional components of a composition may be directed to disrupting or removing the matrix from the surface or substrate. For example, the composition may comprise a dentifrice adapted to abrasively remove plaque from teeth.

The R group of the above inducer may be selected from the group consisting of:

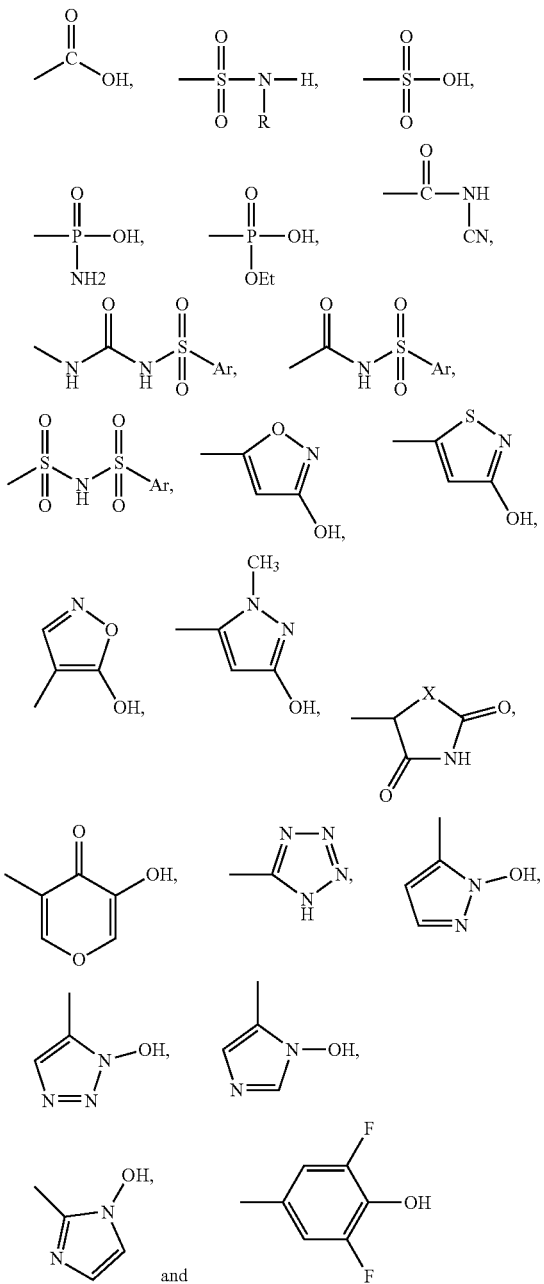

Alternatively, R can be a homoserine lactone or a furanone group. The composition also includes an additive component such as one or more of biocides, surfactants, antibiotics, antiseptics, detergents, chelating agents, virulence factor inhibitors, gels, polymers, pastes, edible products, or chewable products.

The dispersion inducer of the present invention desirably comprises 7-10 carbon atoms. It is preferred that this inducer be a carboxylic acid (e.g., a monounsaturated fatty acid). It is more preferred that the dispersion inducer comprise:

Suitable non-salt forms of this dispersion inducer being the following respective cis- and trans-isomers:

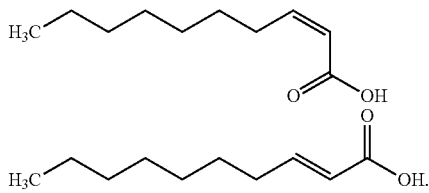

Of these, the cis isomer is preferred.

Other suitable alkanoic acids include hexanoic acid, heptanoic acid, octanoic acid, nonanoic acid, decanoic acid, undecanoic acid, dodecanoic acid, tridecanoic acid, tetradecanoic acid, pentanoic acid, hexadecanoic acid, heptadecanoic acid, octadecanoic acid, and nonadecanoic acid.

Useful alkenoic acids include 2-hexenoic acid, 2-heptenoic acid, 2-octenoic acid, 2-nonenoic acid, 2-undecenoic acid, 2-dodecenoic acid, 2-tridecenoic acid, 2-tetradecenoic acid, 2-pentadecenoic acid, 2-hexadecenoic acid, 2-heptadecenoic acid, 2-octadecenoic acid, and 2-nonadecenoic acid. These may be cis or trans isomers.

The composition of the present invention can be formulated at a number of pH ranges, to treat different types of bacteria, as follows: 1.5 to 4.5 for acid loving bacteria; 4.5 to 8.0 for acid tolerant bacteria; 6.8 to 7.4 for substantially neutral pH loving bacteria; and 8.0 to 9.8 for alkali tolerant bacteria. An essentially neutral pH is particularly desirable for subjects with acid reflux. The concentration of the dispersion inducer can be 0.01 µM to 30 mM.

The composition can be entirely or substantially (i.e. less than 10 wt %) ethanol free and/or formaldehyde free.

A surface (or substrate) coated with the composition is also encompassed by the present invention.

Another aspect of the present invention relates to a method of treating or preventing a condition mediated by a biofilm in a subject. The method comprises providing a subject having, or susceptible to, a condition mediated by a biofilm produced by a microorganism, whereby the biofilm comprises a matrix and the micro-organism on a surface. Administered to the subject is a dispersion inducer comprises:

$$H_3C-(CH_2)_n-CH_m \overline{\phantom{---}} CH_mR,$$

where --- is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, the condition mediated by a biofilm in the subject is treated or prevented. The method of dispersing the biofilm may further include administering to the biofilm, in conjunction with administering the dispersion inducer, an antimicrobial treatment. The treatment can be the administration of biocides (e.g., hydrogen peroxide), surfactants, antibiotics, antiseptics, detergents, chelating agents, virulence factor inhibitors, gels, polymers, pastes, edible products, chewable products, ultrasonic treatment, radiation treatment, thermal treatment, and/or mechanical treatment.

An additional aspect of the present invention relates to a method of treating or inhibiting formation of a biofilm on a surface. This method involves providing a surface having or being susceptible to formation of a biofilm produced by a microorganism, where the biofilm comprises a matrix and the micro-organism on the surface. Administered to the surface is a dispersion inducer comprising:

$$H_3C-(CH_2)_n-CH_m \overline{\phantom{---}} CH_mR,$$

where --- is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, formation of the biofilm on the surface is treated or inhibited.

In one embodiment, the surface to be treated includes indwelling medical devices, such as catheters, respirators, and ventilators. In addition, the surface can be in implanted medical devices, including stents, artificial valves, joints, pins, bone implants, sutures, staples, pacemakers, and other temporary or permanent devices. The dispersion inducer of the present invention can also be included in surgical glue. In another embodiment, the surface to be treated includes drains, tubs, kitchen appliances, countertops, shower curtains, grout, toilets, industrial food and beverage production facilities, flooring, and food processing equipment. In a further embodiment, the surface to be treated is a heat exchanger surface or a filter surface. Thus, treatment provides a means for reducing the degree of bio fouling of the heat exchanger or filter. In a final embodiment, the surface to be treated is a marine structure which includes boats, piers, oil platforms, water intake ports, sieves, and viewing ports. The surface can alternatively be associated with a system for water treatment and/or distribution (e.g., a system for drinking water treatment and/or distributing, a system for pool and spa water treatment, a system for treatment and/or distribution of water in manufacturing operations, and a system for dental water treatment and/or distribution). The surface can also be associated with a system for petroleum drilling, storage, separation, refining and/or distribution (e.g., a petroleum separation train, a petroleum container, petroleum distributing pipes, and petroleum drilling equipment). The dispersion inducer can also be included in formulations directed at reducing or eliminating biofilm deposits or bio fouling in porous medium, such as with oil and gas bearing geological formations. The treatment may be accomplished by applying a coating, such as paint, to the surface.

The method of inhibiting formation of a biofilm on a surface may further involve administering to the surface, in conjunction with administering the dispersion inducer, an antimicrobial treatment. The treatment can be administration of biocides, surfactants, antibiotics, antiseptics, disinfectants, medicines, detergents, chelating agents, virulence factor inhibitors, ultrasonic treatment, radiation treatment, thermal treatment, and mechanical treatment. In one embodiment, the dispersion inducer and the antimicrobial treatment are administered simultaneously. In another embodiment, the dispersion inducer and antimicrobial treatment are administered separately.

The dispersion inducer can be impregnated in a surface in order to inhibit formation of a biofilm on the surface. Alternatively, the dispersion inducer can be in a copolymer or a gel coating over the surface.

The present invention also relates to a method of treating subjects with burns. The method involves administering the dispersion inducer according to the present invention, under conditions effective to treat burns in the subject. A specific application of the invention provides a topical dressing for burn patients comprising dispersion inducing molecules or their natural or synthetic analogs to prevent the development of infectious biofilms or to disperse the cells of existing infectious biofilms.

The present invention further relates to a method of treating and/or preventing dental plaque, dental carries, gingival disease, periodontal disease, and oral infection in a subject. The method involves treating the oral cavity of the subject with the dispersion inducer according to the present invention. Treating can be carried out with a dentifrice, mouthwash, dental floss, gum, strip, toothpaste, a toothbrush containing the dispersion inducer, and other preparations containing the dispersion inducer. The composition may also contain other compounds known in the dental arts that are typically added to dental compositions. For example, the dispersion inducer composition may also include fluoride, desensitizing agents, anti-tartar agents, antibacterial agents, remineralization agents, whitening agents, and anti-caries agents.

The amount of dispersion inducer present will vary dependent on the dental composition that contains the dispersion inducer. It has been found that the dispersion inducer is active over a wide range of concentrations against oral bacteria. For instance, the dispersion inducer may be present in an amount ranging from 0.1 nM to 10 mM. However, lower and higher concentrations may be used depending on the dental composition, the other components present in the dispersion inducer composition, and various other factors appreciated by those of skill in the art. The known properties of the dispersion inducer, such as its fatty acid characteristics and its hydrophobicity, will assist a skilled artisan in determining how much of the dispersion inducer should be used, determining how the compound will chemically interact with other components, and providing other useful information about the compound.

Specific dental applications and dental compositions are contemplated in this invention. In this regard, the invention relates to a toothbrush containing a dispersion inducer composition. Toothbrushes, as is well known in the art, contain a plurality of bristles and a solid support on which the bristles are mounted, where the solid support includes a brush head having a plurality of tuft holes that receive the bristles. Variations and modifications of the basic toothbrush are well known in the art. See, for example, U.S. Pat. No. 7,251,849, herein incorporated by reference in its entirety.

The dispersion inducer of this invention has a chemical formula as set forth above. Additional components that may be included in the dispersion inducer compositions are also set forth above. The dispersion inducer composition may be incorporated in the various parts of the toothbrush by means known in the art. For instance, the dispersion inducer composition may be contained in the tuft holes of the toothbrush. See U.S. Pat. No. 5,141,290, herein incorporated by reference in its entirety, for an example of how a composition can be contained within the tuft holes of a toothbrush. Alternatively, the dispersion inducer composition may be coated or embedded in the bristles of the toothbrush.

Other parts of the toothbrush may also be coating or embedded with the dispersion inducer composition, including any parts of the toothbrush that supplement the bristles and are designed to be contacted with the oral cavity. For example, it is common for toothbrushes to contain rubber paddles, tongue cleaners, or other pieces extended from the head for the purposes of being contacted with the tooth, tongue, gums, or other areas of the oral cavity. These parts may be embedded with the dispersion inducer composition and, optionally, a surfactant, biocide, and/or other additive discussed above.

To assist in controlling the release of the dispersion inducer from the toothbrush, the dispersion inducer composition may contain an agent that interacts with the dispersion inducer to assist in the controlled release. The agent may interact with the dispersion inducer in a manner that the release is either accelerated or prolonged, depending on the desired use. The level of controlled release can also depend on how easily or difficult the dispersion inducer adheres to the portion of the toothbrush that it is applied to. In a preferred embodiment, the dispersion inducer is slowly released from the toothbrush over repeated brushings. Agents that enable the slow release of an active ingredient are well known to those of skill in the art.

The controlled release may also be effectuated by encapsulating the dispersion inducer in an encapsulated system that allows a controlled release. In this embodiment, the dispersion inducer composition is preferably in the form of a plurality of small microspheres that encapsulate the dispersion inducer. The microspheres can have an outer coating of dissolvable material that enables the dispersion inducer to slowly release over repeated brushings. Suitable microspheres include those disclosed in U.S. Pat. No. 5,061,106, herein incorporated by reference in its entirety.

This invention also relates to a toothpaste composition that contains (a) fluoride and/or a remineralization agent; (b) an orally-accepted vehicle; and (c) a dispersion inducer composition. The dispersion inducer of this invention has a chemical formula as set forth above. Additional components that may be included in the dispersion inducer compositions are also set forth above. Often, toothpastes also contain sodium lauryl sulfate or other sulfates.

Fluoride in its various forms is a common active ingredient in toothpaste to prevent cavities and promote the formation of dental enamel and bones. Any fluoride source, such as fluoride salts may be used in the toothpaste of this invention. Preferably, the fluoride is sodium fluoride (NaF) or sodium monofluorophosphate ($Na_2PO_3F$). Typically, the amount of fluoride present in the toothpaste ranges from 100 to 5000 parts per million fluoride ion, preferably 1000 to 1100 parts per million.

In certain instances, it is preferable to replace or supplement the fluoride with a remineralization agent. Remineralization, in the context of dental usage, generally refers to treating the teeth so as to prevent dental caries, or decrease their chance of occurring, and otherwise enhance the teeth so that they can return to their original, healthy state. While fluoride can be considered a remineralization agent, other agents often take the place of fluoride or supplement fluoride to provide the toothpaste with a stronger cleansing or remineralization properties. Common remineralization agents are calcium salts, such as calcium phosphate, calcium sulfate, anhydrous calcium sulfate, calcium sulfate hemihydrate, calcium sulfate dihydrate, calcium malate, calcium tartrate, calcium malonate, and calcium succinate. Hydroxyapitate nanocrystals and zinc compounds have also been shown to be effective remineralization agents.

The orally-accepted vehicle may be any vehicle known in the art that can be used to deliver the fluoride and/or remineralization agent, and dispersion inducer to the teeth of a patient. The orally-accepted vehicle may also be glycerin, propylene glycol, polyethylene glycol, triglyceride, diglyceride, mineral oil, organic oils, essential oils, fatty vegetable oils, and combinations thereof. Often these vehicles are used in combination with water or a water-based solvent.

The toothpaste composition may contain other components of toothpastes well known in the art. For instance, the toothpaste composition may contain baking soda, enzymes, vitamins, herbs, calcium compounds such as calcium sodium phosphosilicate, coloring agents, and/or flavoring agents. Desensitizing agents may also be added. As known in the art, desensitizing agents can reduce sensitivity in teeth by treating sensitivities caused by demineralization or suppressing the sensitivity symptoms by desensitizing the nerves. The composition may also contain an antibacterial or an antiplaque agent. Antibacterial agents are preferable included in the composition to prevent gingivitis, periodontitis, and other oral diseases. Suitable antibacterial agents include triclosan, zinc chloride, chlorhexidine, benzthonium chloride, and cetyl pyridinium chloride.

This invention also relates to an oral composition for treating and/or preventing dental plaque, gingival diseases, periodontal diseases, and/or oral infection. The oral composition contains an orally-accepted vehicle and a dispersion inducer composition. The dispersion inducer of this invention has a chemical formula as set forth above. Additional components that may be included in the dispersion inducer compositions are also set forth above.

The oral composition can be various compositions in the field of dental hygiene known to those in the art. For instance, the oral composition may be a mouthwash, breath spray, dentifrice, tooth powder, whitening strips, or prophylaxis paste. As is well known in the art, mouthwashes are commonly used to help remove mucous and food particles in the oral cavity or throat. Mouthwashes typically contain antiseptic and/or anti-plaque components to kill the bacterial plaque that causes caries, gingivitis, and bad breath. They can also contain anti-cavity components, such as fluoride, to protect against tooth decay. Suitable mouthwash components may be found in U.S. Pat. No. 5,968,480, herein incorporated by reference in its entirety.

Likewise, the same or similar antiseptic, anti-plaque, and anti-cavity components can be used in breath sprays, dentifrices, including gel dentifrices, tooth powders, whitening strips, and prophylaxis pastes. Suitable breath spray compositions are disclosed in U.S. Pat. No. 7,297,327; suitable tooth powder compositions, such as those used in tooth bleaching compositions, are disclosed in U.S. Pat. No. 5,989,526; suitable whitening strips are disclosed in U.S. Pat. No. 6,514,483; and suitable dentifrices and prophylaxis paste compositions, including dental abrasives, are disclosed in U.S. Pat. No. 5,939,051, all of which are herein incorporated by reference in their entirety.

The ingredients of orally-accepted vehicle are similar to those discussed above. However, the orally-accepted vehicle will vary depending on the desired consistency and desired end product of the oral composition. For instance, a mouthwash is in a liquid form, so liquid carriers, typically carriers having a high percentage of water, should be used. On the other hand, a gel dentifrice should be in the form of a gel and would utilize gelling agents or other carriers that enable the final product to be in the form of a gel. The orally-accepted vehicle should have properties that both allow the dispersion inducer composition to be delivered while also providing the final product with the desired consistency.

The oral composition may also be in the form of chewing gum, a breath strip, a lozenge, or a breath mint. Chewing gum is typically a combination of a water-insoluble phase, or gum base, and a water-soluble phase of sweeteners, flavoring and/or food coloring. Other components may also be added to the gum, including breath-freshening additives such as zinc and phosphate salts, teeth-whitening additives such as silica, and plaque-reducing additives to moderate dental plaque. Suitable gum compositions may be found in U.S. Pat. Nos. 6,416,744 and 6,592,849, both of which are herein incorporated by reference in their entirety.

Breath strips are similar to chewing gum, except that the strips are designed to dissolve in the mouth, often absorbed through the tongue. The strips can deliver bioactive ingredients to freshen the mouth as well functional bioactive ingredients, such as vitamins, minerals, supplements, pharmaceuticals, and vaccines.

Lozenges and breath mints are typically discoid-shaped solids that contain a therapeutic agent in a flavored base. The base may be a hard sugar candy, glycerinated gelatin or combination of sugar with sufficient mucilage to give the composition requisite form. The dispersion inducer may represent the therapeutic agent, or it may be added in addition to therapeutic agents known in the art. Suitable lozenge and breath mint compositions are disclosed in U.S. Pat. No. 7,025,950, herein incorporated by reference in its entirety.

The oral composition may also be in the form of a cleaning preparation for a dental apparatus that is placed in the oral cavity. Dental apparatuses such as dentures, dental dams, and certain types of orthodontic braces are placed in the oral cavity for a period of time, and then periodically removed for cleaning. The cleaning composition used to clean the dental apparatuses should function in its customary manner of cleaning the apparatus, but may also contain therapeutic agents that can assist in treating or preventing dental plaque, gingival diseases, periodontal diseases, and oral infection when the dental apparatuses are in contact with the oral cavity. Cleaning compositions such as effervescent cleansers made with alkaline mixtures containing a chlorine compounds and the like are known in the art. Suitable cleaning compositions for dental apparatuses are disclosed in U.S. Pat. No. 3,936,385, herein incorporated by reference in its entirety. The dispersion inducer may be added to the cleaning compositions in a manner than enables it to coat the dental apparatus upon contact. After the dental apparatus has been introduced into the oral cavity, the dispersion inducer can interact with the teeth and other elements of the oral cavity in a therapeutically effective manner, i.e. to prevent dental plaque, gingival diseases, periodontal diseases, and/or oral infection.

This invention also relates to an article for oral use comprising a dental article and a dispersion inducer. The dispersion inducer has the chemical formula set forth above, and is coated on, encapsulated in, or impregnated in the dental article. Additional components that may be included in the dispersion inducer compositions are also set forth above.

Various dental articles known in the art may be used in this embodiment of the invention. In one embodiment, the dental article is a dental floss. Any fiber known in the art may be used in the dental floss. Suitable fibers include polyamides (such as nylon), polyesters, polypropylenes, polytetrafluoroethylenes, cellulose, and cotton. Nylon and polytetrafluoroethylene fibers are the most common fibers used in dental floss and represent preferred fibers. Suitable dental flosses are disclosed in U.S. Pat. Nos. 6,270,890 and 6,289,904, both of which are herein incorporated by reference in their entirety. The dispersion inducer composition may be impregnated into the fiber, coated on the fiber, or otherwise incorporated into the dental floss.

The dental floss may be coated or impregnated with a wax or other hydrophobic substance for ease of use during the flossing process. Suitable waxes include microcrystalline waxes, beeswax, paraffin waxes, carnauba waxes, and polyethylene waxes. The dispersion inducer composition may be coated onto the dental floss as part of the wax layer, as a second or additional layer in conjunction with the wax layer, or applied to the fiber as discussed above.

The dental article may be a toothpick that is impregnated with or coated with the dispersion inducer composition. Toothpicks may be made from natural products, such as wood, or artificial components, including various plastics. Suitable toothpicks are disclosed in U.S. Pat. No. 7,264,005, herein incorporated by reference in its entirety.

The dental article may also be a dental appliance such as a dental aspirator, bite block, dental dam, tongue stabilizer, tongue deflector, or any other piece of dental equipment that a dentist or dental assistant may use in the mouth of a patient. A discussion of dental appliances may be found in U.S. Pat. Nos. 4,865,545 and 5,152,686, both of which are herein incorporated by reference. The portion of the dental appliance that comes into contact with the oral cavity of a patient may be coated with the dispersion inducer composition.

The dental article may also be a dental construct, such as veneers, crowns, inlays, onlays, or bridges that are placed on the teeth. Dental constructs are typically made of metal alloys, porcelain, ceramic, amalgam, acrylate polymers, or a combination of these materials. Suitable dental constructs are disclosed in U.S. Pat. No. 7,229,286, herein incorporated by reference in its entirety. The dispersion inducer composition may be embedded in the composition used to make the dental construct. Alternatively, the dispersion inducer composition may be coated on the dental construct after it has been prepared.

This invention also relates to an aqueous composition applied to the oral cavity with the use of a dental article, comprising water and a dispersion inducer composition. Various dental articles are attached to or designed to be used with a water line so that water can be distributed through the dental article, and then routed from the dental article to the oral cavity of a subject. Suitable dental articles include dental water lines, dental water picks, and the like.

While tap water or purified water may be used in these types of dental devices, the water source may also be supplemented with additives so that the water delivers the additives to the oral cavity of the subject when used with the dental article. In this case, the additive supplemented to the water is a dispersion inducer composition.

Dental water lines and dental water picks are known in the art and commonly used by dentists and dental assistants. A discussion of different types of dental water lines and their different applications may be found in U.S. Pat. No. 5,785,523, herein incorporated by reference in its entirety. Suitable water picks are disclosed in U.S. Pat. No. 4,257,433, herein incorporated by reference in its entirety.

The present invention also relates to a method of cleaning and/or disinfecting contact lenses. The method involves treating contact lenses with a cleaning and/or disinfecting solution containing the dispersion inducer according to the present invention. The contact lens may be treated in this manner while being stored in solution or while being used in vivo. Alternatively, the dispersion inducer can be used in eye drops.

The present invention further relates to a method of treating and/or preventing acne or other biofilm-associated skin infections on the skin of a subject. The method involves treating the skin of the subject with the dispersion inducer according to the present invention under conditions effective to treat and/or prevent the acne or biofilm-associated skin infections. The dispersion inducer may be present in an ointment, cream, liniment, salves, shaving lotion, or aftershave. It may also be present in a powder, cosmetic, ointment, cream, liquid, soap, gel, cosmetic applicator, and/or solid, woven or non-woven material intended to contact or be proximate with the skin.

The present invention also relates to a method of treating and/or preventing a chronic biofilm-associated disease in a subject. The method involves administering to the subject the dispersion inducer according to the present invention under conditions effective to treat and/or prevent the chronic biofilm-associated disease. The chronic biofilm-associated diseases to be treated and/or prevented include, but are not limited to, middle ear infections, osteomyelitis, prostatitis, colitis, vaginitis, urethritis, arterial plaques, sinovial infections, infections along tissue fascia, respiratory tract infections (e.g., infections associated with lung infections of cystic fibrosis patients, pneumonia, pleurisy, pericardial infections), genito-urinary infections, and gastric or duodenal ulcer infections. For gastric or duodenal ulcers caused by *Helicobacter pylori*, the dispersion inducer will need to function at a pH of below 5.5. The dispersion inducer may be administered in combination with an antimicrobial agent, such as biocides, surfactants, antibiotics, antiseptics, detergents, chelating agents, or virulence factor inhibitors. In the case of gastric therapies, acid reducing therapies, such as antacids, proton pump inhibitors, antihistamines, and the like may also be employed.

Another aspect of the present application relates to a solution comprising:

a dispersion inducer comprises:

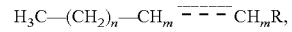

where - - - is a single or double carbon-carbon bond, m is 1 or 2, n is 4 to 7, and R is a carboxylic acid, where said inducer is present at a concentration less than 0.5 percent by weight, and where said solution has a pH greater than 5.

A further aspect of the present invention is directed to a composition comprising: a component selected from one or more of the group consisting of biocides, surfactants, antibiotics, antiseptics, detergents, chelating agents, virulence factor inhibitors, gels, polymers, pastes, edible products, and chewable products. In addition, the composition includes a dispersion inducer comprises:

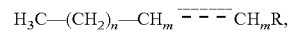

where - - - is a single or double carbon-carbon bond, m is 1 or 2, n is 4 to 7, and R is a carboxylic acid. The inducer is formulated in a non-salt form.

The present invention is also directed to a solution which includes a cis isomer of 2-decenoic acid, where the solution is selected from the group consisting of a skin cream, a toothpaste, and a mouthwash and where the solution is substantially free of the trans isomer of 2-decenoic acid. As interpreted herein, this solution is substantially free of a trans isomer if a reduction in trans isomer (without change in cis-isomer) concentration does not increase bioactivity. It is more preferred that there be a molar ratio of cis to trans of at least 2.

Another form of the present application is directed to a solution comprising: a cis isomer of 2-decenoic acid, where the solution is selected from the group consisting of a skin cream, a toothpaste, and a mouthwash and where said solution is trans isomer-free.

Another form of the present application is for a method which comprises providing contact lenses and a solution comprising a dispersion inducer at a concentration less than 0.5% by weight, said inducer comprises:

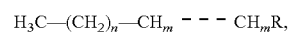

where - - - is a single or double carbon-carbon bond, m is 1 or 2, n is 4 to 7, and R is a carboxylic acid, a salt, an ester, or an amide, where the ester or amide is an isostere or biostere of the carboxylic acid. The contact lenses are then treated with said solution.

A further form of the present invention is for a method which involves providing a subject with a skin condition and a solution having a pH greater than 5, where the solution comprising a dispersion inducer at a concentration less than 0.5% by weight said inducer comprises:

where $---$ is a single or double carbon-carbon bond, m is 1 or 2, n is 4 to 7, and R is a carboxylic acid, a salt, an ester, or an amide, where the ester or amide is an isostere or biostere of the carboxylic acid. The skin condition is then treated with the solution.

The present invention also relates to a composition comprising one or more dispersion inducers and one or more additive components. These additive components are selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect to disrupt the matrix.

Another aspect of the present invention relates to a method of treating or preventing a condition mediated by a biofilm in a subject. This method involves providing a subject having, or susceptible to, a condition mediated by a biofilm produced by a microorganism, whereby the biofilm comprises a matrix and the micro-organism on a surface. A dispersion inducer is administered to the subject under conditions effective for the dispersion inducer to selectively act on the microorganism and have a suitable biological response without a required direct effect on the matrix, whereby the condition mediated by a biofilm in the subject is treated or prevented.

A further embodiment of the present application is directed to a method of treating or inhibiting formation of a biofilm on a surface. This involves providing a surface having or being susceptible to formation of a biofilm produced by a microorganism, whereby the biofilm comprises a matrix and the micro-organism on the surface. A dispersion inducer is administered to the surface under conditions effective for the dispersion inducer to selectively act on the microorganism and have a suitable biological response without a required direct effect on the matrix, whereby formation of the biofilm on the surface is treated or inhibited.

EXAMPLES

The following examples are provided to illustrate embodiments of the present invention but are by no means intended to limit its scope.

Example 1

Bacterial Strains and Media

The microorganisms used in this study included *Pseudomonas aeruginosa* PAO1 from B. H. Holloway, *Escherichia coli* (ATCC 10798), *Proteus mirabilis* (ATCC 25933), *Klebsiella pneumoniae* (ATCC 10273), *Staphylococcus aureus* (ATCC 12602), *Streptococcus pyogenes* (ATCC 19615), *Bacillus subtilis* (ATCC 6633), and *Candida albicans* (ATCC 20260) and a mixed undefined culture collected on R2A plates via airborne contamination. Except where indicated, all experiments were performed in modified EPRI medium, containing 0.005% ammonium nitrate, 0.00019% $KH_2PO_4$, 0.00063% $K_2HPO_4$ (pH 7.0), and 0.001% Hutner salts (Cohen-Bazire et al., J. Cell. Comp. Physiol. 49:35 (1957), which is hereby incorporated by reference in its entirety), supplemented with 0.2% glucose. *C. albicans* was grown in modified EPRI medium supplemented with 0.2% glucose and 0.1% peptone. *K. pneumoniae, P. mirabilis, S. aureus*, and *B. subtilis* were grown in modified EPRI medium supplemented with 0.1% peptone. *S. pyogenes* was grown in 10% Brain Heart Infusion broth.

Example 2

Preparation of *P. aeruginosa* Spent Medium

To prepare cell-free spent culture medium, 6 mL of an overnight culture of *P. aeruginosa* PAO1 grown in modified EPRI medium at 30° C. were inoculated into four liters of modified EPRI medium and incubated for 10 days at room temperature with continuous stirring. Bacterial cells were sedimented by centrifugation (Sorvall RC 5B Plus Centrifuge, GSA Rotor; Thermo Electron Co., Ashville, N.C.) at 13,000×g for 15 minutes at 4° C. The supernatant was removed and filtered under vacuum through a 0.45 µm Millipore Type HA filter (Millipore. Co., Billerica, Mass.) and subsequently, through a 0.2 µm, Acrodisc 32 mm syringe filter (PALL Co., East Hills, N.Y.). Spent medium was stored at 4° C.

Example 3

Preparation of CSM

The organic components of spent medium were extracted by adding 80 mL of chloroform to 250 mL of filtered spent medium in a separatory funnel. The chloroform fraction was removed after a separation time of 1 hr. Chloroform was evaporated at 40° C. using a Rotavapor R-3000 rotary evaporator (Biichi Laboratories, Flawil, Switzerland) and the remaining organic material was re-suspended in 6 mL of filtered nanopure water and evaporated to dryness using a Speed-Vac evaporator system (Savant Instruments, Inc., Hicksville, N.Y.) or lyophilized. These samples were then resuspended in culture medium or purified water. The final product is referred to as Chloroform extracted Spent Medium (CSM). Except where indicated, CSM was used in experiments at a final chloroform extracted organic carbon concentration 125 fold greater than found in spent medium.

Example 4

HPLC Fractionation of CSM

CSM was fractionated by High Performance Liquid Chromatography (HPLC) (Varian Prostar model 320, Varian Inc., Palo Alto, Calif.) using a C18 Microsorb-mv reverse phase column (Varian Inc.) dimensions 250×4.6 mm. The column was loaded with 100 µL of CSM and eluted in an acetonitrile/water gradient (2-75%) with a flow rate of 1 mL/min for 29 minutes. Samples were collected every minute, starting at 2 minutes. HPLC fractions were pooled and concentrated in a Speed Vac concentrator (Savant Instruments, Inc., Hicksville, N.Y.) and resuspended in 0.5 mL of modified EPRI medium or purified water. The active HPLC fraction was found to elute from the column in 70% acetonitrile/30% water. The active fraction of each HPLC separation was determined by microtiter plate dispersion bioassay.

Example 5

Microtiter Plate Dispersion Bioassay

Microtiter plate dispersion bioassays were used to test various preparations for their ability to exogenously induce biofilm dispersion. Biofilms were grown on the inside surface of microtiter plate wells using a semi-batch culture method in which the medium within each well was replaced periodically to reduce the accumulation of native dispersion inducing factors. Biofilms grown in this manner were treated with dispersion inducer or sterile medium to release cells into the bulk liquid and evaluate dispersed cell number by measuring optical density. Briefly, sterile polystyrene 96 well plates were etched with acetone for 10 seconds to create a rough surface for the attachment of microbial cells. After drying for 24 hours, plates were inoculated with 150 µL/well of overnight culture containing the test organism, previously diluted 1:20 in growth medium and incubated at 30° C. with shaking at 200 rpm. Medium in the wells was replaced every 24 hours for 5 days and every 12 hours on day 6 and day 7. Medium was then replaced after 7 hours. Dispersion induction was tested by adding 150 µL growth medium containing dispersion inducer for 1 hr at 30° C. or sterile medium as a control. Medium containing dispersed cells was then transferred by pipet to a non-etched microtiter plate and the optical density ($OD_{570}$) was determined (ELx808 Absorbance Microplate Reader; BioTek Instruments, Inc., Winooski, Vt.). Treatments consisted of spent medium, CSM, cis-2-decenoic acid, trans-decenoic acid, decanoic acid and DSF at various concentrations. Ethanol (10%) was used as a carrier for fatty acid inducer samples and was determined to have no influence on dispersion. Results from use of this method are meaningful in making comparisons of different treatments and to determine whether dispersion activity is statistically significant. Note: Microtiter plate dispersion bioassays were not suitable for determining absolute magnitude of an induced dispersion response because in a semi-batch system, control and test samples are susceptible to natural dispersion against which the activity of exogenous induction is measured. All efficiency studies were performed using biofilm tube reactor or flow-cell continuous culture systems and were based on both total cell counts and viable cell counts.

Example 6

Dispersion Bioassays in Biofilm Tube Reactors

*P. aeruginosa* PAO1 biofilm cultures were grown in tube reactors as described previously by Sauer et al. (K. Sauer, et al., J. Bacteriol. 184:1140 (2002), which is hereby incorporated by reference in its entirety). A continuous once-through tube reactor system was configured using 8 silicone reactor tubes (81.5 cm length×14 mm ID), connected to an 8-roller head peristaltic pump and medium reservoir, via additional silicone tubing. Medium was pumped through the tubing to a closed effluent medium reservoir. The assembled system was sterilized by autoclaving prior to inoculation. The silicone tubes were inoculated by syringe injection through a septum 1 cm upstream from each reactor tube, with 2 mL of overnight cultures of *P. aeruginosa* (containing approximately $1 \times 10^8$ CFU/mL). Bacterial cells were allowed to attach (static incubation) to the tubing for 1 hour, after which the flow was started at an elution rate of 10.8 mL/hr. Treatments were carried out following 96 hours of *P. aeruginosa* PAO1 biofilm cultures. The treatments were performed under continuous and static conditions.

Under continuous treatment (FIG. 17A) the influent medium was changed from fresh medium in the test lines to spent medium amended with 2% glucose, adjusted to neutrality and aerated overnight prior to addition. Control lines were switched to new lines containing fresh modified EPRI medium. Samples were collected for one minute intervals starting at time=0 min, and assayed for optical density. Spent medium was added at time=30 min. Samples were collected in test tubes on ice and were subsequently homogenized for 30 sec at 5000 rpm with a Tissue Tearor Model 985370 (Biospec Products, Inc.) to ensure separation of cells. Cell density was determined by optical density at 600 nm with an Ultrospec 3000 spectrophotometer (Amersham Pharmacia Biotech, Inc.).

Under conditions of static treatment, dispersion inducer was added by syringe injection through the inoculation port, 2 cm upstream from the beginning of the tube reactor, displacing the reactor volume with medium containing inducer. Spent medium was added directly. CSM or synthetic dispersion inducer (e.g.: cis-2-decenoic acid) was prepared in modified EPRI and added. After one hour of exposure under non-flowing conditions, an 81.5 cm length of each silicone tube reactor was cut out, the liquid fraction (containing released biofilm cells) was collected in test tubes on ice and the biofilm fraction was collected by rolling the tube on the lab bench with a metal rod to extrude the cells remaining in the lumen of the tube (K. Sauer, et al., J. Bacteriol. 184:1140 (2002), which is hereby incorporated by reference in its entirety). Samples were collected on ice, and homogenized as above. Cells numbers were determined by spread plate method on Standard Plate Count agar medium (Difco, Detroit, Mich.) or by optical density at $OD_{600}$ adjusted to cell number by calibration to a standard curve for cell number as determined microscopically by total cell count. Dispersion efficacy was calculated using either optical density or viability measurements:

$$\text{Dispersion Efficacy} = \frac{\text{Cells from Bulk Liquid} \times 100}{\text{Cells from Bulk Liquid} + \text{Cells from Biofilm}}$$

Example 7

Microscopic Analysis

A continuous-culture once-through flow cell was configured to observe the growth and development of biofilms attached to a glass substratum. The flow cell was constructed of aluminum containing a chamber 1.0 mm by 1.4 cm by 4.0 cm capped with a glass cover slip. Sterile modified EPRI medium was pumped from a 10-liter vessel through silicone tubing to the flow cell using a Masterflex 8-roller-head peristaltic pump at a flow rate of 0.13 mL/min. Flow through the chamber was laminar, with a Reynolds number of 0.17, having a fluid residence time of 4.3 min. Medium leaving the flow cell was discharged to an effluent reservoir via silicone tubing. The entire system was closed to the outside environment but maintained in equilibrium with atmospheric pressure by a 0.2-µm-pore-size gas-permeable filter fitted to each vessel. Log-phase *P. aeruginosa* (approximately $10^8$ CFU/mL) were inoculated as a 3.0 mL slug dose through a septum 4 cm upstream from the flow cell under flowing conditions. Cells attached to the inner surface of the glass cover slip were viewed by transmitted light or epi-UV illumination using an Olympus BX60 microscope and a 100× magnification A100PL objective lens or a 50× magnification ULWD MSPlan long working distance Olympus objective lens. All images were captured using a Magnafire cooled three-chip charge-coupled device (CCD) camera (Optronics Inc., Galena, Calif.) and stored as separate digital files for subsequent retrieval and analysis P. aeruginosa were grown in the flow cell for up to 12 days. Previous work by applicant has shown P. aeruginosa to develop steady-state biofilms following a continuous culture period of 7 to 9 days. Steady state is defined by no change in effluent cell counts (CFU) resulting from detached biofilm cells; in steady state, growth of the biofilm is balanced by the loss of cells through dispersion or detachment. Individual cell clusters were examined during the course of each experiment and assigned grid coordinates, which were reexamined periodically during the course of the experiments. Size measurements were taken of random cell clusters by locating the cluster nearest to a randomly selected microscope stage coordinate. Each cell cluster was measured to determine its height by focusing from the substratum through to the apex of the cluster, and its width by measurement at the base of the cell cluster using a stage micrometer. Cell clusters were defined as cells embedded within an exopolysaccharide matrix attached to the substratum and lacking motility; void areas within cell clusters were determined by the observation of free-swimming bacteria within a space inside a cell cluster.

Example 8

Inhibition of Biofilm Development

A flow cell was used to culture bacteria on the surface of a glass substratum (described above). Biofilms of P. aeruginosa were grown at room temperature over a period of 99 hours in the presence and absence of CSM (diluted 1:125 to match the concentration of the chloroform extracted organic material found in spent medium) in modified EPRI medium. During the course of the experiment, the total cell coverage of the bacteria on the surface and average biofilm thickness were determined by counting 20 microscope fields using a 50×ULWD MSPlan objective lens for each time point. Using the image analysis software, ImagePro Plus, the total area of cells per $cm^2$ was determined at 72 hours and 99 hours. Thickness was determined by measuring the average maximum height of 20 random cell clusters at 72 hours and 99 hours of growth. Control samples were grown and tested in the presence of modified EPRI medium with no added CSM. Results from these experiments showed that surface area coverage of the growing biofilm was significantly reduced when biofilms were grown in the presence of CSM compared to biofilms grown in EPRI medium alone. The addition of CSM also caused a significant reduction in the average biofilm cell cluster thickness after 99 hours growth, compared to samples not treated with CSM (FIG. 18).

Example 9

Spectral Analysis of P. aeruginosa CSM and Cis-2-Decenoic Acid

All CSM samples prepared in purified water were lyophilized and resuspended in appropriate carriers for each spectroscopic analysis. CSM controls in all experiments consisted of CSM HPLC products that did not induce dispersion as determined by microtiter plate dispersion bioassay, and carrier solution not containing CSM.

Example 10

Mass Spectroscopy

Samples were resuspended in carrier solution (50% water, 50% methanol and 0.01% formic acid). Mass spectroscopy was performed using a high-performance, hybrid quadru-pole time-of-flight mass spectrometer—QSTAR® XL Hybrid LC/MS/MS System (Applied Bio systems, Foster City, Calif., USA)—in positive ion mode, at room temperature, with an IonSpray source for API 150EX™, API 3000™ and QSTAR® Systems (Applied Biosystems). Data were analyzed using Analyst QS version 1.1.

Example 11

Nuclear Magnetic Resonance (NMR)

Samples of CSM and cis-2-decenoic acid were resuspended in 1 mL of deuterated acetonitrile and inserted into a thin walled NMR sample tube (VWR). Analyzes was performed in a 300 MHz Proton NMR-Bruker AC 300 (Bruker Daltonics Inc., Vilarica, Mass., USA). Spectra were accumulated for 24 hours.

Example 12

Gas Chromatography-Mass Spectroscopy (GC-MS)

Samples of CSM and concentrations of cis-2-decenoic acid from 0.01 mg/mL-10 mg/mL were resuspended in 2 mL of acetonitrile. A 3 step-sequential hexane extraction was performed to remove soluble organic sample material. Hexane was evaporated to dryness in a water bath (55-70° C.). Puridine (250 µL) was subsequently added to solubilize samples for injection into GC. Spectra were obtained with a Shimadzu QP5050A GC-MS system, using helium as a carrier as and a Restek (Columbia, Md.) XTI-5 GC column (30 m, 0.25 mm i.d., 0.25 µm film thickness) with a 1 mL/min flow rate. All analyses incorporated splitless injection and electron impact ionization. The interface temperature between the GC and the MS was maintained at 310° C. Data were analyzed using the program Lab Solutions, GCMS solution version 1.2.

Example 13

Infrared Spectroscopy (IR)

Samples of CSM and cis-2-decenoic acid were weighed before and after lyophilization to determine the amount of KBr to add to each sample. KBr was added at 10 times the sample mass and mixed using a mortar and pestle. The resulting powder was formed into a pellet using a Carver 4350 Manual Pellet Press (Carver Inc., Wabash, Ind., USA). Pressure was applied at 10 Tons for 10 min. IR spectra were obtained using a Bruker Equinox 55 FT-IR spectrometer at room temperature in the range of 3500 $cm^{-1}$ to 400 $cm^{-1}$ at a resolution of 1 $cm^{-1}$. The final spectra represent the mean of 128 scans. Each sample was measured in triplicate.

Example 14

Biofilm Bacteria are Resistant to Antibiotics

FIG. 1A illustrates schematically how biofilm bacteria are resistant to the addition of antibiotics, with similar resistance shown for biocides and other antimicrobial treatments. FIG. 1B illustrates that if a dispersion inducer is added in addition to antibiotic, the dispersed bacteria lose their resistance and become susceptible to the antibiotic.

Example 15

Effect of Dispersion Inducing Compounds

Figure 2B:
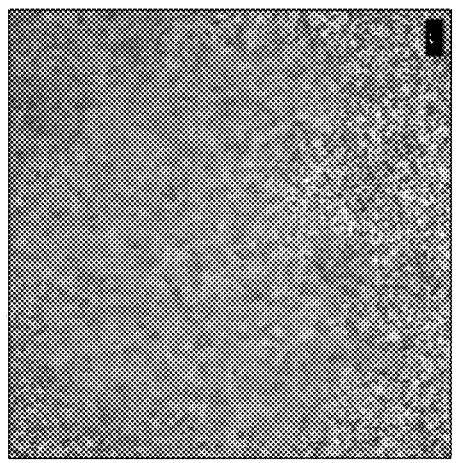
Figure 2A:
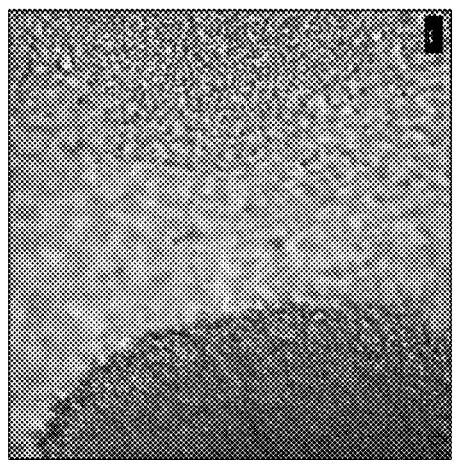

FIG. 2 shows an actual biofilm sample treated with the dispersion inducing compound according to the present invention, derived from cultures of Pseudomonas aerugi-

*nosa*. In this experiment, a once-through flow-cell was used to culture *P. aeruginosa* over a period of six days prior to testing with added CSM.

The flow cell was constructed of anodized aluminum, containing a chamber 1.0 mm by 1.4 cm by 4.0 cm capped with a glass cover slip. Sterile EPRI medium was pumped from a 2-liter vessel through silicone tubing to the flow cell using a Masterflex 8-roller-head peristaltic pump at a flow rate of 0.13 ml/min. Flow through the chamber was laminar, with a Reynolds number of 0.17, having a fluid residence time of 4.3 min. Medium leaving the flow cell was discharged to an effluent reservoir via silicone tubing. The entire system was closed to the outside environment but maintained in equilibrium with atmospheric pressure by a 0.2-µm-pore-size gas-permeable filter fitted to each vessel. Log-phase *P. aeruginosa* (approximately $10^8$ CFU/ml) were inoculated as a 3.0-ml slug dose through a septum 4 cm upstream from the flow cell under flowing conditions. Cells attached to the inner surface of the glass cover slip were viewed by transmitted light using an Olympus BX60 microscope and a 50× magnification ULWD MSPlan long working distance Olympus objective lens. All images were captured using a Magnafire cooled three-chip charge-coupled device (CCD) camera (Optronics Inc., Galena, Calif.) and stored as separate digital files for subsequent retrieval and analysis. Following development of a mature biofilm within the flow-cell, medium-flow was stopped and 3 mL of filtered CSM in sterile EPRI medium was added to the flow-cell. Transmitted light images of a single location within the flow-cell were taken before and during treatment with CSM. FIG. 2 shows images taken from such an experiment 1 min prior to addition of CSM, 5 min after addition of CSM, and 30 min after addition of CSM. Control samples were also run in the same manner as the test samples with the exception that CSM was not included with the 6 mL of added EPRI medium. Results from the control samples showed no change in biofilm cell numbers or biofilm architecture, with no dispersion evident.

Example 16

Biofilm Bacteria Undergo a Phenotypic Switch

Figure 3A:
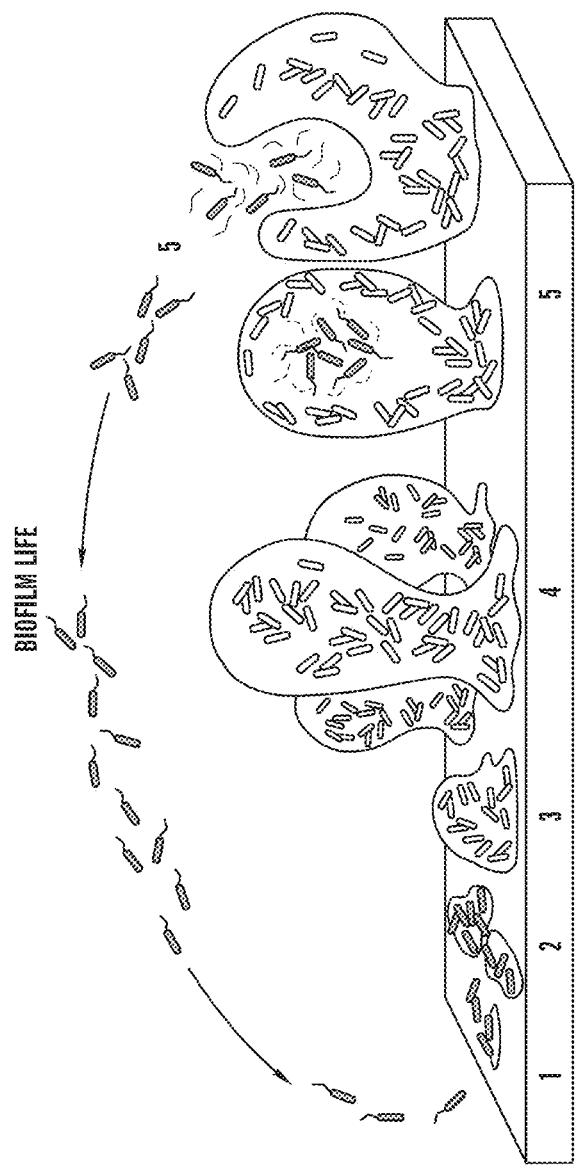
FIG. 3A is a schematic representation of the life cycle of a biofilm. 1, Planktonic bacteria are transported (actively and passively) to the substratum. 2, Cell surface molecules interact with the substratum resulting in reversible surface attachment. 3, Phenotypic changes in the bacterial cell result in cell surface modifications and the production of extracellular polymeric substances, which irreversibly cement the cells to the surface. 4, Physiological changes continue with alterations in metabolism, cell-cell signaling and morphology as biofilm maturation occurs. 5, Cells release degradative enzymes to digest matrix polymer material and alter surface appendages as biofilm detachment occurs. The series of photomicrographs at the bottom of FIG. 3B, show, in order, phase contrast photomicrographs of the five stages of biofilm development by $P.$ $aeruginosa$ grown in continuous culture in a flow-cell and imaged by microscopy. (Sauer et al., "$Pseudomonas$ $aeruginosa$ Displays Multiple Phenotypes During Development as a Biofilm," J. Bacteriol. 184:1140-1154 (2002), which is hereby incorporated by reference in its entirety).
Figure 3B:
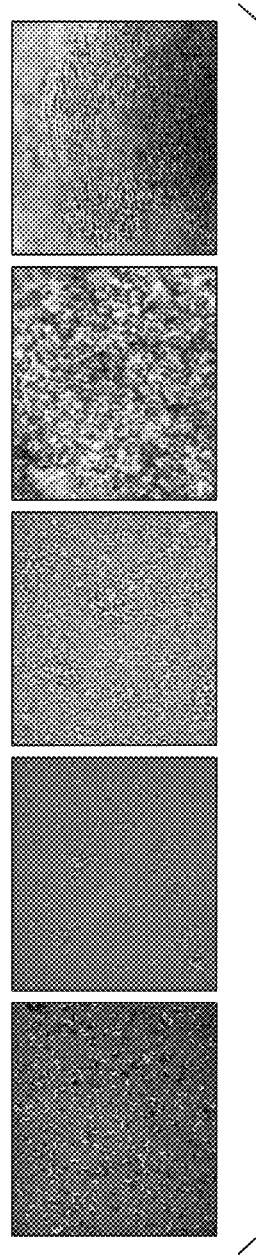

During the course of normal biofilm development, biofilm bacteria undergo a phenotypic switch at the end of maturation II stage (FIG. 3) in which their physiology changes from a predominantly biofilm form to a predominantly planktonic form. Microscopic observations of biofilms during the dispersion phase demonstrated that bacteria within cell clusters become motile (maturation stage *P. aeruginosa* are non-motile), while the bacteria around the edges of the clusters remain fixed. The region of the cell cluster within which bacteria can swim/twitch grows in volume from a (usually) central location and eventually a breach is made in the cluster wall. The bacteria are able to swim through this breach and enter the bulk liquid phase leaving behind a void within the cell cluster.

Continued study of the dispersion response has revealed that cell clusters transition through episodes of growth and dispersion; the same cell cluster often enduring many such cycles. Multiple dispersion and regrowth events generally lead to the development of cell clusters with patterns analogous to growth rings which can indicate the number of times that dispersion has occurred. Often cell clusters will detach from the substratum completely during a dispersion event (Stoodley et al., "Growth and Detachment of Cell Clusters from Mature Mixed-species Biofilms," Appl. Environ. Microbiol. 67:5608-5613 (2001), which is hereby incorporated by reference in its entirety). This effect is thought to be due to weakening of attachment structures at the base of the cell cluster allowing fluid sheer to detach the cluster.

Example 17

Cell Detachment after Medium Stagnation

Figure 4A:
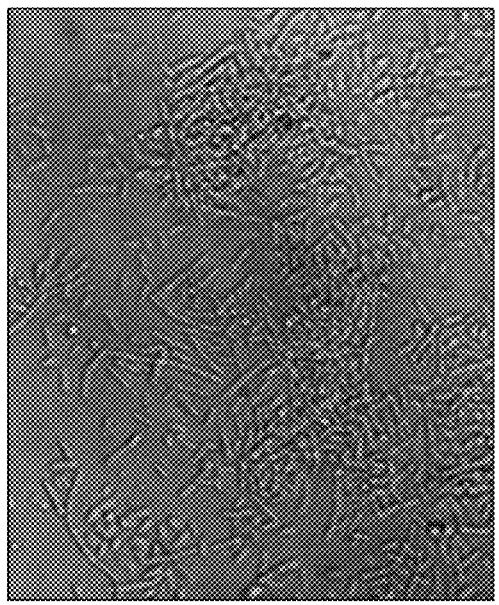
FIGS. 4A-B are phase contrast photomicrographs of biofilm 20 dispersion induced by cessation of flow.
Figure 4B:
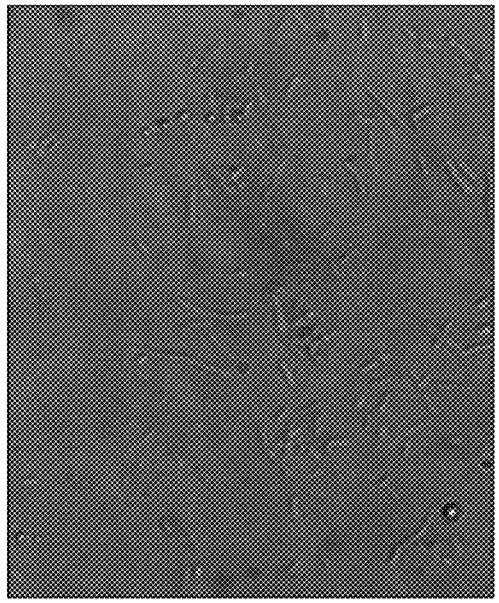
Figure 5:
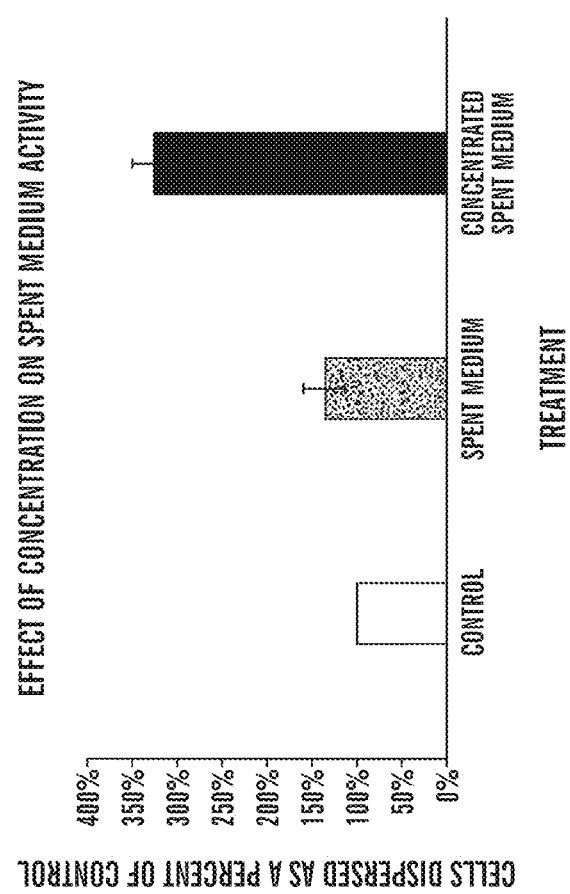
FIG. 5 is a graph showing the effect of chloroform extraction on spent medium dispersion activity. Biofilms were cultured for six days in continuous culture in EPRI medium in biofilm tube reactors (Sauer et al., "$Pseudomonas$ $aeruginosa$ Displays Multiple Phenotypes During Development as a Biofilm," J. Bacteria 184:1140-1154 (2002), which is hereby incorporated by reference in its entirety) and treated with spent medium (control) and chloroform extracted spent medium (CSM). Cell dispersion was determined as the optical density of culture effluent collected at the end of culture tubes. The error bar represents standard deviation for three replicate experiments.

FIG. 4 depicts a time series of phase contrast photomicrographs showing the detachment of cells after medium stagnation of 72 hours. Flow-cell were inoculated with *P. aeruginosa* PAO1 and cultured for a period of three days, according to the method described in Example 3, above. The choice of three days for culture of these biofilms was based upon the observation that under continuous flow, cell clusters within a biofilm of *P. aeruginosa* were observed to undergo spontaneous dispersion events following 9 days of incubation. After 72 days of growth under continuous flow, medium flow was stopped and images of the cell clusters were recorded every two hours for a period of 96 hours. After 72 hours of medium stagnation, the cell clusters within the flow-cell were observed to dis-aggregate, with cells entering the bulk liquid medium as planktonic bacteria (FIG. 4). These experiments demonstrated that cessation of flow induced dispersion of biofilms. response. In these experiments, dispersion occurred not simply within the cell clusters, but throughout all clusters in the biofilm. Only those cells which were directly attached to the substratum were not observed to swim into the bulk liquid, as illustrated in FIG. 4.

Example 18

Development of Chloroform Extraction Method

Various growth and extraction procedures were tested to develop a reliable method of extracting the active fraction of spent culture medium having dispersion inducing activity. Chloroform was chosen as the extraction solvent of choice due to its compatibility with HPLC fractionation procedures, because it resulted in a narrow range of extractable organic compounds (as determined by mass spectrometry) and because it could recover bioactive amounts of the dispersion inducing agent. The method currently used for chloroform extraction of spent medium follows: Bacterial cultures of *P. aeruginosa* PAO1 were grown in 4 liters of EPRI medium (containing: sodium lactate 0.05 g/l, sodium succinate 0.05 g/l, ammonium nitrate 50.381 g/l, $KH_2PO_4$ 0.19 g/l, $K_2HPO_4$ 0.63 g/l, Hutner Salts metals solution 1 ml, and glucose, 2.0 g/l) in a batch culture vessel for six days at room temperature with continuous stirring. Following growth, bacteria were removed from the culture medium by centrifugation at 10,000×g for 20 min, followed by filtration of spent medium through a 0.22 µm pore size filter. In batches, 250 ml of filtered spent medium were mixed with 80 ml of chloroform in a reparatory funnel. The chloroform fraction was removed after a separation time of 10 min. The chloroform samples were then evaporated to dryness at 70° C. using a rotavapor R-3000 (Büchi Laboratories, Flawil, Switzerland) and re-suspended in 6 mL of filtered nanopure water or EPRI medium. The final product, resulting from the chloroform extraction procedure is referred to here as concentrated spent medium or CSM. FIG. 15 shows the results of comparing the effect of CSM and Spent Medium on continuous culture biofilms grown in biofilm tube reactors. CSM and Spent medium were prepared as described previously from cultures of *P. aeruginosa* PAO1 grown at 22° C. for 9 days in EPRI medium supplemented with 2.0 gram per Liter of glucose. Biofilms of *P. aeruginosa* PAO1 were cultured for six days at 22° C. in biofilm tube reactors consisting of 32 cm silicone dioxide Masterflex size 14 tubing. At the end of six days, 6 mL of CSM, Spent Medium or Sterile EPRI medium, each supplemented with 2.0 gram per Liter glucose, was added to the tubes. The effluent from the tubes was collected and pooled for each treatment over a period of 20 minutes. Pooled sampled were assayed for optical density at 570 nm to determine relative cell numbers dispersed from each treatment. Each experiment was performed with five replicates. Results from these experiments demonstrated that chloroform extracted spent culture medium, CSM showed a greater activity in dispersing biofilms of *P. aeruginosa* compared to spent medium.

Figure 6A:
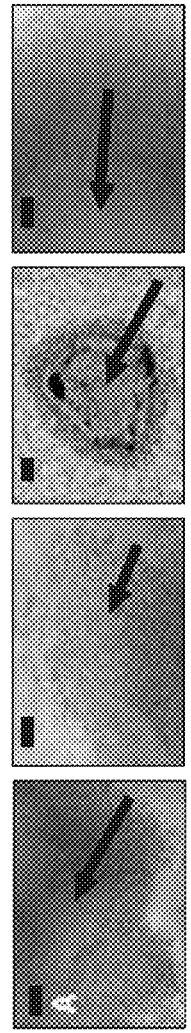
FIG. 6A shows microcolonies of $P.$ $aeruginosa$ biofilms grown in continuous culture demonstrating native dispersion response. During the dispersion stage of biofilm development, bacteria become motile within cell clusters and exit to the bulk liquid through a breach in the microcolony wall. Each photomicrograph shows a microcolony whose interior has been voided in this manner. The arrow indicates the location of a void. Images taken at 1000× magnification; bar represents 10 µm.
Figure 6B:
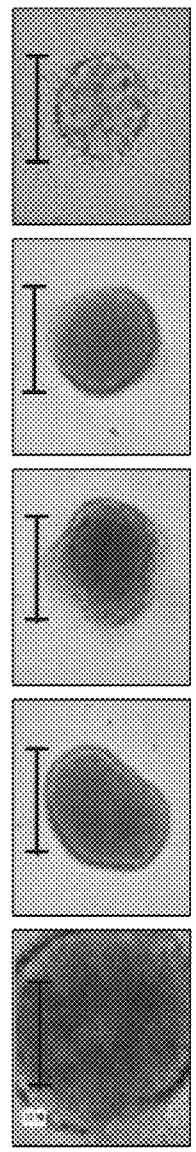
FIG. 6B is a transmitted light image.
Figure 6C:
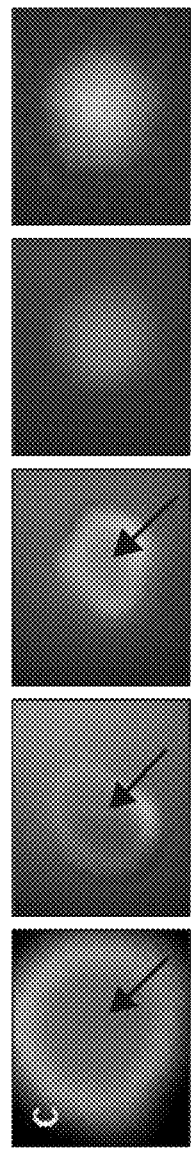
FIG. 6C is a fluorescent image showing the size dependence of dispersion response. Biofilm microcolonies growing in continuous culture having dimensions of greater than 40 µm diameter×10 µm thickness show dispersion (left 3). Microcolonies below this minimum dimension remain "solid" (right 2 photomicrographs). Fluorescence indicates presence of cells (lacZ reporter on chromosome). All images are the same relative size at 500× magnification; bars represent 40 µm. Arrows indicate void areas within microcolony.

Applicant observed that *P. aeruginosa* PAO1 will disperse from a continuous culture biofilm grown on a glass substratum in a flow-cell reactor after medium flow had been stopped for several hours. This observation has led to the hypothesis that biofilm dispersion may result from the accumulation of an extracellular messenger which acts as an inducer of biofilm disaggregation. This hypothesis is supported by observations that biofilms of *P. aeruginosa* will not form in batch culture flasks, but will form on the walls of a chemostat, indicating that accumulation of a signal for dispersion may prevent biofilm development. Furthermore, when grown in continuous culture, microcolonies of *P. aeruginosa* will form hollow voids at their center when they attain a minimum diameter of 40 microns and thickness of 10 microns (FIG. 6). The microcolony size within which these voids form, however, is dependent on the fluid flow rate. When flow in a biofilm reactor was increased, the diameter and thickness at which microcolony void formation occurred also increased, indicating a relationship between dispersion induction and transport. These observations hinted that an extracellular substance produced by *P. aeruginosa* was responsible for inducing biofilm dispersion.

Figure 7B:
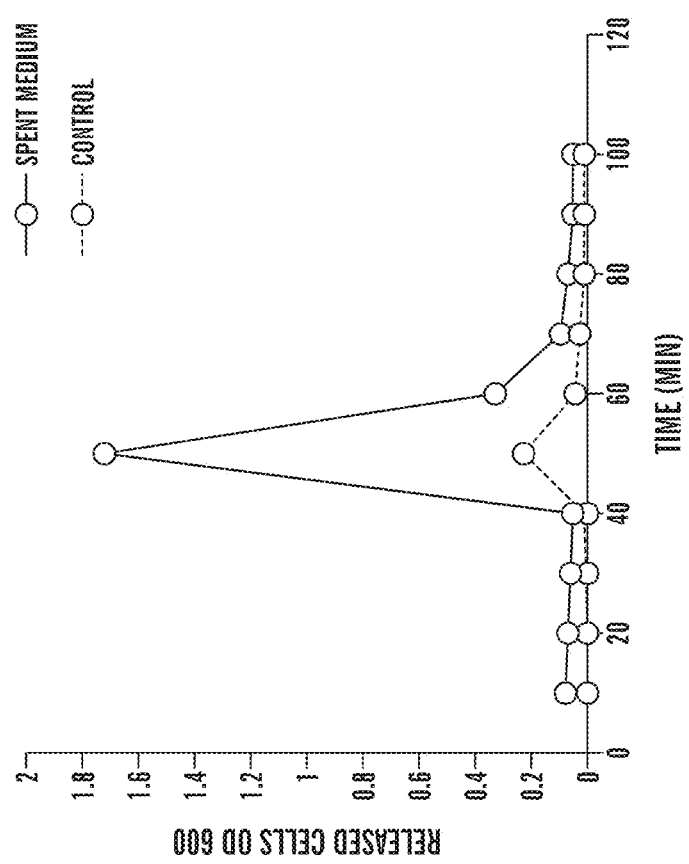
Figure 7A:
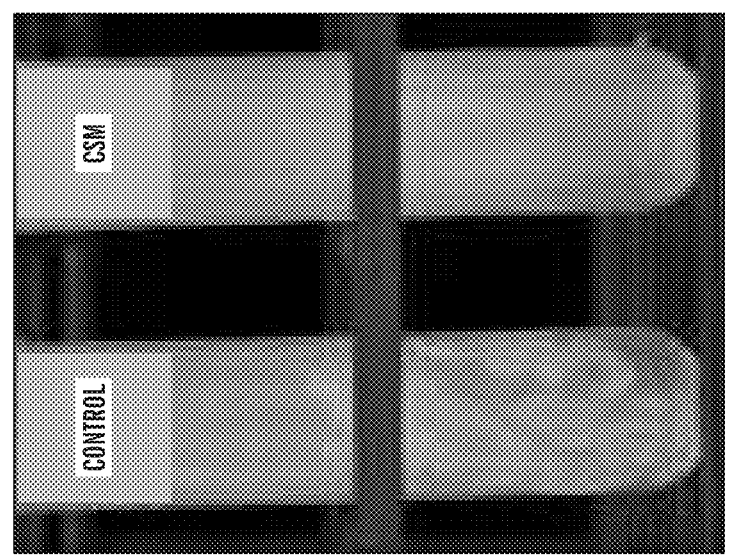

If *P. aeruginosa* produces an extracellular dispersion-inducing compound, applicant postulated that the addition of cell-free spent culture medium to mature *P. aeruginosa* biofilms should cause the release of cells into the bulk liquid medium. These bacteria should be detectable as an increase in the number of cells recovered in the reactor effluent. FIG. 7A illustrates results from a representative experiment in which biofilms were treated for 70 minutes under continuous flow with cell-free spent medium in which *P. aeruginosa* had been grown in suspension for 24 hours; fresh medium was added to control biofilms. Prior to addition, spent medium was aerated, supplemented with glucose and its pH adjusted to neutrality, to ensure that starvation, oxygen depletion or a change in pH was not responsible for the release of bacteria. A large spike in the effluent cell number was detectable compared to control lines within 20 minutes of the addition of the spent medium, indicating the release of biofilm bacteria into the effluent of cultures treated with spent medium. A small spike of released cells was also detectable in control samples, likely representing a response to the physical or mechanical effects associated with switching lines to a fresh medium reservoir.

To purify the active dispersion inducing fraction of spent medium, cell-fee stationary-phase batch cultures of *P. aeruginosa* were extracted using chloroform, followed by rotory evaporation of the chloroform and re-suspension of the organic fraction in fresh medium or buffer solution (resulting in a 125-fold increase in the chloroform-soluble organic fraction). This preparation is referred to as CSM. To test the dispersion-inducing activity of CSM, *P. aeruginosa* biofilms were grown in continuous culture in silicone tubing and exposed the biofilms for one hour to medium amended with CSM. The extruded contents of the tube reactors showed a largely intact biofilm in the control line treated with fresh medium (FIG. 7B), while the contents of the tubes treated with CSM showed the biofilm to have completely disaggregated (FIG. 7C). Studies of 4-day old biofilms grown in continuous culture in silicone tubing revealed that treatment with CSM-containing medium for one hr was effective in releasing an average 87.4% (±1.4%) of biofilm cells as determined by colony forming units released into the effluent. Spent medium was shown to have an average dispersion efficacy of 32.4% (±5.5%).

Microscopy was used to evaluate the effect of CSM on biofilm microcolonies grown for six days in continuous culture on the glass substratum of a flow-cell mounted to a microscope (K. Sauer et al., J. Bacteriol. 184:1140 (2002), which is hereby incorporated by reference in its entirety). Prior to the addition of CSM, a well-developed microcolony was observed to contain cells that were stationary and showed no sign of motility (FIG. 7D). Following 7 minutes of contact with CSM-containing medium, cells within the microcolony began to twitch and display active motility (FIG. 7E). After 30 minutes, the microcolony had become completely disaggregated and cells were observed to swim freely through the medium (FIG. 7F). When compared to natural dispersion, exogenously induced dispersion was observed to progress from the outside of the microcolony towards the interior and, instead of creating a central void, resulted in complete disaggregation of the microcolony.

Figure 8A:
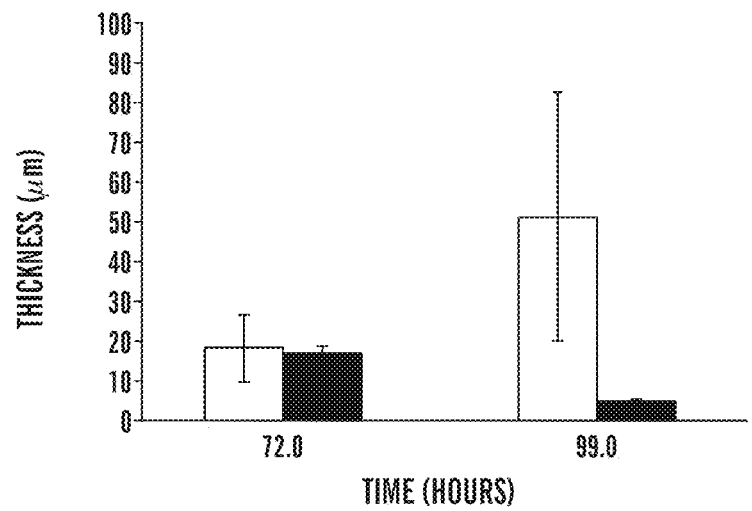
FIGS. 8A-B show biofilm development in the continuous presence of CSM diluted in modified EPRI to concentration of Spent medium. Average thickness (FIG. 8A) and surface area of biofilms grown in the presence of CSM (FIG. 8B) are significantly less than for untreated biofilms. Grey bars, biofilms treated with CSM. Black bars, biofilms grown in the absence of dispersion inducer. Error bars represent one standard deviation for 20 randomly selected microcolonies
Figure 8B:
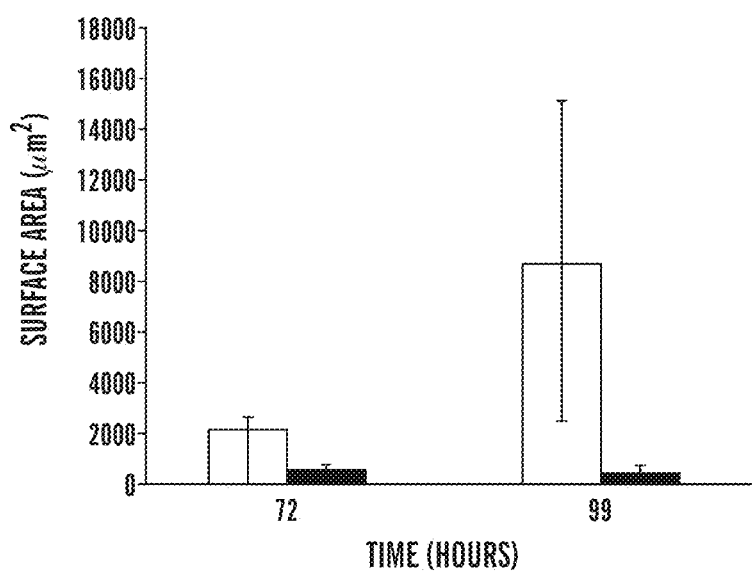

When added continuously to flow cells, CSM adjusted to the concentration of spent medium, showed a significant inhibition of biofilm development over a period of 99 hr, demonstrating a reduction in both biofilm average thickness and surface area coverage (FIG. 8). Exogenous dispersion induction of pre-formed biofilms by CSM was measurable at all time points from day 1 (beginning of biofilm microcolony formation) through day 6, after which natural dispersion began to occur. Activity of CSM was shown to persist up to 6 months with no significant reduction when stored under refrigeration. Extraction of spent medium by ethyl acetate (to recover acyl-homoserine lactones) did not result in a preparation with dispersion activity.

Figure 9:
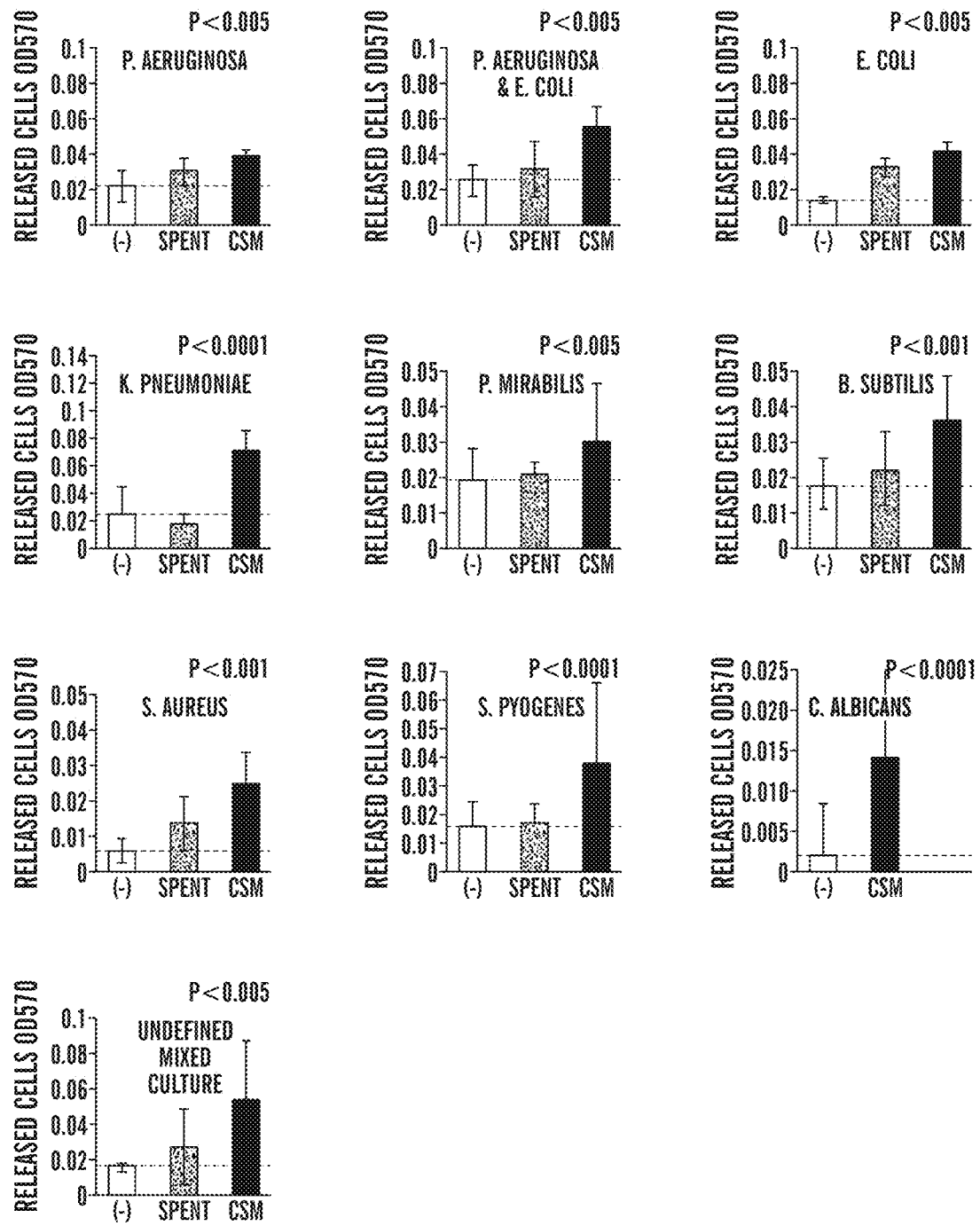
FIG. 9 shows dispersion of different bacterial biofilms by $P.$ $aeruginosa$ CSM using microtiter plate dispersion bioassay. Y-axis indicates number of cells released into the bulk liquid of 16 replicate wells in 3 replicate experiments, following treatment for 1 hr with CSM or carrier control (−), containing sterile medium. Hatched line indicates level of dispersion in carrier control samples. All differences between CSM samples and controls are statistically significant at indicated P-value as determined by Student's T-test.

Having demonstrated dispersion induction against mature and developing biofilms formed by *P. aeruginosa*, the ability of CSM to induce dispersion in biofilm cultures of *E. coli*, *E. coli* mixed with *P. aeruginosa*, an undefined mixed bacterial biofilm derived from airborne contaminants, and against biofilms formed by *Klebsiella pneumoniae*, *Proteus mirabilis*, *Streptococcus pyogenes*, *Bacillus subtilis*, *Staphylococcus aureus*, and *Candida albicans* was next tested. CSM was shown to stimulate significant dispersion compared to controls in all samples tested. Results from these experiments are summarized in FIG. 9. The ability of *P. aeruginosa* dispersion inducer to activate dispersion in different species of bacteria and in yeast indicates that it possesses cross-phylum and cross-kingdom activity.

Figure 10A:
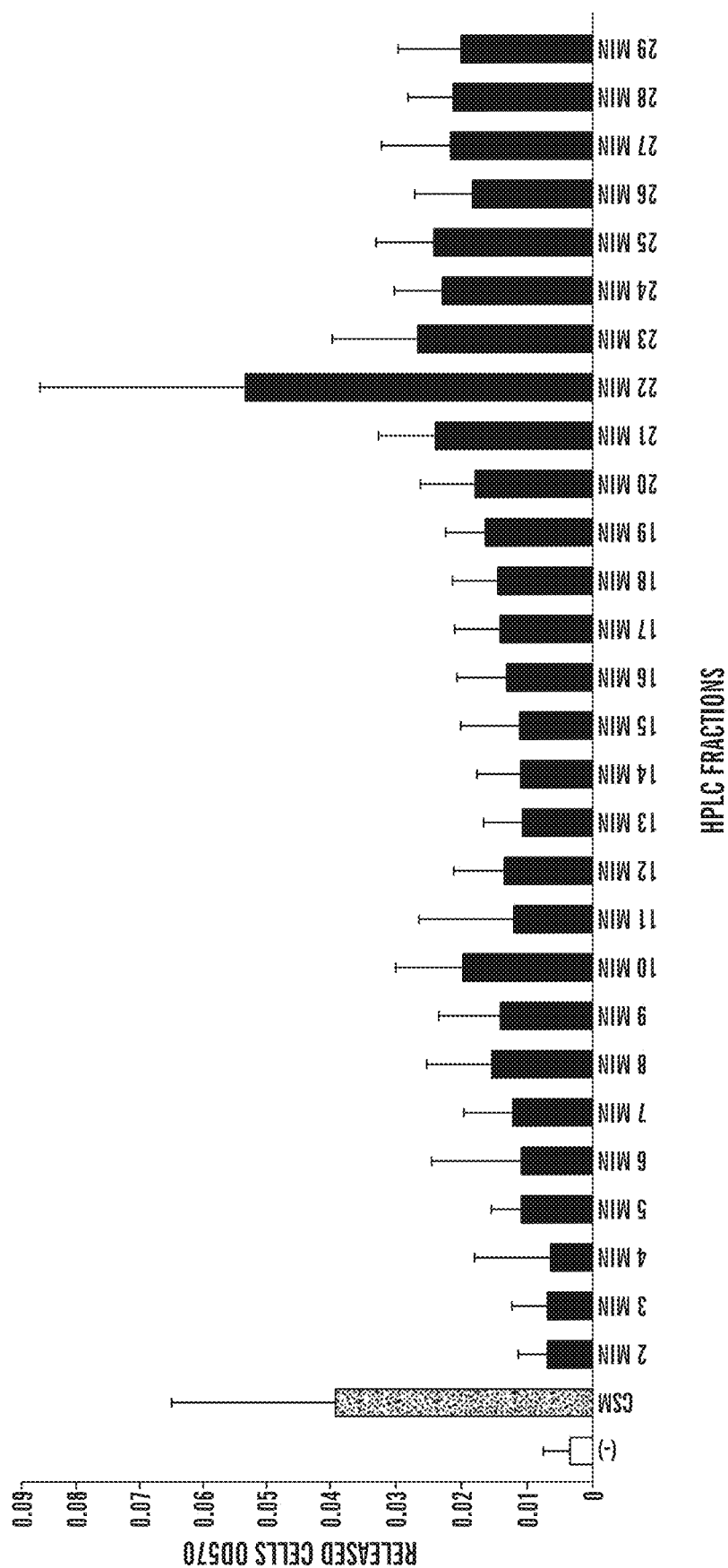
FIGS. 10A-C show a microtiter plate dispersion bioassay.

Having established the role of CSM as an inducer of biofilm dispersion, the active molecule or molecules present in CSM was identified. This began by assaying the dispersion activity of multiple fractions of CSM separated by Isocratic gradient in acetonitrile and water using C-18 reverse phase high performance liquid chromatography (HPLC). Eluted HPLC fractions (collected at one minute intervals) were desiccated in a Speedvac to remove residual acetonitrile and re-suspended in purified water and tested by microtiter plate dispersion bioassay to determine dispersion activity. FIG. 10A shows the results of CSM fractionation biofilm dispersion assays. The results indicated that the HPLC fraction of CSM showing the highest activity eluted at 22 min, an acetonitrile/water ratio of 70%/30%.

Mass spectrometry of the active HPLC CSM fraction showed a consistent molecular peak with low ionization activity at 171 M/Z (mw=170). This peak was present in all samples showing dispersion activity and missing from all samples lacking dispersion activity. This peak was also shown to be missing from all carrier liquids and solvents used in preparing CSM (including fresh culture medium). Mass spectroscopy-product ion analysis of the 170 mw peak, solubility analysis, $H^1$- and $C^{13}$ nuclear magnetic resonance (NMR) spectroscopy and infrared (IR) spectroscopy have demonstrated that the 170 mw molecule was a mono-unsaturated $C_{10}$-fatty acid, with a double bond located at the number 2 carbon; 2-decenoic acid.

Figure 12A:
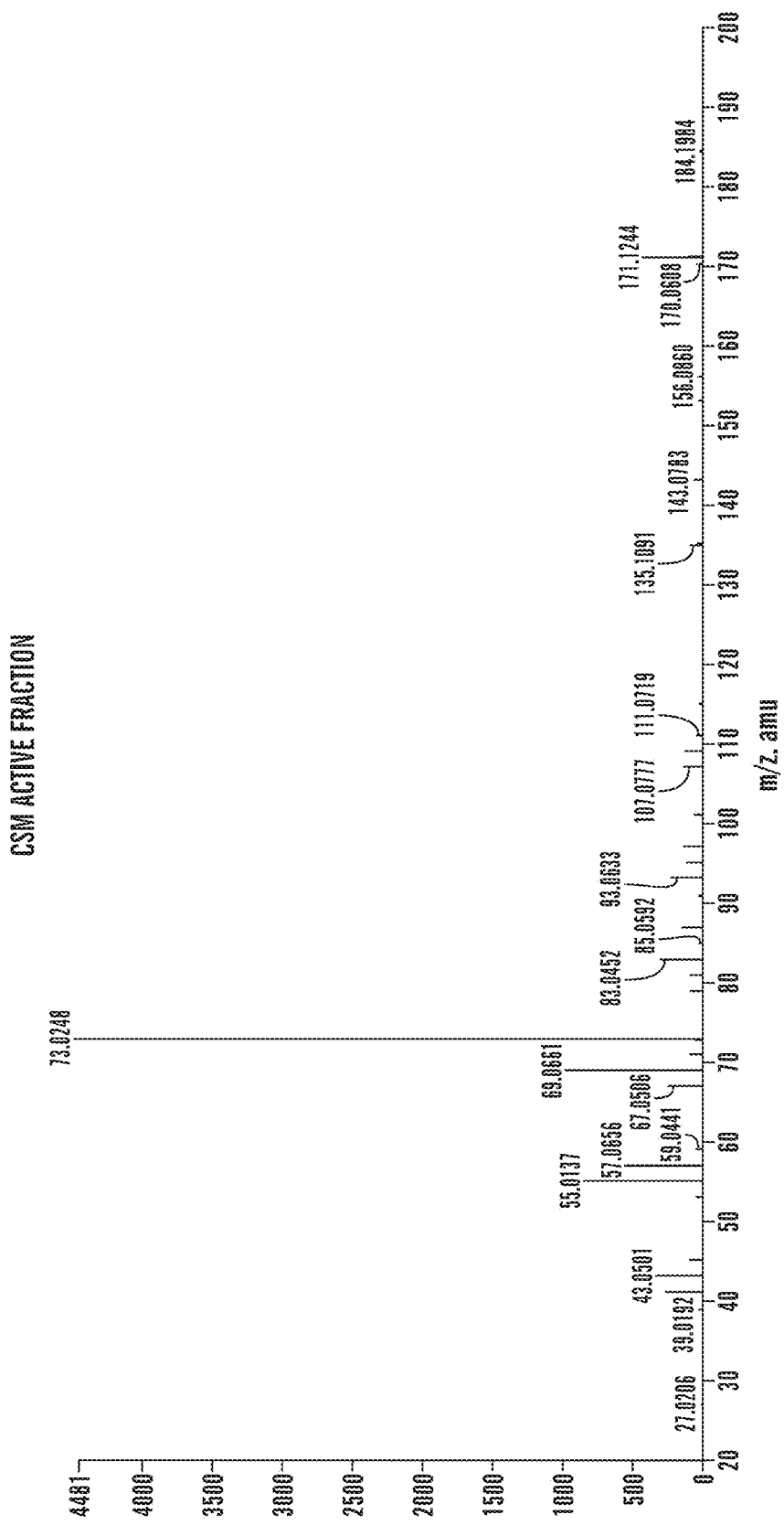
FIGS. 12A-C show the spectral analysis of $P.$ $aeruginosa$ CSM and cis-2-decenoic acid.
Figure 12A:
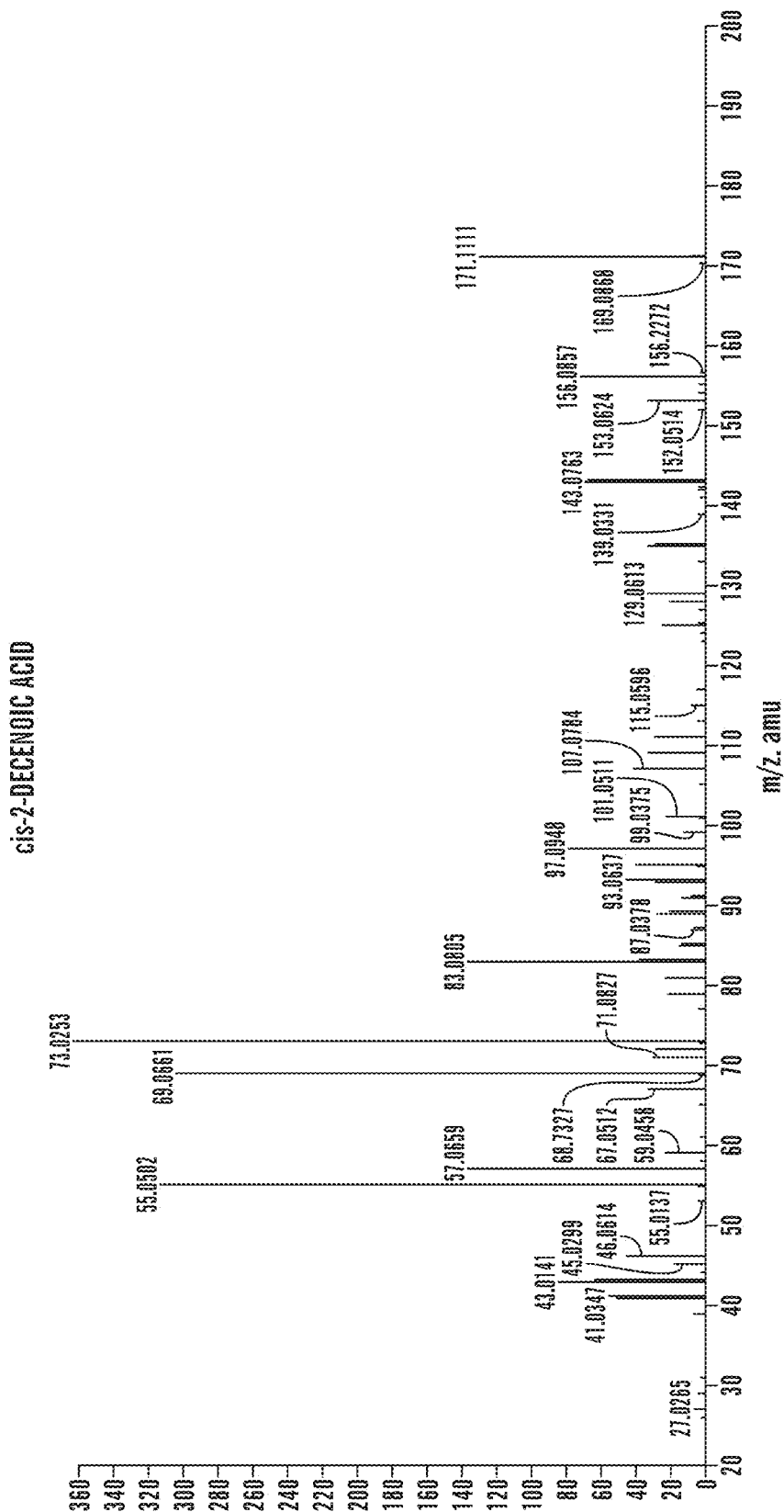
Figure 12B:
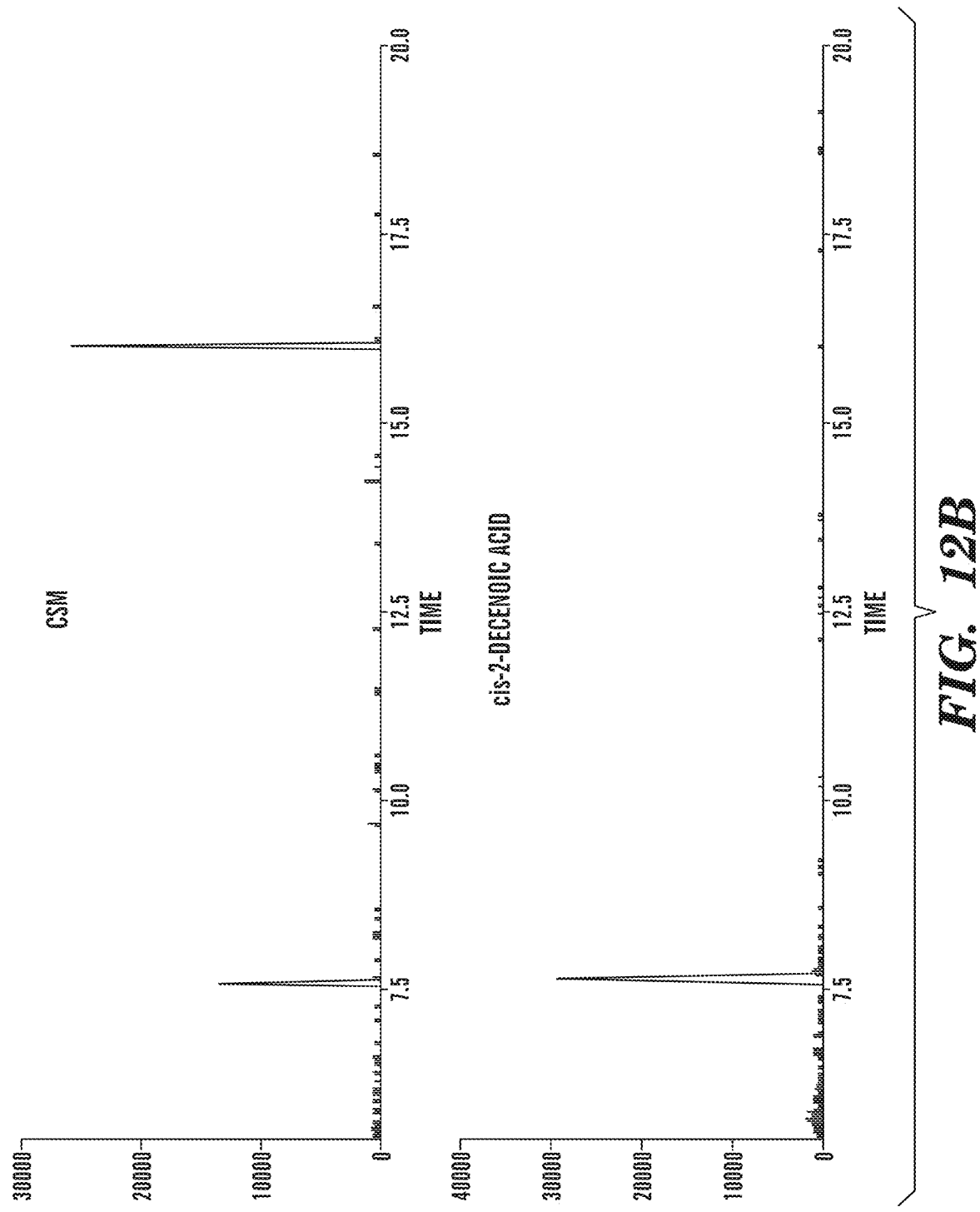
Figure 12C:
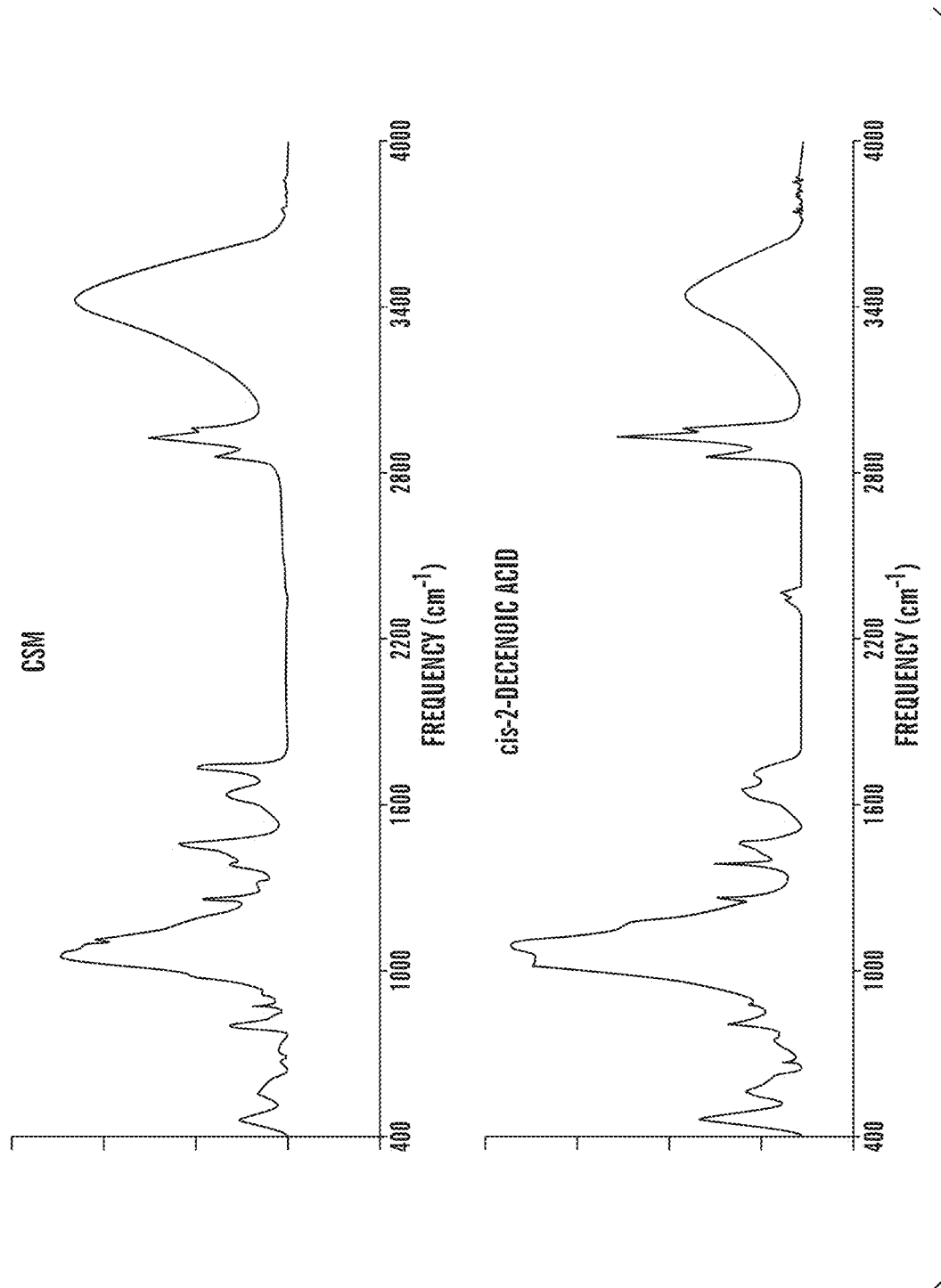

In order to confirm that the 170-mw molecule (M/Z=171) from the 22-minute CSM HPLC fraction was identical to 2-decenoic acid, the original molecule was fragmented in the mass spec to generate product ion peaks. The product ions from the active CSM fraction and 2-decenoic acid were analyzed by quadrapole ms/ms to evaluate cleavage differences between these two molecules. FIG. 12A, shows that the 171 M/Z CSM sample had identity with 2-decenoic acid. When analyzed by GC-MS, unfractionated CSM displayed a single major peak with a retention time of 7.6 min identical to that of 2-decenoic acid FIG. 12B. Infrared spectroscopy confirmed that the cis isomer of 2-decenoic acid was the organic compound isolated from CSM, FIG. 12C.

Figure 10B:
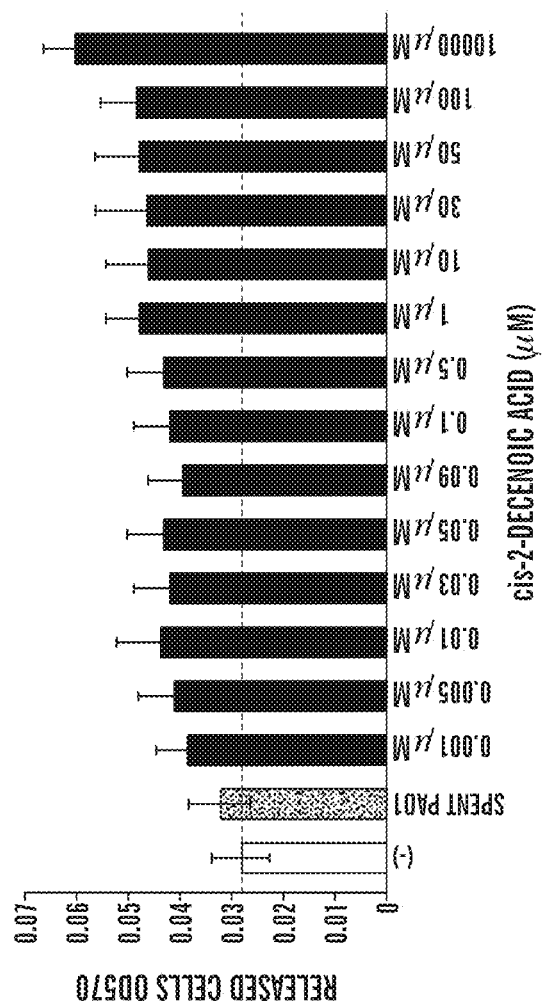
Figure 10C:
Figure 11:
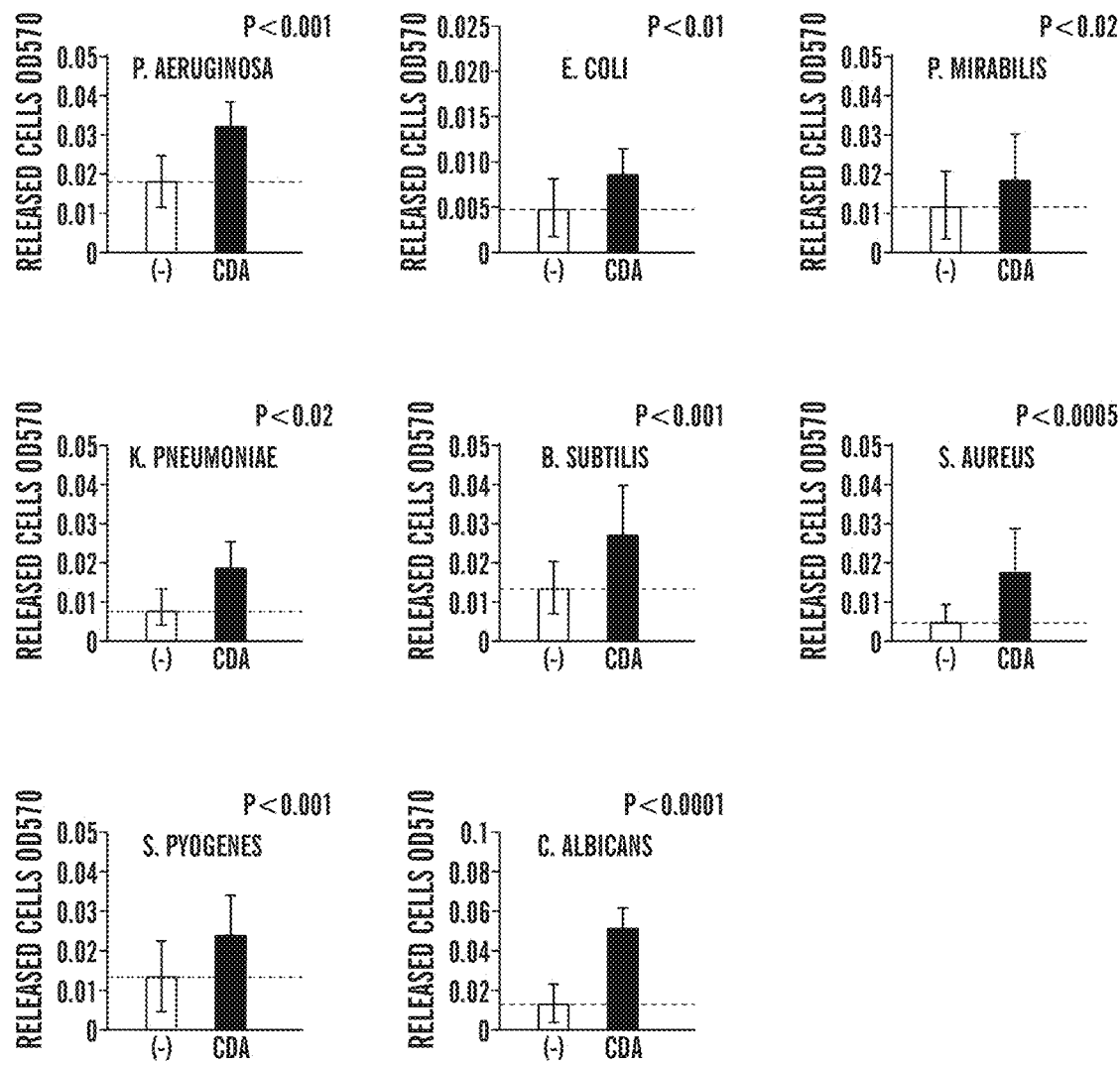
FIG. 11 shows dispersion of different bacterial biofilms by cis-2-decenoic acid using microtiter plate dispersion bioassay. Y-axis indicates number of cells released into the bulk liquid of 16 replicate wells in 3 replicate experiments, following treatment for 1 hr. with 0.01 µM cis-2-decenoic acid (CDA), or carrier control (−), containing medium+10% ethanol. Hatched line indicates level of dispersion in carrier control samples. All differences between cis-2-decenoic acid treated samples and controls are statistically significant at indicated P-value as determined by Student's T-test.

Following this identification, mono-unsaturated fatty acid molecules of various molecular weights were synthesized and tested these for dispersion activity. DSF, which was shown to disrupt cell flocs of *X. campestris* was shown not to promote dispersion of *P. aeruginosa*. The compounds having the highest activity were two isomers of 2-decenoic acid. The trans isomer (trans-2-decenoic acid) was shown by microtiter plate dispersion bioassay to have activity only at millimolar concentrations, typically not low enough to qualify as a cell-cell signaling molecule. FIG. 10B shows the dispersion activity of increasing concentrations of cis-2-decenoic acid against biofilm cultures of *P. aeruginosa* grown in microtiter plates. These results demonstrated that the cis isomer (cis-2-decenoic acid) was active over a concentration range of 1.0 nanomolar to 10 millimolar, showing greater dispersion activity at 1.0 nanomolar than un-concentrated spent culture medium (i.e.: higher than the naturally occurring inducer). Microscopy revealed that the activity of cis-2-decenoic acid as a dispersion inducer was similar to CSM activity, completely disrupting a biofilm microcolony as shown in FIG. 13. The activity of cis-2-decenoic acid was also tested against *E. coli, S. pneumonia, P. mirabilis, S. pyogenes, B. subtilis, S. aureus*, and *C. albicans* biofilm cultures, resulting in similar results to those obtained for CSM (FIG. 11).

This study has shown that a small messenger fatty acid molecule, cis-2-decenoic acid, is produced by *P. aeruginosa* in batch and biofilm culture. This molecule has been demonstrated to induce a dispersion response in biofilms formed by *P. aeruginosa* and a range of gram-negative and gram-positive bacteria and in yeast. The dispersion response is a mechanism to escape starvation conditions within a population, allowing fixed cells the opportunity to migrate to a more favorable environment and thin out the population that remains, allowing cells to obtain increased nutrients. When biofilm microcolonies are small, the inducer, which accumulates in the extracellular matrix is removed by diffusive and advective transport. This removal is not possible in batch systems. When cell clusters attain a dimension where the inducer is not adequately washed out from the interior (the rate of diffusion being exceeded by the rate of production), the inducer is able to attain a concentration necessary for activation of the dispersion response, releasing cells from the biofilm. The discovery of a cell-to-cell signaling molecule responsible for biofilm dispersion allows the exogenous induction of the transition of biofilm bacteria to a planktonic state. Use of this dispersion inducer is likely to result in enhanced treatment options in combating biofilm-related infections and in the control of microbial bio fouling.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A medical device or dressing, comprising:
    cis-2-decenoic acid at a concentration of 0.001 µM to 30 µM; and
    a support configured to release the cis-2-decenoic acid over a length of time.

2. The medical device or dressing of claim 1, wherein the cis-2-decenoic acid is at a concentration of 1 µM to 30 µM.

3. The medical device or dressing according to claim 1, wherein the support comprises cotton.

4. The medical device or dressing according to claim 1, wherein the support comprises a polymer selected from the group consisting of a polyamide, a polyester, a polypropylene, a polytetrafluoroethylene, a copolymer, and cellulose.

5. The medical device or dressing according to claim 1, wherein the support comprises a gel.

6. The medical device or dressing of claim 1, wherein the medical device or dressing is selected from the group consisting of: an indwelling medical device, a catheter; a respirator, a ventilator; a stent; an artificial valve; a joint; a pin; a bone implant, a suture; a staple; and a pacemaker.

7. The medical device or dressing of claim 5, wherein the gel is provided as a coating on a fiber.

8. The medical device or dressing of claim 1, wherein the medical device or dressing is a topical dressing.

9. The medical device or dressing of claim 1, wherein the medical device or dressing is non-bacteriocidal.

10. The medical device or dressing of claim 1, wherein the support is a provided as a coating.

11. A coating for a medical device or dressing, comprising:
    a polymer or a gel formulated to coat a medical device or dressing, containing cis-2-decenoic acid in a concentration of 0.001 µM to 30 µM,
    the polymer or gel being configured to prolong a release of the cis-2-decenoic acid with respect to an absence of the polymer or gel, to induce a biological dispersion induction response of a biofilm containing a microorganism exposed to the cis-2-decenoic acid.

12. A biofilm disperser for a medical device or dressing, comprising:
    cis-2-decenoic acid in a concentration of 0.001 µM to 30 µM; and
    a gel or polymer configured to release the cis-2-decenoic acid over a length of time.

13. The biofilm disperser according to claim 12, wherein the the gel or polymer comprises a gel.

14. The biofilm disperser according to claim 12, further comprising a biocide.

15. The biofilm disperser according to claim 12, wherein the medical device is selected from the group consisting of a catheter, a ventilator, and a respirator.

16. The biofilm disperser according to claim 12, wherein the medical device comprises a bone implant.

17. The biofilm disperser according to claim 12, further comprising at least one of a biocide and an antibiotic.

18. The medical device or dressing according to claim 1, wherein the medical device or dressing comprises an implantable medical device.

19. The medical device or dressing according to claim 1, wherein the medical device or dressing comprises a suture or surgical staple.

20. The coating for a medical device or dressing according to claim 11, wherein the medical device or dressing is selected from the group consisting of: an indwelling medical device, a catheter; a respirator, a ventilator; a stent; an artificial valve; a joint; a pin; a bone implant, a suture; a staple; and a pacemaker.

* * * * *